(12) United States Patent
Park et al.

(10) Patent No.: US 8,617,171 B2
(45) Date of Patent: Dec. 31, 2013

(54) PREOPERATIVELY PLANNING AN ARTHROPLASTY PROCEDURE AND GENERATING A CORRESPONDING PATIENT SPECIFIC ARTHROPLASTY RESECTION GUIDE

(75) Inventors: Ilwhan Park, Walnut Creek, CA (US); Keun Song, Palo Alto, CA (US); Oleg Mishin, Foster City, CA (US); Michael Santarella, Essex Fells, NJ (US)

(73) Assignee: OtisMed Corporation, Alameda, CA (US)

( * ) Notice: Subject to any disclaimer, the term of this patent is extended or adjusted under 35 U.S.C. 154(b) by 136 days.

(21) Appl. No.: 13/086,275

(22) Filed: Apr. 13, 2011

(65) Prior Publication Data

US 2011/0214279 A1 Sep. 8, 2011

Related U.S. Application Data

(63) Continuation-in-part of application No. 12/760,388, filed on Apr. 14, 2010, which is a continuation-in-part of application No. 12/563,809, filed on Sep. 21, 2009, and a continuation-in-part of application No. 12/546,545, filed on Aug. 24, 2009, and a continuation-in-part of application No. 12/505,056, filed on Jul. 17, 2009, and a continuation-in-part of application No. 12/111,924, filed on Apr. 29, 2008, which is a continuation-in-part of application No. 11/959,344, filed on Dec. 18, 2007, now Pat. No. 8,221,430.

(60) Provisional application No. 61/102,692, filed on Oct. 3, 2008, provisional application No. 61/083,053, filed on Jul. 23, 2008.

(51) Int. Cl.
*A61B 17/58* (2006.01)
*A61B 17/60* (2006.01)
*A61F 2/00* (2006.01)
*A61F 5/00* (2006.01)

(52) U.S. Cl.
USPC .............................................. 606/88; 606/87

(58) Field of Classification Search
USPC .......................................... 606/88, 87; 703/7
See application file for complete search history.

(56) References Cited

U.S. PATENT DOCUMENTS

| 3,195,411 A | 7/1965 | MacDonald at al. |
| 3,825,151 A | 7/1974 | Arnaud |

(Continued)

FOREIGN PATENT DOCUMENTS

| DE | 3305237 A1 | 8/1983 |
| DE | 4341367 C1 | 6/1995 |

(Continued)

OTHER PUBLICATIONS

Mole et al., "A New Three-Dimensional Treatment Algorithm for Complex Surfaces: Applications in Surgery", Feb. 1995.

(Continued)

*Primary Examiner* — David Bates
(74) *Attorney, Agent, or Firm* — Polsinelli PC

(57) ABSTRACT

Methods of manufacturing a custom arthroplasty resection guide or jig are disclosed herein. For example, one method may include: generating MRI knee coil two dimensional images, wherein the knee coil images include a knee region of a patient; generating MRI body coil two dimensional images, wherein the body coil images include a hip region of the patient, the knee region of the patient and an ankle region of the patient; in the knee coil images, identifying first locations of knee landmarks; in the body coil images, identifying second locations of the knee landmarks; run a transformation with the first and second locations, causing the knee coil images and body coil images to generally correspond with each other with respect to location and orientation.

35 Claims, 38 Drawing Sheets

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,099,846 A | 3/1992 | Hardy |
| 5,122,144 A | 6/1992 | Bert et al. |
| 5,123,927 A | 6/1992 | Duncan et al. |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,298,115 A | 3/1994 | Leonard |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,768,134 A | 6/1998 | Swaelens et al. |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia III et al. |
| 5,908,424 A | 6/1999 | Bertin et al. |
| 5,911,724 A | 6/1999 | Wehrli |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B2 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B2 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |

(56) References Cited

U.S. PATENT DOCUMENTS

| | | |
|---|---|---|
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini |
| D532,515 S | 11/2006 | Buttler et al. |
| 7,141,053 B2 | 11/2006 | Rose et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,177,386 B2 | 2/2007 | Mostafavi et al. |
| 7,184,814 B2 | 2/2007 | Lang et al. |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,383,164 B2 | 6/2008 | Aram et al. |
| 7,388,972 B2 | 6/2008 | Kitson |
| 7,392,076 B2 | 6/2008 | De La Barrera |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,517,365 B2 | 4/2009 | Carignan et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,621,744 B2 | 11/2009 | Massoud |
| 7,621,920 B2 | 11/2009 | Claypool et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,641,663 B2 | 1/2010 | Hodorek |
| 7,643,862 B2 | 1/2010 | Schoenefeld |
| 7,658,741 B2 | 2/2010 | Claypool et al. |
| 7,682,398 B2 | 3/2010 | Croxton et al. |
| 7,693,321 B2 | 4/2010 | Lehtonen-Krause |
| 7,699,847 B2 | 4/2010 | Sheldon et al. |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,769,429 B2 | 8/2010 | Hu |
| 7,780,681 B2 | 8/2010 | Sarin et al. |
| 7,787,932 B2 | 8/2010 | Vilsmeier et al. |
| 7,794,467 B2 | 9/2010 | McGinley et al. |
| 7,796,791 B2 | 9/2010 | Tsougarakis et al. |
| 7,799,077 B2 | 9/2010 | Lang et al. |
| D626,234 S | 10/2010 | Otto et al. |
| 7,806,838 B2 | 10/2010 | Tsai et al. |
| 7,806,896 B1 | 10/2010 | Bonutti |
| 7,815,645 B2 | 10/2010 | Haines |
| 7,842,039 B2 | 11/2010 | Hodorek et al. |
| 7,842,092 B2 | 11/2010 | Otto et al. |
| 7,881,768 B2 | 2/2011 | Lang et al. |
| 7,894,650 B2 | 2/2011 | Weng et al. |
| 7,927,335 B2 | 4/2011 | Deffenbaugh et al. |
| 7,940,974 B2 | 5/2011 | Skinner et al. |
| 7,950,924 B2 | 5/2011 | Brajnovic |
| 7,963,968 B2 | 6/2011 | Dees, Jr. |
| D642,263 S | 7/2011 | Park |
| 7,974,677 B2 | 7/2011 | Mire et al. |
| D642,689 S | 8/2011 | Gannoe et al. |
| 8,007,448 B2 | 8/2011 | Moctezuma de La Barrera |
| 8,021,368 B2 | 9/2011 | Haines |
| 8,036,729 B2 | 10/2011 | Lang et al. |
| 8,052,623 B2 | 11/2011 | Haimerl et al. |
| 8,059,878 B2 | 11/2011 | Feilkas et al. |
| D651,315 S | 12/2011 | Bertoni et al. |
| 8,077,950 B2 | 12/2011 | Tsougarakis et al. |
| 8,086,336 B2 | 12/2011 | Christensen |
| D655,008 S | 2/2012 | Gannoe et al. |
| 8,126,234 B1 | 2/2012 | Edwards et al. |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,160,345 B2 | 4/2012 | Pavlovskaia et al. |
| 8,170,641 B2 | 5/2012 | Belcher |
| 8,177,850 B2 | 5/2012 | Rudan et al. |
| D661,808 S | 6/2012 | Kang |
| 8,202,324 B2 | 6/2012 | Meulink et al. |
| 8,214,016 B2 | 7/2012 | Lavallee et al. |
| 8,221,430 B2 | 7/2012 | Park et al. |
| 8,224,127 B2 | 7/2012 | Woodard et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,265,949 B2 | 9/2012 | Haddad |
| 8,306,601 B2 | 11/2012 | Lang et al. |
| 8,311,306 B2 | 11/2012 | Pavlovskaia et al. |
| D672,038 S | 12/2012 | Frey |
| 8,323,288 B2 | 12/2012 | Zajac |
| 8,331,634 B2 | 12/2012 | Barth et al. |
| 8,337,501 B2 | 12/2012 | Fitz et al. |
| 8,480,679 B2 | 7/2013 | Park |
| 8,483,469 B2 | 7/2013 | Pavlovskaia et al. |
| 2002/0087274 A1 | 7/2002 | Alexander et al. |
| 2002/0160337 A1 | 10/2002 | Klein et al. |
| 2003/0009167 A1 | 1/2003 | Wozencroft |
| 2003/0055502 A1 | 3/2003 | Lang et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0147927 A1 | 7/2004 | Tsougarakis et al. |
| 2004/0152970 A1 | 8/2004 | Hunter et al. |
| 2004/0153066 A1 | 8/2004 | Coon et al. |
| 2004/0153087 A1 | 8/2004 | Sanford et al. |
| 2004/0204760 A1 | 10/2004 | Fitz et al. |
| 2004/0220583 A1 | 11/2004 | Pieczynski, II et al. |
| 2004/0243148 A1 | 12/2004 | Wasielewski |
| 2004/0243481 A1 | 12/2004 | Bradbury et al. |
| 2005/0059978 A1 | 3/2005 | Sherry et al. |
| 2005/0065617 A1 | 3/2005 | De la Barrera et al. |
| 2005/0148843 A1 | 7/2005 | Roose |
| 2005/0148860 A1 | 7/2005 | Liew et al. |
| 2005/0192588 A1 | 9/2005 | Garcia |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2006/0015018 A1 | 1/2006 | Jutras et al. |
| 2006/0015030 A1 | 1/2006 | Poulin et al. |
| 2006/0015188 A1 | 1/2006 | Grimes |
| 2006/0036257 A1 | 2/2006 | Steffensmeier |
| 2006/0110017 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0195113 A1 | 8/2006 | Masini |
| 2006/0271058 A1 | 11/2006 | Ashton et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100462 A1 | 5/2007 | Lang et al. |
| 2007/0114370 A1 | 5/2007 | Smith et al. |
| 2007/0118055 A1 | 5/2007 | McCombs |
| 2007/0118243 A1 | 5/2007 | Schroeder et al. |

(56) References Cited

U.S. PATENT DOCUMENTS

| | | |
|---|---|---|
| 2007/0123912 A1 | 5/2007 | Carson |
| 2007/0162039 A1 | 7/2007 | Wozencroft |
| 2007/0167833 A1 | 7/2007 | Redel et al. |
| 2007/0173858 A1 | 7/2007 | Engh et al. |
| 2007/0191741 A1 | 8/2007 | Tsai et al. |
| 2007/0198022 A1 | 8/2007 | Lang et al. |
| 2007/0213738 A1 | 9/2007 | Martin et al. |
| 2007/0226986 A1 | 10/2007 | Park et al. |
| 2007/0232959 A1 | 10/2007 | Couture et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2007/0282451 A1 | 12/2007 | Metzger et al. |
| 2007/0288030 A1* | 12/2007 | Metzger et al. ................. 606/87 |
| 2007/0293734 A1 | 12/2007 | Coste-Maniere et al. |
| 2008/0004701 A1 | 1/2008 | Axelson et al. |
| 2008/0015433 A1 | 1/2008 | Alexander et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson et al. |
| 2008/0015606 A1 | 1/2008 | D'Alessio et al. |
| 2008/0015607 A1 | 1/2008 | D'Alessio et al. |
| 2008/0021299 A1 | 1/2008 | Meulink |
| 2008/0031412 A1 | 2/2008 | Lang et al. |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0147072 A1 | 6/2008 | Park et al. |
| 2008/0153067 A1 | 6/2008 | Berckmans et al. |
| 2008/0161815 A1 | 7/2008 | Schoenefeld et al. |
| 2008/0195108 A1 | 8/2008 | Bhatnagar et al. |
| 2008/0215059 A1 | 9/2008 | Carignan et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aaram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0157083 A1 | 6/2009 | Park et al. |
| 2009/0163923 A1 | 6/2009 | Flett et al. |
| 2009/0209884 A1 | 8/2009 | Van Vorhis et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0285465 A1 | 11/2009 | Haimerl et al. |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0099977 A1 | 4/2010 | Hershberger |
| 2010/0145344 A1 | 6/2010 | Jordan et al. |
| 2010/0152741 A1 | 6/2010 | Park et al. |
| 2010/0153076 A1 | 6/2010 | Bellettre et al. |
| 2010/0153081 A1 | 6/2010 | Bellettre et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0185202 A1 | 7/2010 | Lester et al. |
| 2010/0191242 A1 | 7/2010 | Massoud |
| 2010/0191244 A1 | 7/2010 | White et al. |
| 2010/0198351 A1 | 8/2010 | Meulink |
| 2010/0209868 A1 | 8/2010 | De Clerck |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0256479 A1 | 10/2010 | Park et al. |
| 2010/0262150 A1 | 10/2010 | Lian |
| 2010/0274253 A1 | 10/2010 | Ure |
| 2010/0274534 A1 | 10/2010 | Steines et al. |
| 2010/0292963 A1 | 11/2010 | Schroeder |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0324692 A1 | 12/2010 | Uthgenannt et al. |
| 2010/0329530 A1 | 12/2010 | Lang et al. |
| 2010/0332194 A1 | 12/2010 | McGuan et al. |
| 2011/0015636 A1 | 1/2011 | Katrana et al. |
| 2011/0016690 A1 | 1/2011 | Narainasamy et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0046735 A1 | 2/2011 | Metzger et al. |
| 2011/0054486 A1 | 3/2011 | Linder-Ganz et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092977 A1 | 4/2011 | Salehi et al. |
| 2011/0092978 A1 | 4/2011 | McCombs |
| 2011/0093108 A1 | 4/2011 | Ashby et al. |
| 2011/0106093 A1 | 5/2011 | Romano et al. |
| 2011/0112808 A1 | 5/2011 | Anderson et al. |
| 2011/0144760 A1 | 6/2011 | Wong et al. |
| 2011/0160736 A1 | 6/2011 | Meridew et al. |
| 2011/0166578 A1 | 7/2011 | Stone et al. |

(56) References Cited

U.S. PATENT DOCUMENTS

| | | |
|---|---|---|
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190899 A1 | 8/2011 | Pierce et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218542 A1 | 9/2011 | Lian |
| 2011/0218545 A1 | 9/2011 | Catanzarite et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0257653 A1 | 10/2011 | Hughes et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0295329 A1 | 12/2011 | Fitz et al. |
| 2011/0295378 A1 | 12/2011 | Bojarski et al. |
| 2011/0305379 A1 | 12/2011 | Mahfouz |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0004725 A1 | 1/2012 | Shterling et al. |
| 2012/0010711 A1 | 1/2012 | Antonyshyn et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0116203 A1 | 5/2012 | Vancraen et al. |
| 2012/0123420 A1 | 5/2012 | Honiball |
| 2012/0130382 A1 | 5/2012 | Iannotti et al. |
| 2012/0130434 A1 | 5/2012 | Stemniski |
| 2012/0143197 A1 | 6/2012 | Lang et al. |
| 2012/0143198 A1 | 6/2012 | Boyer et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165820 A1 | 6/2012 | De Smedt et al. |
| 2012/0165821 A1 | 6/2012 | Carignan et al. |
| 2012/0172882 A1 | 7/2012 | Sato |
| 2012/0179147 A1 | 7/2012 | Geebelen et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0203233 A1 | 8/2012 | Yoshida et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0230566 A1 | 9/2012 | Dean et al. |
| 2012/0230573 A1 | 9/2012 | Ito et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0239045 A1 | 9/2012 | Li |
| 2012/0265496 A1 | 10/2012 | Mahfouz |
| 2012/0265499 A1 | 10/2012 | Mahfouz et al. |
| 2012/0310400 A1 | 12/2012 | Park |
| 2013/0039551 A1 | 2/2013 | Pavlovskaia et al. |

FOREIGN PATENT DOCUMENTS

| | | |
|---|---|---|
| DE | 102005023028 A1 | 11/2006 |
| EP | 0097001 A | 12/1983 |
| EP | 0574098 A | 12/1993 |
| EP | 0622052 A | 11/1994 |
| EP | 0908836 A2 | 4/1999 |
| EP | 0908836 A3 | 12/1999 |
| EP | 1059153 A2 | 12/2000 |
| EP | 1486900 A1 | 12/2004 |
| EP | 1532939 A1 | 5/2005 |
| GB | 2215610 A1 | 9/1989 |
| GB | 2420717 A | 6/2006 |
| JP | 2001-092950 | 4/2001 |
| WO | WO 93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 01/00096 A1 | 1/2001 |
| WO | WO 01/70142 A1 | 9/2001 |
| WO | WO 01/85040 A1 | 11/2001 |
| WO | WO 02/096268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |

OTHER PUBLICATIONS

Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).

Advisory Action and Interview Summary, U.S. Appl. No. 12/390,667, mailed Apr. 27, 2012, 23 pages.

Amendment Under 37 C.F.R. 1.312, U.S. Appl. No. 12/386,105, filed Oct. 1, 2012, 6 pages.

Appeal Brief, U.S. Appl. No. 12/390,667, filed Jul. 12, 2012, 32 pages.

Appeal Brief, U.S. Appl. No. 12/391,008, filed Oct. 16, 2012, 24 pages.

Final Office Action, U.S. Appl. No. 12/390,667, mailed Jan. 13, 2012, 27 pages.

Final Office Action, U.S. Appl. No. 11/641,382, mailed Jul. 25, 2012, 12 pages.

Final Office Action, U.S. Appl. No. 11/641,569, mailed Mar. 1, 2012, 12 pages.

Final Office Action, U.S. Appl. No. 11/924,425, mailed Jul. 6, 2012, 14 pages.

Final Office Action, U.S. Appl. No. 11/946,002, mailed May 9, 2012, 24 pages.

Final Office Action, U.S. Appl. No. 12/391,008, mailed May 17, 2012, 28 pages.

Non-Final Office Action, U.S. Appl. No. 11/924,425, mailed Jan. 25, 2012, 35 pages.

Non-Final Office Action, U.S. Appl. No. 11/641,382, mailed Mar. 29, 2012, 24 pages.

Non-Final Office Action, U.S. Appl. No. 11/946,002, dated Nov. 25, 2011, 44 pages.

(56) References Cited

OTHER PUBLICATIONS

Non-Final Office Action, U.S. Appl. No. 12/111,924, mailed Jun. 29, 2012, 35 pages.
Non-Final Office Action, U.S. Appl. No. 12/386,105, dated Feb. 9, 2012, 30 pages.
Non-Final Office Action, U.S. Appl. No. 12/390,667, mailed Sep. 26, 2012, 21 pages.
Non-Final Office Action, U.S. Appl. No. 12/391,008, mailed Oct. 31, 2011, 44 pages.
Non-Final Office Action, U.S. Appl. No. 12/546,545, mailed Jul. 19, 2012, 28 pages.
Non-Final Office Action, U.S. Appl. No. 12/563,809, mailed Sep. 21, 2012, 32 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Notice of Allowance, U.S. Appl. No. 11/641,382, mailed Oct. 9, 2012, 9 pages.
Notice of Allowance, U.S. Appl. No. 11/924,425, mailed Sep. 25, 2012, 18 pages.
Notice of Allowance, U.S. Appl. No. 11/959,344, mailed Mar. 5, 2012, 13 pages.
Notice of Allowance, U.S. Appl. No. 12/386,105, mailed Jul. 5, 2012, 11 pages.
Notice of Allowance, U.S. Appl. No. 13/374,960, mailed Nov. 2, 2012, 24 pages.
Office Action (Restriction Requirement), U.S. Appl. No. 12/563,809, dated Feb. 2, 2012, 7 pages.
RCE/Amendment, U.S. Appl. No. 11/946,002, filed Sep. 6, 2012, 38 pages.
Response to Final Office Action, U.S. Appl. No. 11/641,569, filed Jun. 28, 2012, 10 pages.
Response to Final Office Action, U.S. Appl. No. 11/641,382, filed Sep. 24, 2012, 11 pages.
Response to Final Office Action, U.S. Appl. No. 11/959,344, filed Dec. 27, 2011, 16 pages.
Response to Final Office Action, U.S. Appl. No. 11/924,425, filed Sep. 5, 2012, 9 pages.
Response to Final Office Action, U.S. Appl. No. 12/390,667, filed Mar. 12, 2012, 19 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/563,809, filed Aug. 6, 2012, 10 pages.
Response to Restriction, U.S. Appl. No. 11/924,425, filed Nov. 8, 2011, 5 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Restriction Requirement, U.S. Appl. No. 12/111,924, mailed Mar. 19, 2012, 8 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/563,809, mailed Jul. 6, 2012, 6 pages.
Restriction Requirement, U.S. Appl. No. 12/636,939, mailed Apr. 13, 2012, 6 pages.
Advisory Action, U.S. Appl. No. 11/642,385, dated Oct. 29, 2010, 3 pages.
Amendment and Response to *Ex Parte Quayle* Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Office Action and Petition to Revive, U.S. Appl. No. 10/146,862, filed Jan. 18, 2006, 29 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
European Search Report, 10192631.9-2310, dated Mar. 17, 2011, 5 pages.
*Ex Parte Quayle* Action, U.S. Appl. No. 29/296,687, mailed Jan. 24, 2011, 11 pages.
Final Office Action, U.S. Appl. No. 11/641,569, mailed Aug. 5, 2010, 13 pages.
Final Office Action, U.S. Appl. No. 11/656,323, mailed Sep. 3, 2010, 11 pages.
Final Office Action, U.S. Appl. No. 11/641,569, mailed May 10, 2010, 9 pages.
International Search Report and Written Opinion, International Application No. PCT/US2009/034983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
International Search Report and Written Opinion, International Application No. PCT/US2009/040629, mailed Aug. 6, 2009, 10 pages.
International Search Report and Written Opinion, International Application No. PCT/US2009/051109, mailed Nov. 6, 2009, 13 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.

(56) References Cited

OTHER PUBLICATIONS

International Search Report and Written Opinion, PCT/US2007/001624, dated Dec. 12, 2007, 14 pages.
International Search Report and Written Opinion, PCT/US2007/001622, dated Jun. 11, 2007, 14 pages.
International Search Report and Written Opinion, PCT/US2008/083125, dated Mar. 9, 2009, 13 pages.
Invitation to Pay Additional Fees mailed on Jul. 31, 2007, for PCT Application No. PCT/US2007/001624 filed on Jan. 19, 2007, 5 pages.
Non-Final Office Action, U.S. Appl. No. 11/641,569, mailed Jan. 20, 2010, 12 pages.
NonFinal Office Action, U.S. Appl. No. 11/642,385, mailed Mar. 2, 2010, 11 pages.
Non-Final Office Action, U.S. Appl. No. 11/656,323, mailed Mar. 30, 2010, 10 pages.
NonFinal Office Action, U.S. Appl. No. 11/641,569, mailed Nov. 12, 2009, 9 pages.
Nonfinal Office Action, U.S. Appl. No. 11/959,344, dated Feb. 15, 2011, 29 pages.
Notice of Allowance, U.S. Appl. No. 29/296,687, mailed Mar. 31, 2011, 18 pages.
Notice of Non-Compliant Amendment, U.S. Appl. No. 11/641,569, mailed Aug. 7, 2009, 3 pages.
Office Action, U.S. Appl. No. 10/146,862, mailed Jan. 13, 2005, 10 pages.
Preliminary Amendment, U.S. Appl. No. 11/641,669, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010, 18 pages.
RCE/Amendment, U.S. Appl. No. 11/642,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/959,344, filed Nov. 24, 2010, 13 pages.
Restriction Requirement, U.S. Appl. No. 11/641,382, mailed Sep. 3, 2009, 6 pages.
Restriction Requirement, U.S. Appl. No. 11/641,569, mailed Apr. 27, 2009, 7 pages.
Restriction Requirement, U.S. Appl. No. 11/642,385, mailed Oct. 27, 2009, 7 pages.
Restriction Requirement, U.S. Appl. No. 11/656,323, mailed Nov. 13, 2009, 10 pages.
Restriction Requirement, U.S. Appl. No. 11/959,344, dated Oct. 29, 2010, 6 pages.
Restriction Requirement, U.S. Appl. No. 29/296,687, mailed Sep. 21, 2010, 7 pages.
AKCA, "Matching of 3D Surfaces and Their Intensities," ISPRS Journal of Photogrammetry & Remote Sensing, 62(2007), 112-121.
Akenine-Möller et al., *Real-Time Rendering, Second Edition*, AK Peters, Natick, MA, 6 pages. (Table of Contents), 2002.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.
Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.
Barequet et al., "Filling Gaps in the Boundary of a Polyhedron," *Computer Aided Geometric Design*, vol. 12, pp. 207-229, 1995.
Barequet et al., "Repairing CAD Models," Proceedings of the 8th IEEE Visualization '97 Conference, pp. 363-370, Oct. 1997.
Bargar et al., "Robotic Systems in Surgery," Orthopedic and Spine Surgery, Surgical Technology International II, 1993, 419-423.
Berry et al., "Personalised image-based templates for intra-operative guidance," *Proc. Inst. Mech. Eng. Part H: J. Engineering in Medicine*, vol. 219, pp. 111-118, Oct. 7, 2004.
Besl et al., "A Method for Registration of 3-D Shapes," IEEE Transactions on Pattern Analysis and Machine Intelligence (PAMI), 14(2):239-256, Feb. 1992.
Biščević et al., "Variations of Femoral Condyle Shape," *Coll. Antropol.*, vol. 29 No. 2, pp. 409-414, 2005.
Blaha et al., "Using the Transepicondylar Axis to Define the Sagittal Morphology of the Distal Part of the Femur," J Bone Joint Surg Am. 2002;84-A Suppl 2:48-55.
Blinn, *Jim Blinn's Corner—A Trip Down the Graphics Pipeline*, Morgan Kaufmann Publishers, Inc., San Francisco, CA, 5 pages (Table of Contents), 1996.
Bøhn et al., "A Topology-Based Approach for Shell-Closure," *Geometric Modeling for Product Realization*(P.R. Wilson et al. editors), pp. 297-319, Elsevier Science Publishers B.V., North-Holland, 1993.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Chauhan et al., "Computer-assisted knee arthroplasty *versus* a conventional jig-based technique—a randomised, prospective trial," *The Journal of Bone and Joint Surgery*, vol. 86-B, No. 3, pp. 372-377, Apr. 2004.
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Cohen et al., *Radiosity and Realistic Image Synthesis*, Academic Press Professional, Cambridge, MA, 8 pages (Table of Contents), 1993.
Couglin et al., "Tibial Axis and Patellar Position Relative to the Femoral Epicondylar Axis During Squatting," *The Journal of Arthroplasty*, vol. 18, No. 8, Elsevier, 2003.
Delp et al., "Computer Assisted Knee Replacement," *Clinical Orthopaedics and Related Research*, No. 354, pp. 49-56, Sep. 1998.
Dutré et al., *Advanced Global Illumination*, AK Peters, Natick, MA, 5 pages (Table of Contents), 2003.
Eckhoff et al., "Difference Between the Epicondylar and Cylindrical Axis of the Knee," Clin Orthop Relat Res. 2007;461:238-44.
Eckhoff et al., "Three-Dimensional Mechanics, Kinematics, and Morphology of the Knee Viewed in Virtual Realty," *The Journal of Bone and Joint Surgery*, vol. 87-A, Supplement 2, pp. 71-80, 2005.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).

(56) References Cited

OTHER PUBLICATIONS

Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clin orthop Relat Res. 1990(260):98-103.
Erikson, "Error Correction of a Large Architectural Model: The Henderson County Courthouse," Technical Report TR95-013, Dept. of Computer Science, University of North Carolina at Chapel Hill, pp. 1-11, 1995.
Ervin et al., *Landscape Modeling*, McGraw-Hill, New York, NY, 8 pages (Table of Contents), 2001.
Farin, *NURB Curves and Surfaces: From Projective Geometry to Practical Use*, AK Peters, Wellesley, MA, 7 pages (Table of Contents), 1995.
Favorito et al., "total Knee Arthroplasty in the Valgus Knee," Journal Am Acad Orthop surg. 2002;10(1):16-24.
Fleischer et al., "Accurate Polygon Scan Conversion Using Half-Open Intervals," *Graphics Gems III*, pp. 362-365, code: pp. 599-605, 1992.
Foley et al., *Computer Graphics: Principles and Practice*, Addison-Wesley Publishing Company, Reading, MA, 9 pages (Table of Contents), 1990.
Freeman et al., "The Movement of the Knee Studied by Magnetic Resonance Imaging," Clinical orthop Relat Res. 2003(410):35-43.
Freeman et al., "The movement of the Normal Tibio-Femoral Joint," Journal Biomech. 2005;38(2):197-208.
Glassner (editor), *An Introduction to Ray Tracing*, Academic Press Limited, San Diego, CA, 4 pages (Table of Contents), 1989.
Glassner, *Principles of Digital Image Synthesis*, vols. One and Two, Morgan Kaufmann Publishers, Inc., San Francisco, CA, 32 pages (Table of Contents), 1995.
Gooch et al., *Non-Photorealistic Rendering*, AK Peters, Natick, MA, 4 pages (Table of Contents), 2001.
Graichen et al., "quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "least Squares 3D Surface and Curve Matching," ISPRS Journal of Photogrammetry & Remote Sensing, 59(2005), 151-174.
Grüne et al., "On numerical algorithm and interactive visualization for optimal control problems," *Journal of Computation and Visualization in Science*, vol. 1, No. 4, pp. 221-229, Jul. 1999.
Guéziec et al., "Converting Sets of Polygons to Manifold Surfaces by Cutting and Stitching," Proc. IEEE Visualization 1998, pp. 383-390, Oct. 1998.
Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: Fact and Fiction Syllabus, San Diego, CA, 8 pages, Oct. 20-22, 2005 (best available copy).
Hafez et al., "Computer Assisted Total Knee Replacement: Could a Two-Piece Custom Template Replace the Complex Conventional Instrumentations?", *Computer Aided Surgery*, vol. 9, No. 3, pp. 93-94, 2004.
Hafez et al., "Computer-Assisted Total Knee Arthroplasty Using Patient-Specific Templating," *Clinical Orthopaedics and Related Research*, No. 0, pp. 1-9, 2006.
Hollister et al, "The Axes of Rotation of the Knee," Clin Orthop Relat Res. 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.

Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jensen, *Realistic Image Synthesis Using Photon Mapping*, AK Peters, Natick, MA, 7 pages (Table of Contents), 2001.
Jacobs et al, "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Jones et al., "A new approach to the construction of surfaces from contour data," *Computer Graphics Forum*, vol. 13, No. 3, pp. 75-84, 1994 [ISSN 0167-7055].
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Khorramabadi, "A Walk Through the Planned CS Building," Technical Report UCB/CSD 91/652, Computer Science Department, University of California at Berkeley, 74 pages, 1991.
Kidder et al., "3-D Model Acquisition, Design, Planning and Manufacturing of Orthopaedic Devices: A Framework," *Advanced Sensor and Control-System Interface* (B.O. Nnaji editor), Proceedings SPIE—The International Society for Optical Engineering, Bellingham, WA, vol. 2911, pp. 9-22, Nov. 21-22, 1996.
Kienzel III et al., "Total Knee Replacement," IEEE May/Jun. 1995.
Kienzel III et al., "An Integrated CAD-Robotics System for Total Knee Replacement Surgery", IEEE International Conference, pp. 889-894, vol. 1, May 1993.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.
Kunz et al., "Computer Assisted Hip Resurfacing Using Individualized Drill Templates," *The Journal of Arthroplasty*, vol. 00, No. 0, pp. 1-7, 2009.
Lea et al., "Registration and immobilization in robot-assisted surgery", Journal of Image Guided Surgery, pp. 1-10, 1995.
Lorensen et al., "Marching Cubes: A High Resolution 3d Surface Construction Algorithm," *Computer Graphics*, vol. 21, No. 4, pp. 163-169, 1987.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Determination of the Tibia Based on 2d Radiographs Using A 2d/3d Database", Dept. of Surgery, Trauma Unit, University Hospital, Bassel, Switzerland, *Computer Aided Surgery*6:183-194 (2001).
Mihalko et al., The Variability of Intramedullary Alignment of the Femoral Component During Total Knee Arthroplasty, Journal Arthroplasty. 2005;20(1):25-8.
Morvan et al., IVECs, Interactively Correcting .STL Files in a Virtual Environment, Clemson University, Clemson, SC, Proc. Conf. Virtual Design, Aug. 1996.

(56) References Cited

OTHER PUBLICATIONS

Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Platt et al., "Mould Arthroplasty of the Knee, A Ten-Year Follow-up Study," *The Journal of Bone and Joint Surgery* (British Volume) vol. 51-B, No. 1, pp. 76-87, Feb. 1969.
Potter, "Arthroplasty of the Knee with Tibial Metallic Implants of the McKeever and MacIntosh Design," *The Surgical Clinics of North America*, vol. 49, pp. 903-915, Aug. 1969.
Radermacher et al., "Computer Assisted Orthopaedic Surgery with Image Based Individual Templates," *Clinical Orthopaedics and Related Research*, vol. 354, pp. 28-38, Sep. 1998.
Rohlfing et al., "*Quo Vadis*, Atlas-Based Segmentation?", *The Handbook of Medical Image Anaylsis: Segmentation and Registration Models* (Kluwer), pp. 1-55, (http:www.stanford.edu/~rohlfing/publications/2005-rohlfing-chapter-quovadisatlasbasedsegmentation.pdf).
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Shirley et al., *Realistic Ray Tracing*, Second Edition, AK Peters, Natick, MA, 7 pages (Table of Contents), 2003.
Siston et al., "The Variability of Femoral Rotational Alignment in Total Knee Arthroplasty," Journal Bone Joint Surg Am. 2005;87(10):2276-80.
Siston et al., "Averaging Different Alignment Axes Improves Femoral Rotational Alignment in Computer-Navigated Total Knee Arthroplasty," Journal Bone Joint Surg Am. 2008;90(10):2098-104.
Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Strothotte et al., *Non-Photorealistic Computer Graphics—Modeling, Rendering, and Animation*, Morgan Kaufmann Publishers, San Francisco, CA, 9 pages (Table of Contents), 2002.
Stulberg et al., "Computer-and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Vande Berg et al., "Assessment of Knee Cartilage in Cadavers with Dual-Detector Spiral CT Arthrography and MR Imaging," *Radiology*, vol. 222, No. 2, pp. 430-436, Feb. 2002.
Wright Medical Technology, Inc., "Prophecy Pre-Operative Naviation Guides Surgical Technique," 2009.
Wikipedia, the Free Encyclopedia, "CNC," (date unknown) located at http://en.wikipedia.org/wiki/CNC>, 6 pages, last visited on Apr. 12, 2007.
U.S. Appl. No. 10/146,862, filed May 15, 2002, Park et al.
U.S. Appl. No. 29/296,687, filed Oct. 25, 2007, Park.
U.S. Appl. No. 13/066,568, filed Apr. 18, 2011, Pavlovskaia et al.
U.S. Appl. No. 29/394,882, filed Jun. 22, 2011, Park.
Amendment and Response to Non-Final Office Action, U.S. Appl. No. 11/959,344, dated Jul. 15, 2011, 13 pages.
Final Office Action, U.S. Appl. No. 11/959,344, mailed Oct. 27, 2011, 12 pages.
International Search Report and Written Opinion, PCT/US2011/032342, dated Jul. 1, 2011, 8 pages.
Non-Final Office Action, U.S. Appl. No. 11/641,569, dated Aug. 3, 2011, 14 pages.
Non-Final Office Action, U.S. Appl. No. 12/390,667, dated Aug. 24, 2011, 49 pages.
Notice of Allowance, U.S. Appl. No. 13/066,568, mailed Oct. 26, 2011, 28 pages.
Response to Restriction Requirement, U.S. Appl. No. 12/390,667, dated Jul. 27, 2011, 8 pages.
Response to Restriction Requirement, U.S. Appl. No. 12/391,008, filed Aug. 29, 2011, 9 pages.
Response to Restriction, U.S. Appl. No. 11/946,002, filed Sep. 23, 2011, 7 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 12/386,105, dated Oct. 24, 2011, 7 pages.
Restriction Requirement, U.S. Appl. No. 12/390,667, dated Jul. 14, 2011, 9 pages.
Restriction Requirement, U.S. Appl. No. 12/391,008, dated Aug. 18, 2011, 6 pages.
U.S. Appl. No. 13/488,505, filed Jun. 5, 2012, Ilwhan Park et al.
U.S. Appl. No. 13/573,662, filed Oct. 2, 2012, Pavlovskaia et al.
U.S. Appl. No. 13/723,904, filed Dec. 21, 2012, Park.
U.S. Appl. No. 13/730,467, filed Dec. 28, 2012, Park et al.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
U.S. Appl. No. 13/749,095, filed Jan. 24, 2013, Song.
Examiner's Answer in appeal, U.S. Appl. No. 12/391,008, mailed Dec. 13, 2012, 27 pages.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Final Office Action, U.S. Appl. No. 12/563,809, mailed Mar. 7, 2013, 14 pages.
Non-Final Office Action, U.S. Appl. No. 11/641,569, dated Jan. 3, 2013, 12 pages.
Non-Final Office Action, U.S. Appl. No. 12/546,545, mailed Mar. 13, 2013, 10 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 29/394,882, mailed Feb. 4, 2013, 32 pages.
Notice of Allowance, U.S. Appl. No. 12/111,924, mailed Mar. 11, 2013, 14 pages.
Notice of Allowance, U.S. Appl. No. 13/374,960, mailed May 6, 2013, 20 pages.

(56) References Cited

OTHER PUBLICATIONS

Notice of Allowance, U.S. Appl. No. 13/573,662, mailed Mar. 19, 2013, 34 pages.
Response to Final Office Action, U.S. Appl. No. 12/546,545, filed Feb. 20, 2013, 13 pages.
Response to Final Office Action, U.S. Appl. No. 12/563,809, filed May 6, 2013, 15 pages.
Response to Final Office Action, U.S. Appl. No. 12/636,939, filed Apr. 8, 2013, 10 pages.
Response to Non-Final Office Action, U.S. Appl. No. 12/390,667, filed Feb. 26, 2013, 36 pages.
Response to Non-Final Office Action, U.S. Appl. No. 12/563,809, filed Dec. 13, 2012, 15 pages.
Response to Non-Final Office Action, U.S. Appl. No. 11/641,569, filed Apr. 3, 2013, 9 pages.
Response to Restriction Requirement, U.S. Appl. No. 12/760,388, filed Apr. 5, 2013, 7 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
Restriction Requirement, U.S. Appl. No. 12/760,388, mailed Mar. 6, 2013, 7 pages.
U.S. Appl. No. 13/923,093, filed Jun. 20, 2013, Park.
Amendment Under 37 C.F.R. 1.312, U.S. Appl. No. 13/374,960, filed May 7, 2013, 6 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/636,939, mailed Apr. 25, 2013, 16 pages.
Non-Final Office Action, U.S. Appl. No. 13/730,585, mailed Jun. 11, 2013, 10 pages.
Non-Final Office Action, U.S. Appl. No. 12/760,388, mailed Jun. 20, 2013, 54 pages.
Notice of Allowance, U.S. Appl. No. 12/563,809, mailed May 28, 2013, 11 pages.
Preliminary Amendment, U.S. Appl. No. 13/731,697, filed May 10, 2013, 6 pages.
Non-Final Office Action, U.S. Appl. No. 11/641,569, mailed Jul. 12, 2013, 21 pages.
Non-Final Office Action, U.S. Appl. No. 13/723,904, mailed Aug. 9, 2013, 6 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.

* cited by examiner

PREOPERATIVELY PLANNING AN ARTHROPLASTY PROCEDURE AND GENERATING A CORRESPONDING PATIENT SPECIFIC ARTHROPLASTY RESECTION GUIDE

CROSS REFERENCE TO RELATED APPLICATIONS

The present application is a continuation-in-part ("CIP") of U.S. patent application Ser. No. 12/760,388 ("the '388 application"), which was filed Apr. 14, 2010 and titled "Preoperatively Planning an Arthroplasty Procedure and Generating a Corresponding Patient Specific Arthroplasty Resection Guide". The '388 application is a CIP application of U.S. patent application Ser. No. 12/563,809 filed on Sep. 21, 2009 and titled "Arthroplasty System and Related Methods", which claims priority to U.S. patent application 61/102,692 ("the '692 application") filed Oct. 3, 2008 and titled "Arthroplasty System and Related Methods". The '388 application is also a CIP application of U.S. patent application Ser. No. 12/546,545 filed on Aug. 24, 2009 and titled "Arthroplasty System and Related Methods", which claims priority to the '692 application. The '388 application is also a CIP application of U.S. patent application Ser. No. 11/959,344, which was filed Dec. 18, 2007 and titled "System and Method for Manufacturing Arthroplasty Jigs". The '388 application is also CIP application of U.S. patent application Ser. No. 12/111,924 ("the '924 application"), which was filed Apr. 29, 2008 and titled "Generation of a Computerized Bone Model Representative of a Pre-Degenerated State and Useable in the Design and Manufacture of Arthroplasty Devices". The '388 application is also a CIP application of U.S. patent application Ser. No. 12/505,056 ("the '056 application"), which was filed Jul. 17, 2009 and titled "System and Method for Manufacturing Arthroplasty Jigs Having Improved Mating Accuracy". The '056 application claims priority to U.S. patent application 61/083,053 filed Jul. 23, 2008 and titled "System and Method for Manufacturing Arthroplasty Jigs Having Improved Mating Accuracy". The present application claims priority to all of the above mentioned applications and hereby incorporates by reference all of the above-mentioned applications in their entireties into the present application.

FIELD OF THE INVENTION

The present invention relates to systems and methods for manufacturing customized arthroplasty cutting jigs. More specifically, the present invention relates to automated systems and methods of manufacturing such jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state.

It is believed that it is best for the vast majority of patients to have the patient's joint restored to its pre-deteriorated state (i.e., natural (i.e., kinematic) alignment). However, for some patient's, it may not be possible or desirable to restore the patient's joint to it natural (i.e., kinematic) alignment. For example, a physician may determine that the patient's joint assume a zero degree mechanical axis alignment or an alignment between the zero degree mechanical axis alignment and the natural (i.e., kinematic) alignment.

There is a need in the art for a system and method capable of generating customized arthroplasty jigs configured for a variety of alignment results. There is also a need in the art for a system and method capable of communicating joint alignment information to a physician and incorporating into the jig design the physician's input regarding the alignment information.

SUMMARY

Various embodiments of a method of manufacturing a custom arthroplasty resection guide or jig are disclosed herein. In a first embodiment, the method may include: generate MRI knee coil two dimensional images, wherein the knee coil images include a knee region of a patient; generate MRI body coil two dimensional images, wherein the body coil images include a hip region of the patient, the knee region of the patient and an ankle region of the patient; in the knee coil images, identify first locations of knee landmarks; in the body coil images, identify second locations of the knee landmarks; run a transformation with the first and second locations, causing the knee coil images and body coil images to generally correspond with each other with respect to location and orientation.

In a second embodiment, the method may include: preoperatively plan in a three dimensional computer environment a proposed post surgical joint geometry for a joint, wherein the proposed post surgical joint geometry is a natural (i.e., kinematic) alignment joint geometry that is generally representative of the joint prior to degeneration; provide a two dimensional coronal view of the proposed post surgical joint geometry to a physician; employ feedback received from the physician regarding the two dimensional coronal view to arrive at a finalized post surgical joint geometry that is at least one of: a) the natural alignment joint geometry; b) a zero degree mechanical axis alignment joint geometry, or somewhere between a) and b).

In a third embodiment, the method may include: a) identify in a computer environment hip, knee and ankle centers in a first set of two dimensional images; b) generate in a computer environment a three dimensional knee model from a second set of two dimensional images; c) cause the three dimensional knee model and hip, knee and ankle centers to be positioned relative to each other in a global coordinate system generally as if the three dimensional knee model were generated from the first set of two dimensional images; d) preoperatively plan an arthroplasty procedure with the three dimensional knee model of step c); and e) at least one of maintain or reestablish the positional relationship established in step c) between the three dimensional knee model and the hip, knee and ankle centers to address any positional changes in the global coordinate system for the three dimensional knee model during the preoperatively planning of step d).

In a fourth embodiment, the method may include: a) generating a three dimensional femur bone model from MRI knee coil two dimensional images, wherein the knee coil images include a knee region of a patient; b) identifying a hip center and a femur knee center in MRI body coil two dimensional images, wherein the body coil images include a hip region of the patient and the knee region of the patient; c) causing the three dimensional femur bone model and hip center and femur knee center to generally correspond with each other with respect to location and orientation; d) defining relative to the three dimensional femur bone model a femoral mechanical axis via the femur knee center and the hip center; e) identifying a most distal condylar point of the three dimensional femur bone model; f) defining a distal plane that is orthogonal to the femoral mechanical axis in a coronal view of the three dimensional femur bone model, wherein the distal plane also passes through the most distal condylar point; g) and defining a resection plane that is parallel to the distal plane and proximally offset from the distal plane; and h) using data associated with the resection plane to define a resection guide in the custom arthroplasty resection guide.

In a fifth embodiment, the method may include: a) generating a three dimensional tibia bone model from MRI knee coil two dimensional images, wherein the knee coil images include a knee region of a patient; b) identifying an ankle center and a tibia knee center in MRI body coil two dimensional images, wherein the body coil images include an ankle region of the patient and the knee region of the patient; c) causing the three dimensional tibia bone model and ankle center and tibia knee center to generally correspond with each other with respect to location and orientation; d) defining relative to the three dimensional tibia bone model a tibial mechanical axis via the tibia knee center and the ankle center; e) identifying a condylar point of the three dimensional tibia bone model; f) defining a proximal plane that is orthogonal to the tibial mechanical axis in a coronal view of the three dimensional tibia bone model, wherein the proximal plane also passes through a condylar point; g) defining a resection plane that is parallel to the proximal plane and distally offset from the proximal plane; and h) using data associated with the resection plane to define a resection guide in the custom arthroplasty resection guide.

In a sixth embodiment, the method may include: a) identify in a computer environment hip, knee and ankle centers in a first set of two dimensional images; b) generate in a computer environment a three dimensional knee model from a second set of two dimensional images; c) cause the three dimensional knee model and hip, knee and ankle centers to be positioned relative to each other in a global coordinate system generally as if the three dimensional knee model were generated from the first set of two dimensional images; d) preoperatively plan an arthroplasty procedure with the three dimensional knee model of step c) via a method including: i) defining a mechanical axis relative to the three dimensional knee model via a pair of points including the knee center and at least one of the hip center or ankle center; and ii) defining a resection plane parallel to, and offset from, a reference plane that: 1) is orthogonal to the mechanical axis in a coronal view and 2) extends through a condylar point on the three dimensional knee model; and e) using data associated with the resection plane to define a resection guide in the custom arthroplasty resection guide.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. Patent Applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. Pat. No. 11/642,385 to Park et al., titled "Arthroplasty Devices and Related Methods" and filed Dec. 19, 2006. The disclosures of these three U.S. Patent Applications are incorporated by reference in their entireties into this Detailed Description.

The methods and systems disclosed herein allow a resulting jig 2 to generate surgical resections that allow implanted arthroplasty prosthetic femoral and tibial joint components to achieve a joint alignment that is: (1) generally representative of the patient's pre-degenerative joint line; generally corresponding to a zero mechanical axis alignment; or (3) somewhere between (1) and (2). Whether the resections result in a joint alignment that is (1), (2) or somewhere between (1) and (2) may be a result of physician input and modification of the natural (i.e., kinematic) joint alignment calculated during preoperative planning ("POP").

Figure 4:
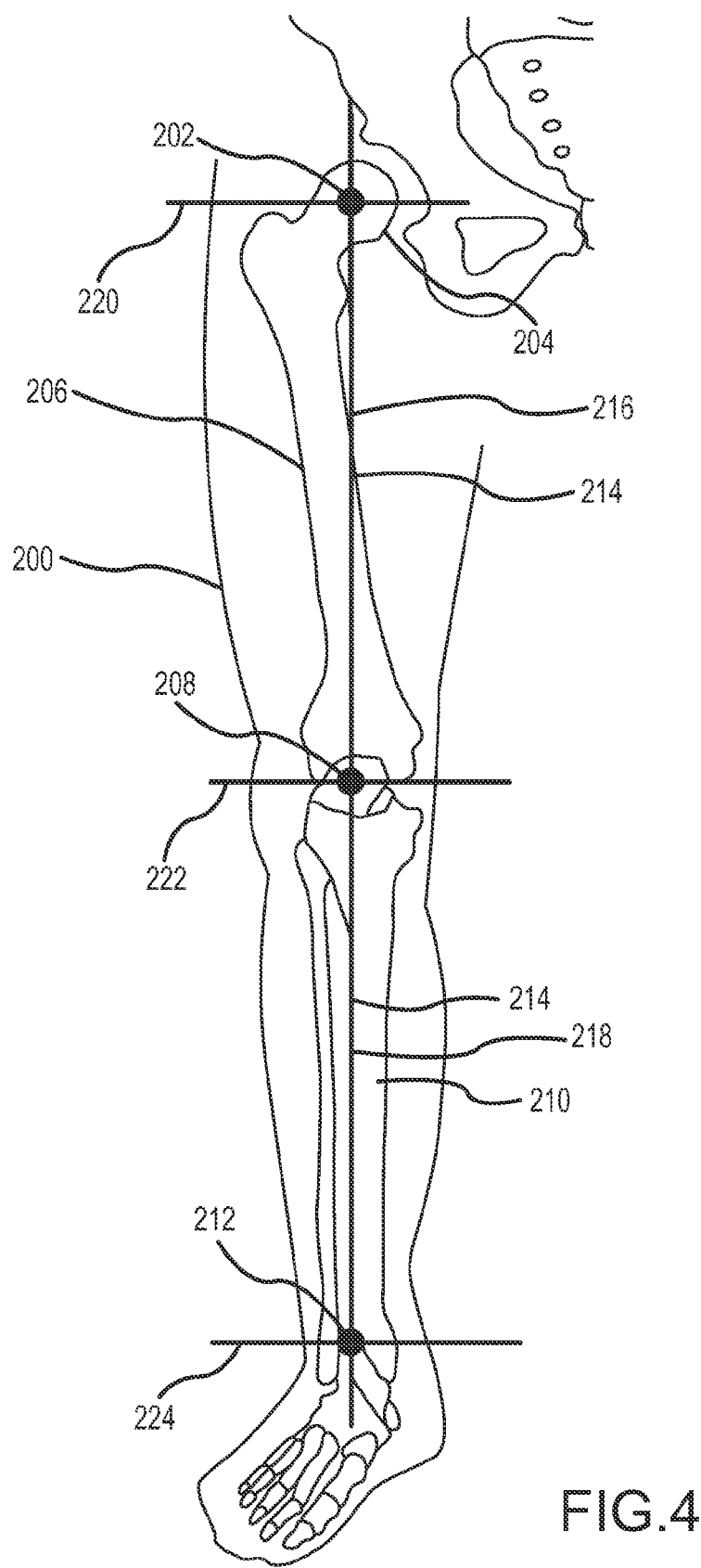
FIG. 4 is a coronal view of a patient's leg having a zero-degree mechanical axis knee joint geometry.

As can be understood from FIG. 4, which is a coronal view of a patient's leg 200, in zero-degree mechanical axis theory, the center of the hip 202 (located at the head 204 of the femur 206), the center of the knee 208 (located at the notch where the intercondylar tubercle of the tibia 210 meets the femur 206), and the center of ankle 212 form a straight line which defines the mechanical axis ("MA") 214 of the leg skeletal structure. As a result, the femoral mechanical axis ("FMA") 216, which extends from the hip center 202 to the knee center 208, is coextensively aligned with the MA 214. Similarly, the tibial mechanical axis (TMA") 218, which extends from the knee center 208 to the ankle center 212, is coextensively aligned with the MA 214. When the patient's leg 200 is standing in full extension and viewed from the front, the MA 214, FMA 216 and TMA 218 are perpendicular to the hip center axis 220, the knee joint line axis 222, and the ankle center axis 224.

Figure 5:
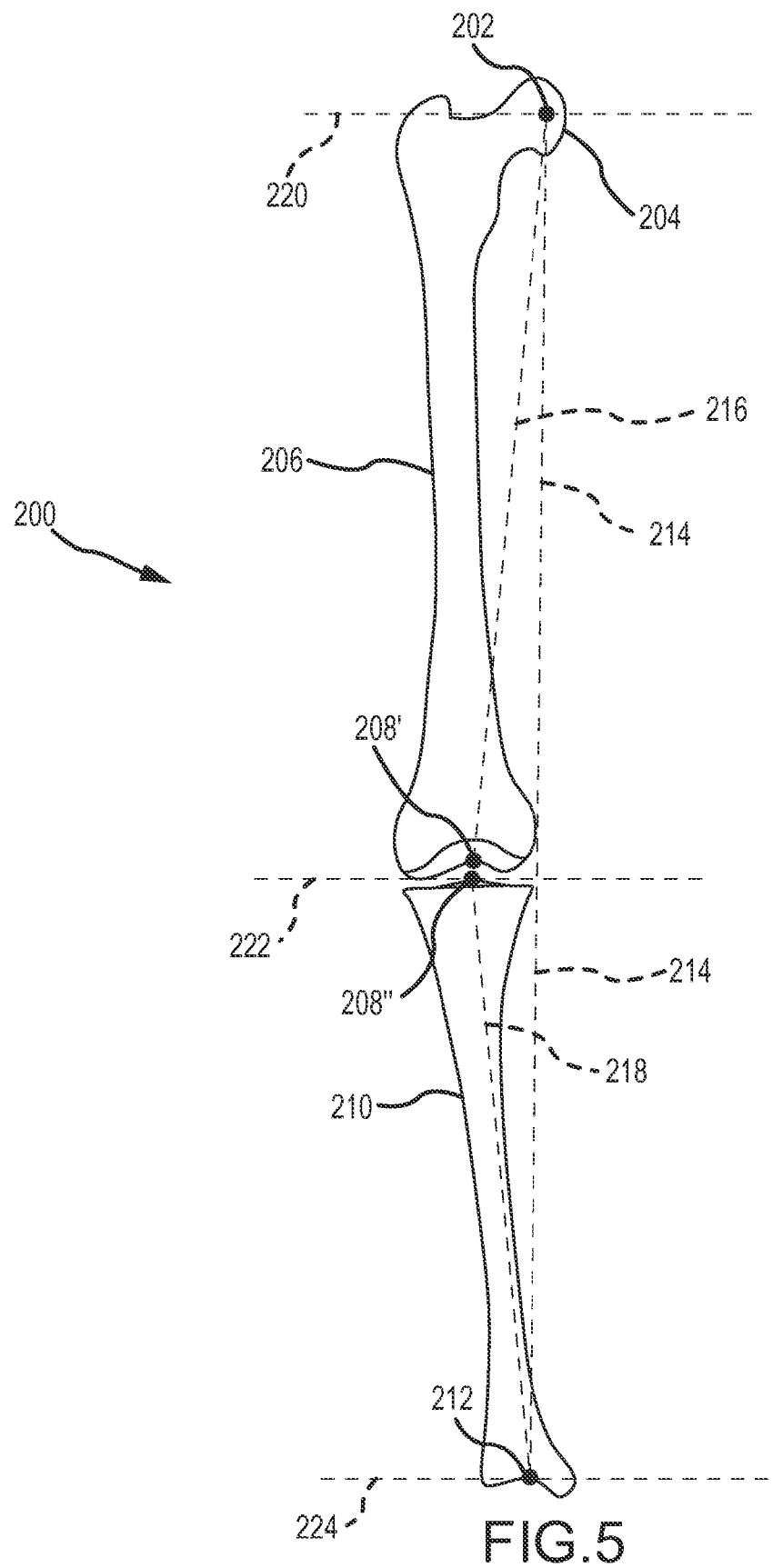
FIG. 5 is a coronal view of a patient's leg having a varus knee joint geometry.

In reality, only approximately two percent of the human population has the zero-degree mechanical axis ("neutral") leg skeletal structure depicted in FIG. 4. The other approximately 98 percent of the human population has a leg skeletal structure that is slightly varus (bow legged), as depicted in FIG. 5, or slightly valgus (knocked knee). Thus, for such varus or valgus leg skeletal structures, the FMA 214 and TMA 216 will not be coextensively aligned with the MA 214 or perpendicular to the knee joint line axis 222.

A knee arthroplasty procedure may be considered a natural alignment or kinematic alignment procedure when the knee arthroplasty procedure is preoperatively planned such that the prosthetic knee implants implanted during the knee arthroplasty procedure generally return the patient's knee geometry to the geometry that existed before the patient's knee geometry was impacted via deterioration of the knee joint. For example, if the patient's pre-deteriorated knee geometry was varus, such as depicted in FIG. 5, then the knee arthroplasty procedure is preoperatively planned such that the implanted prosthetic knee implants result in a knee geometry that is generally the same extent varus. Similarly, if the patient's pre-deteriorated knee geometry was valgus, then the knee arthroplasty procedure is preoperatively planned such that the implanted prosthetic knee implants result in a knee geometry that is generally the same extent valgus. Finally, if the patient's pre-deteriorated knee geometry was neutral, such as depicted in FIG. 4, then the knee arthroplasty procedure is preoperatively planned such that the implanted prosthetic knee implants result in a knee geometry that is generally neutral.

In natural or kinematic alignment, the goal may be to create a prosthetic knee joint line 222 that recreates the patient's pre-degenerated knee joint line 222, which may have been parallel to the ground during a two legged stance in the frontal plane (feet approximated and parallel to the ground during gait). Studies suggest that with the feet approximated in two-legged stance, the joint line is parallel to the ground, and the mechanical axis is positioned with a two to three degree inward inclination.

A knee arthroplasty procedure may be considered a zero-degree mechanical axis or neutral alignment procedure when the knee arthroplasty procedure is preoperatively planned such that the prosthetic knee implants implanted during the knee arthroplasty procedure generally result in a neutral knee geometry for the patient, regardless of whether the patient's pre-deteriorated knee geometry was varus, valgus or neutral. In zero-degree mechanical axis alignment, the goal may be to create a prosthetic knee joint line 222 that is perpendicular to the TMA 218, the TMA 218 coinciding with the MA 214.

A patient's natural pre-degenerated knee geometry may have served the patient well prior to knee joint degeneration. However, a physician may determine that it is in the patient's best interest to receive a post surgical knee geometry that is a natural alignment, neutral alignment, or something in between, depending on the physician's assessment of the patient's deteriorated bone geometry and condition, the applicability of available prosthetic implants, and other factors. Consequently, there is a need for the systems and methods disclosed herein.

Figure 1A:
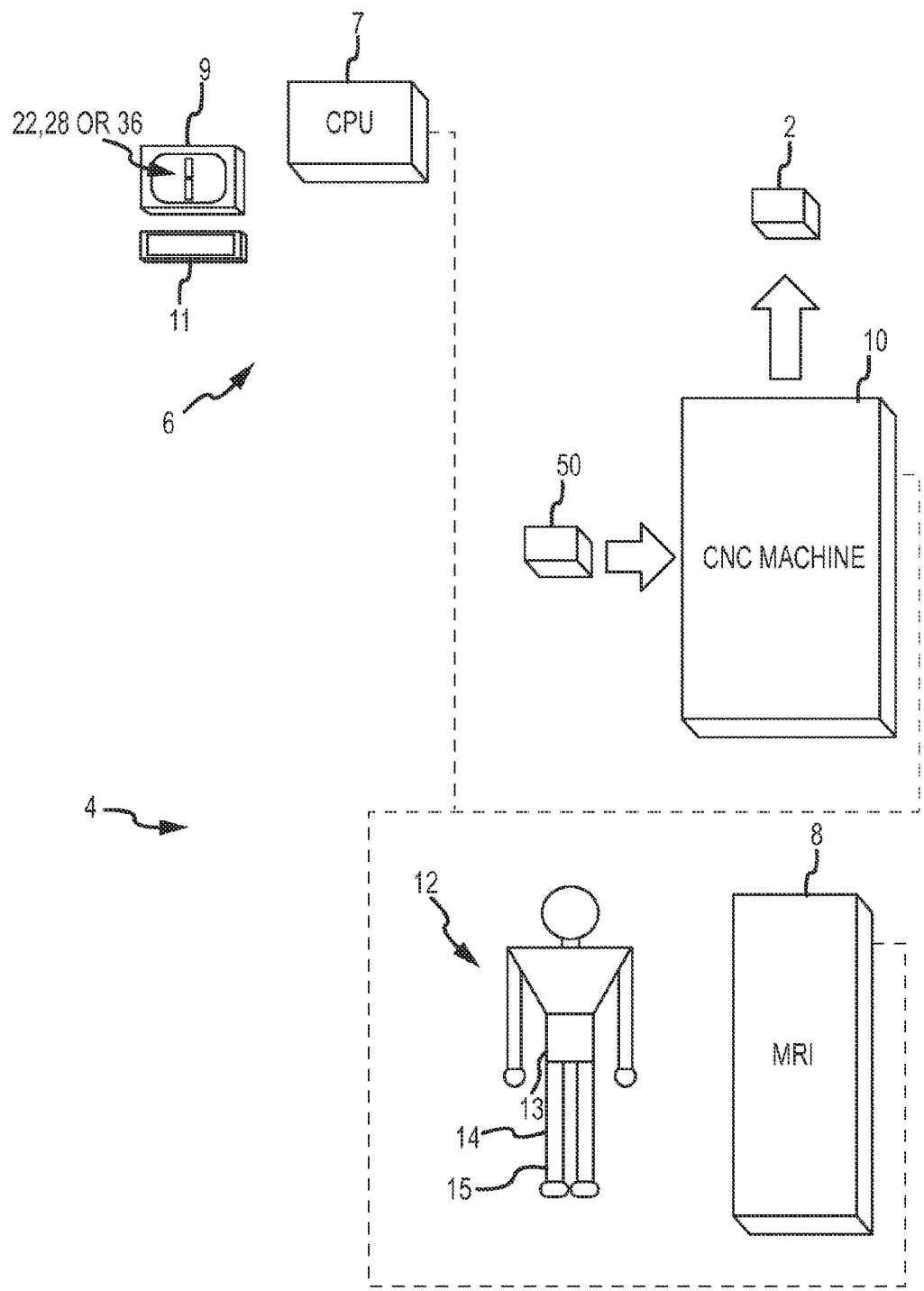
FIG. 1A is a schematic diagram of a system for employing the automated jig production method disclosed herein.

To provide an overall understanding of the systems 4 for, and methods of, producing the customized arthroplasty jigs 2, reference is made to FIGS. 1A-1K. FIG. 1A is a schematic diagram of a system 4 for employing the automated jig production method disclosed herein. FIGS. 1B-1K are flow chart diagrams outlining the jig production method disclosed herein. The systems 4 for, and methods of, producing the customized arthroplasty jigs 2 can be broken into six sections.

The first section, which is discussed with respect to FIG. 1A and [Blocks 100-115 and 125-135] of FIGS. 1B-1E, pertains to example methods of generating two-dimensional ("2D") body coil MRI images 52 and 2D knee coil MRI images 16, identifying hip, knee and ankle center points 54, 56, 57, 58 in the 2D body coil MRI images 52, and matching the 2D knee coil MRI images 16 to the 2D body coil MRI images 52 with respect to location and orientation in a global coordinate system 63.

Figure 1B:
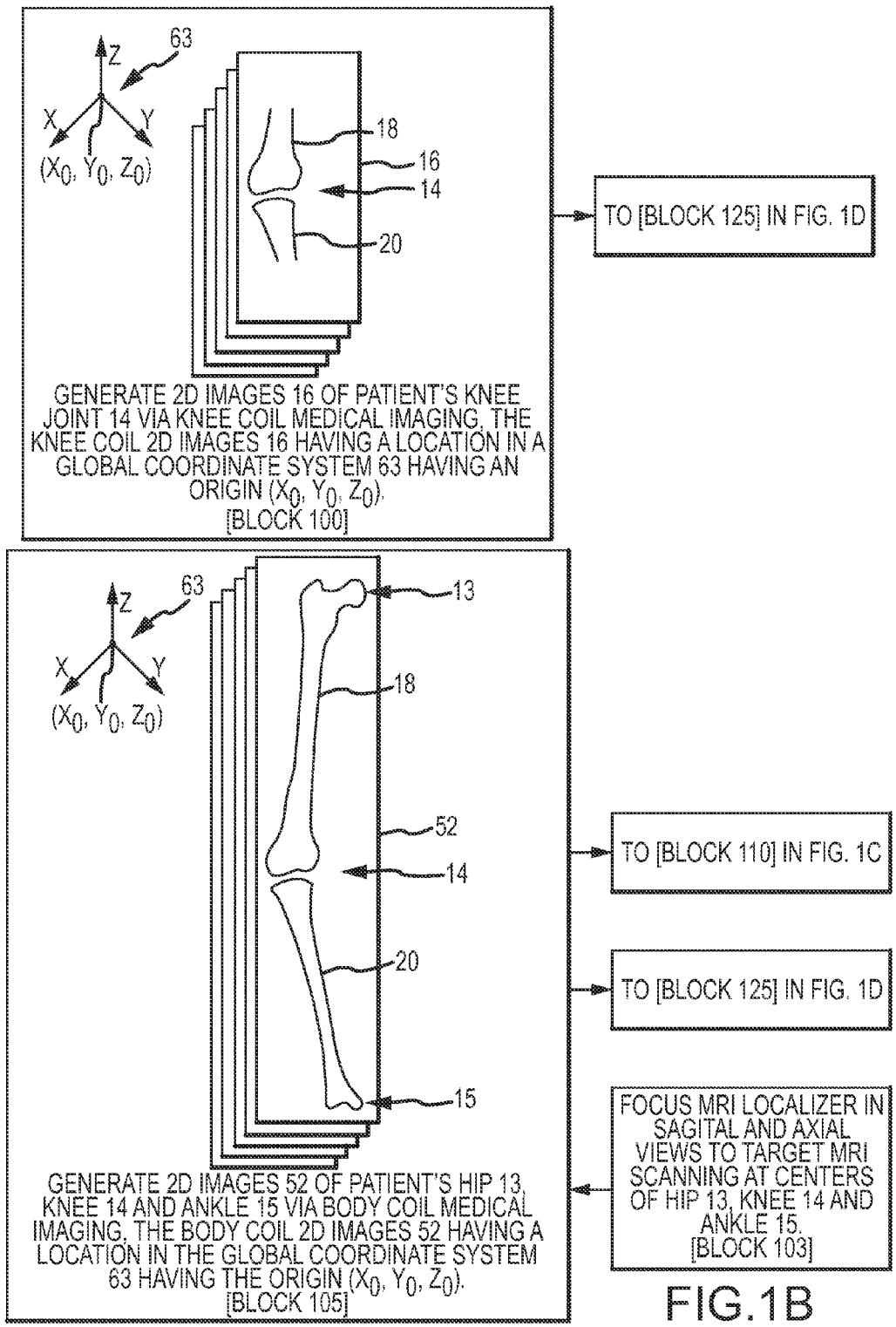
FIGS. 1B-1K are flow chart diagrams outlining the jig production method disclosed herein.
Figure 1C:
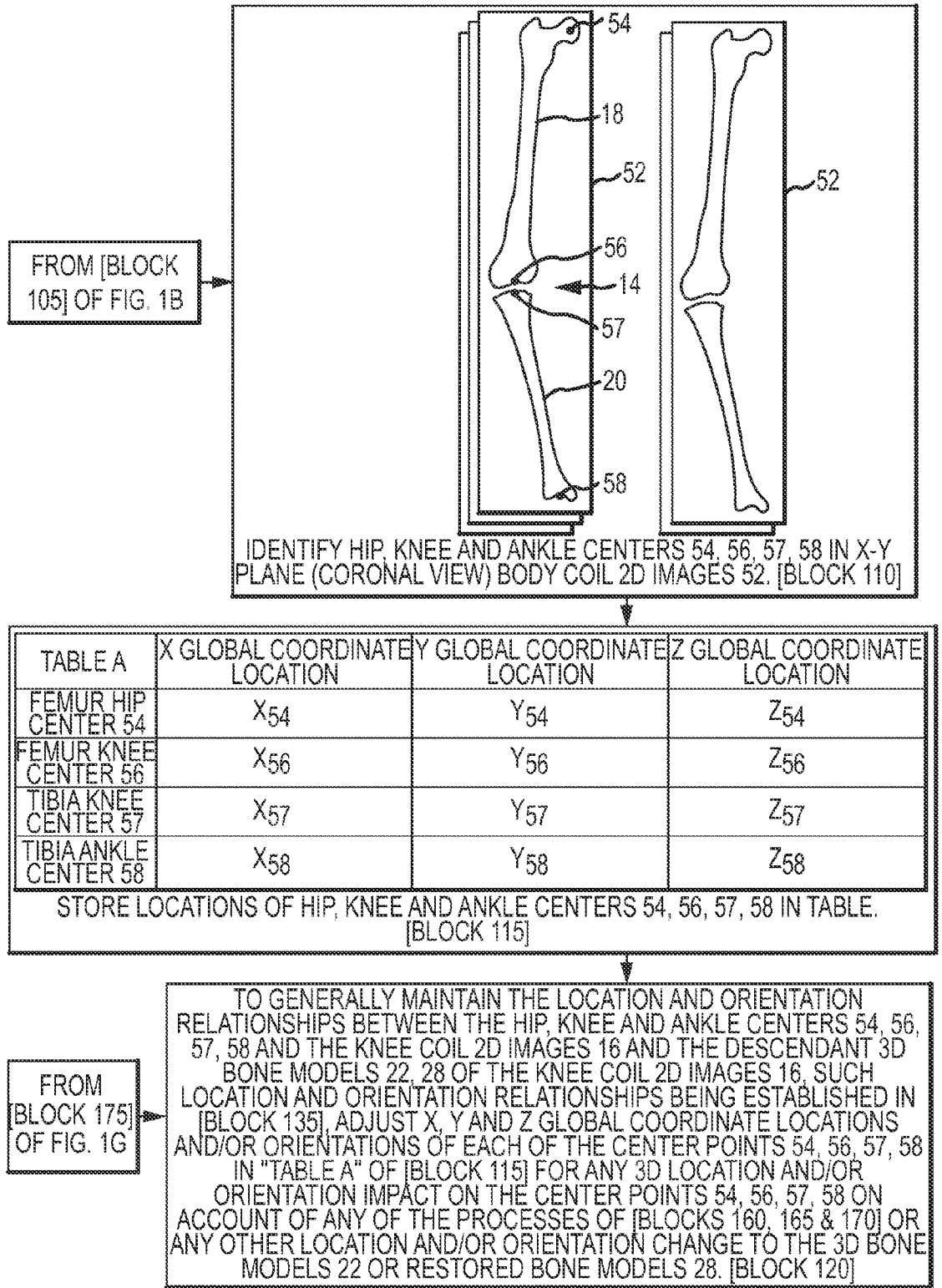
Figure 1D:
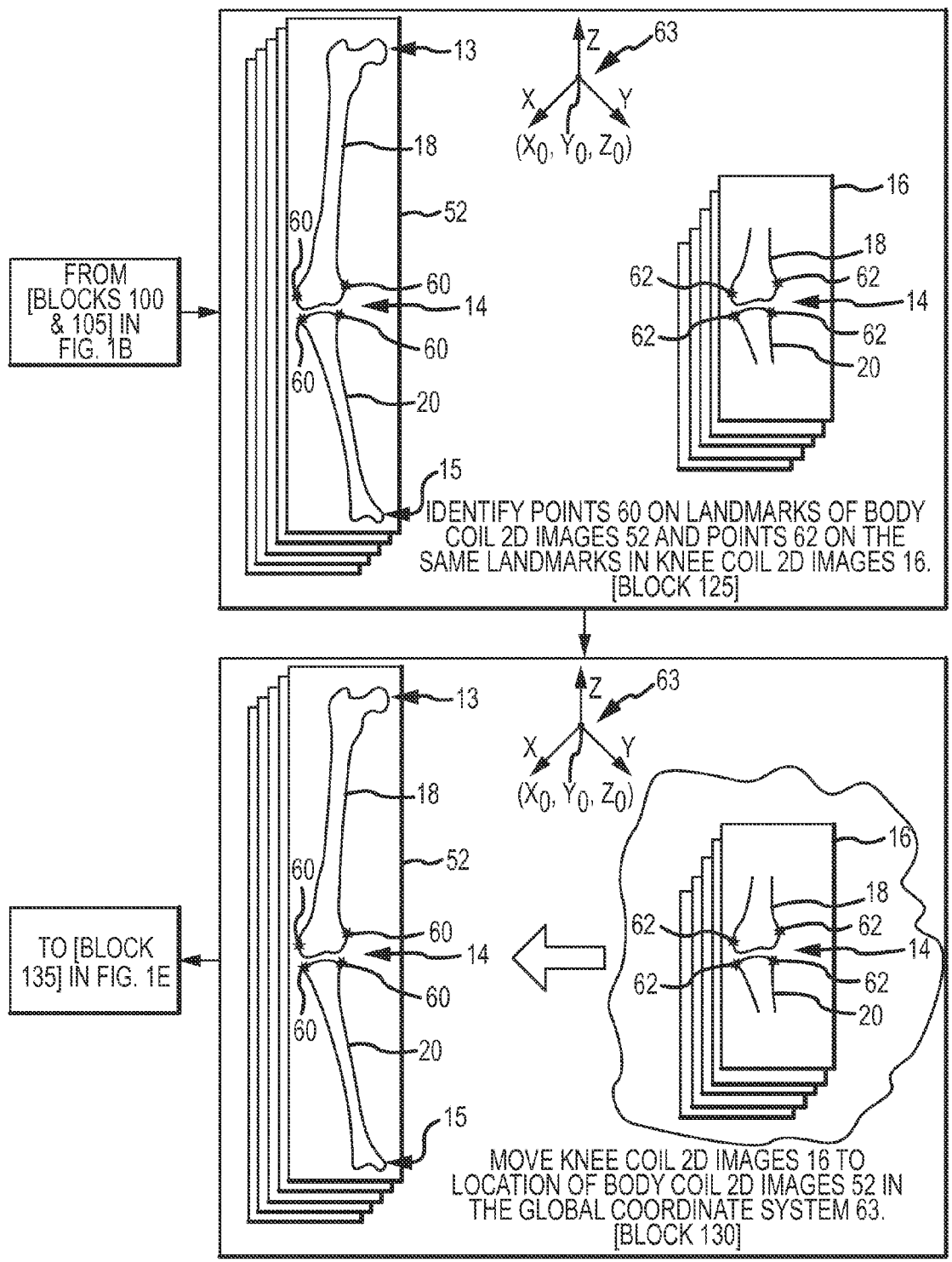
Figure 1E:
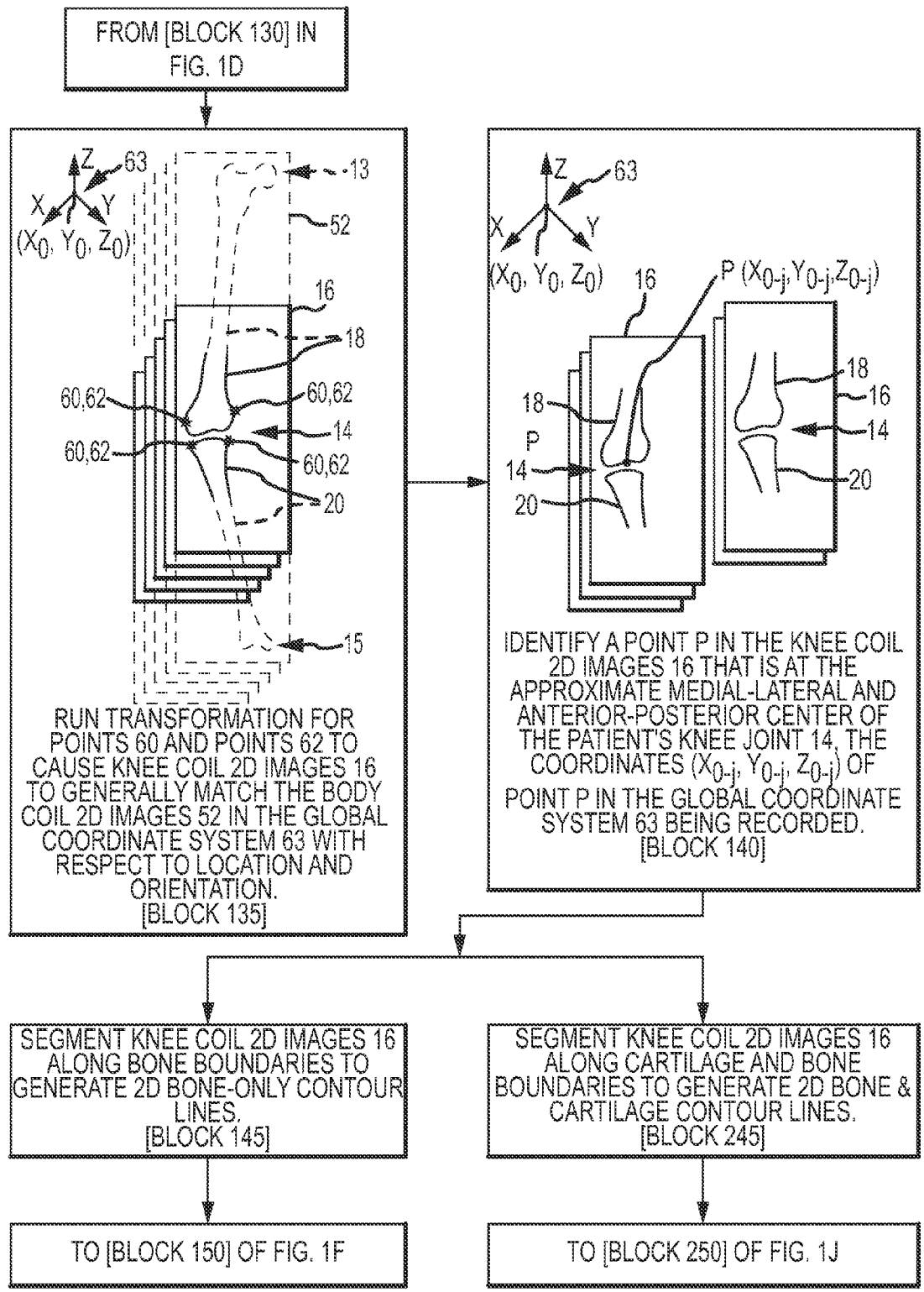
Figure 1F:
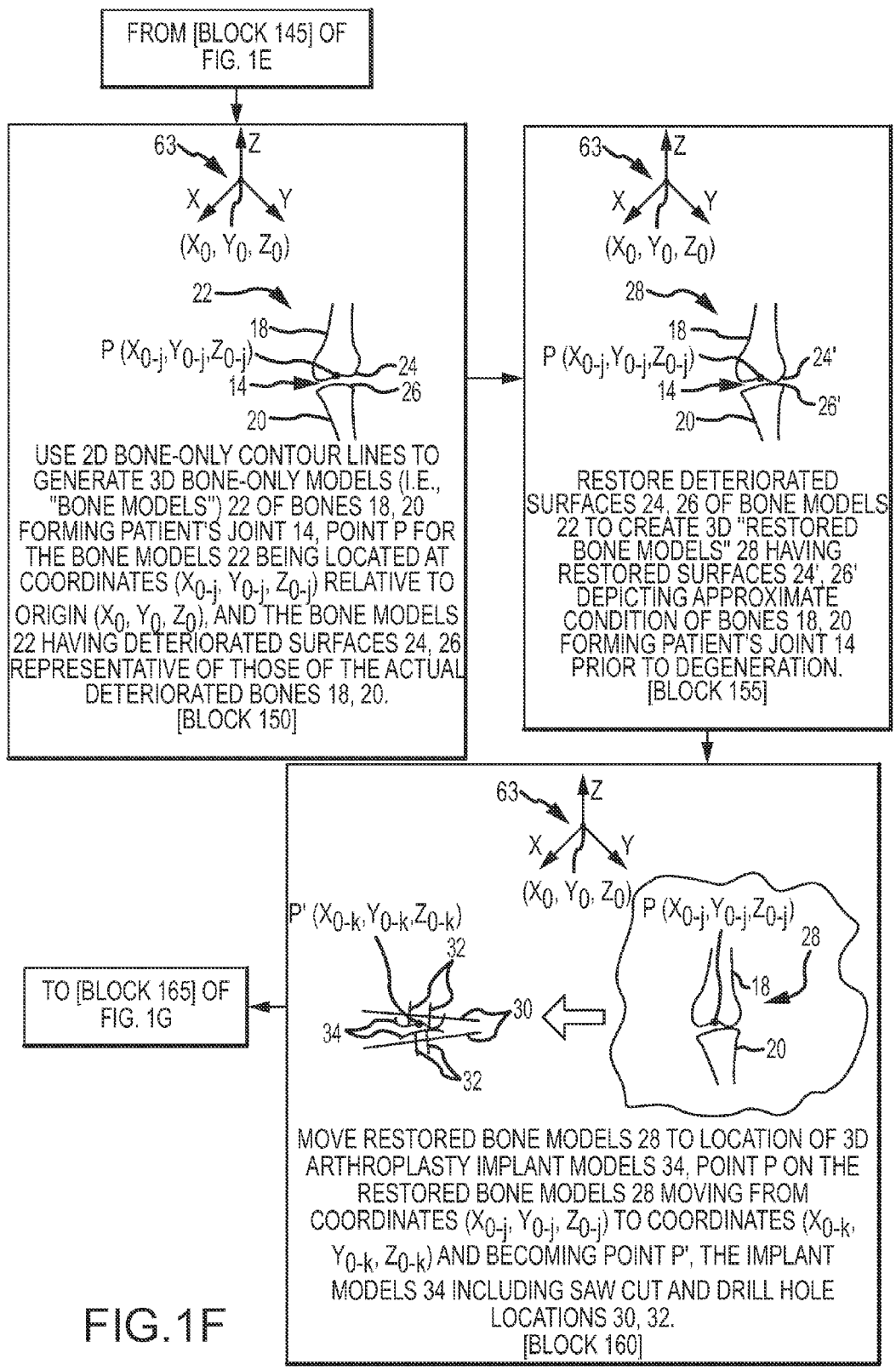
Figure 1G:
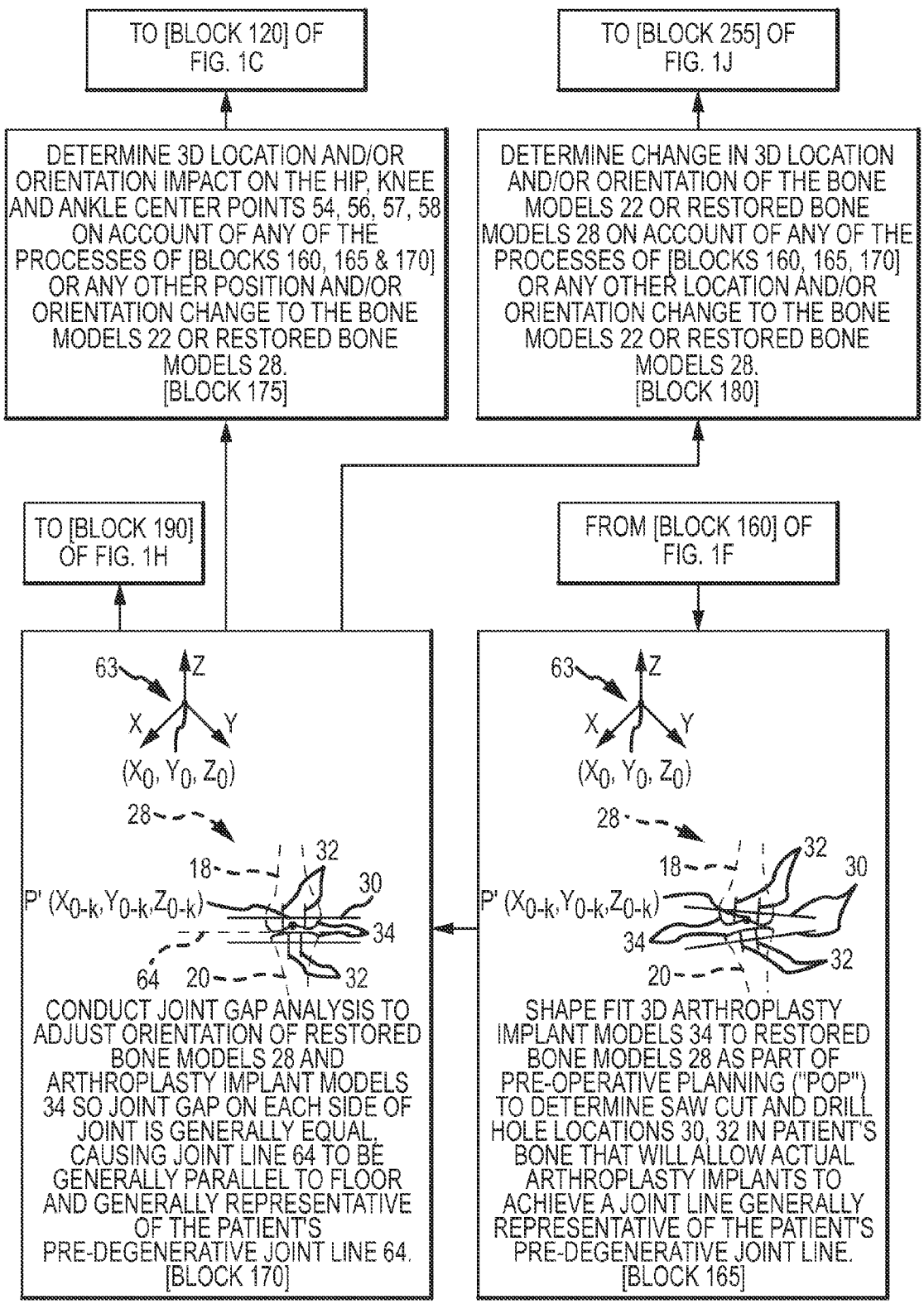

The second section, which is discussed with respect to FIG. 1A and [Blocks 140-170] of FIGS. 1E-1G, pertains to example methods of pre-operative planning ("POP") to determine bone resection locations and orientations in a knee arthroplasty. For example, the second section includes establishing a reference point P in the 2D knee coil MRI images 16, segmenting the 2D knee coil MRI images 16, generating 3D bone models 22 from the segmented images, generating 3D restored bone models 28 from the bone models 22, shape matching the 3D restored bone models 28 to 3D implant models 34 in a 3D computer model environment, noting the location and orientation of saw cut (bone resection) and drill hole locations 30, 32, and adjusting for ligament balance.

The resulting "saw cut and drill hole data" 44 is referenced to the restored bone models 28 to provide saw cuts and drill holes that will allow arthroplasty implants to achieve a joint alignment that is: (1) generally representative of the patient's pre-degenerative joint line (i.e., natural alignment); generally corresponding to a zero mechanical axis alignment; or (3) somewhere between (1) and (2). Whether the resections result in a joint alignment that is (1), (2) or somewhere between (1) and (2) may be a result of physician input and modification of the natural joint alignment calculated during POP.

Figure 1H:
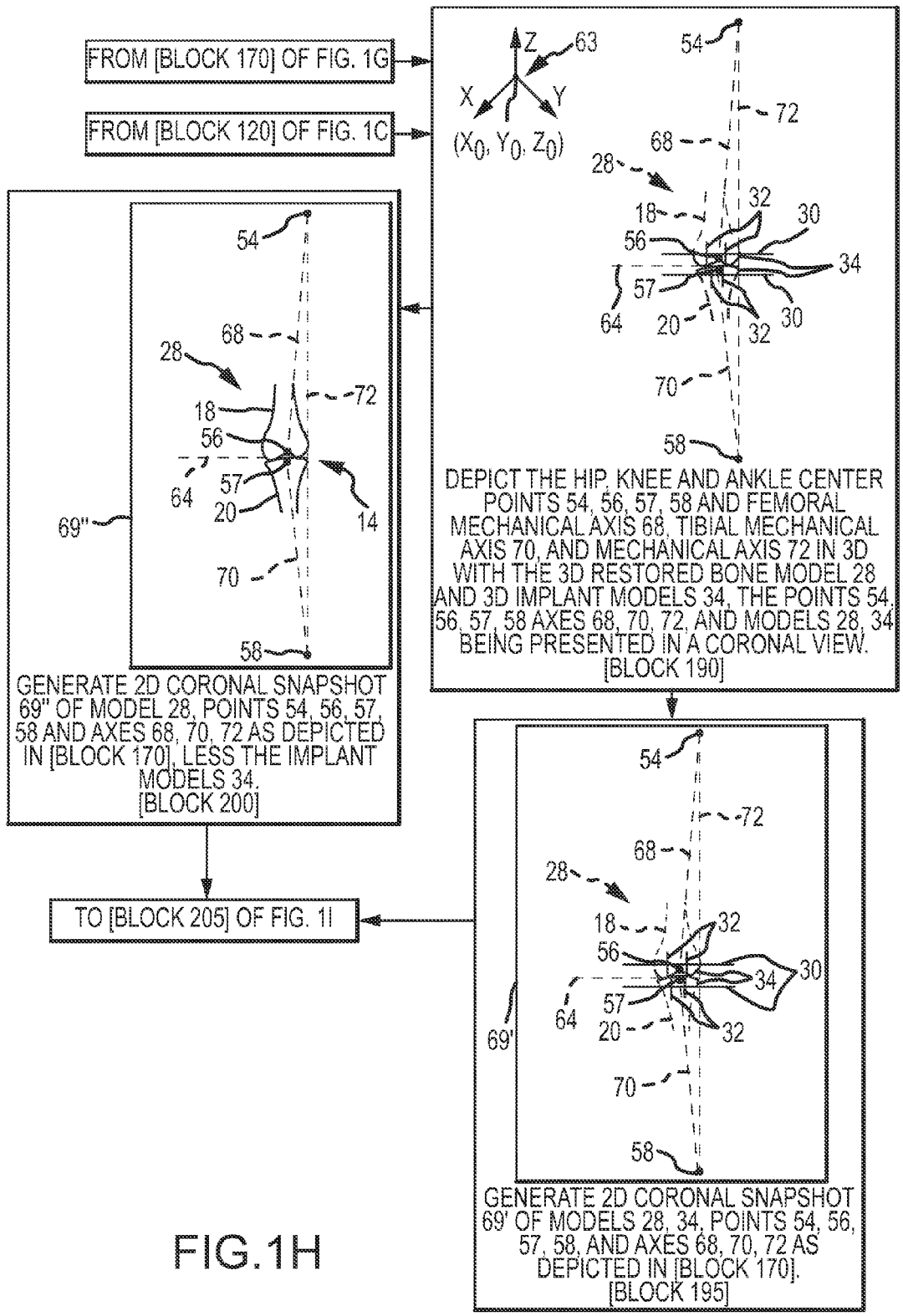
Figure 1I:
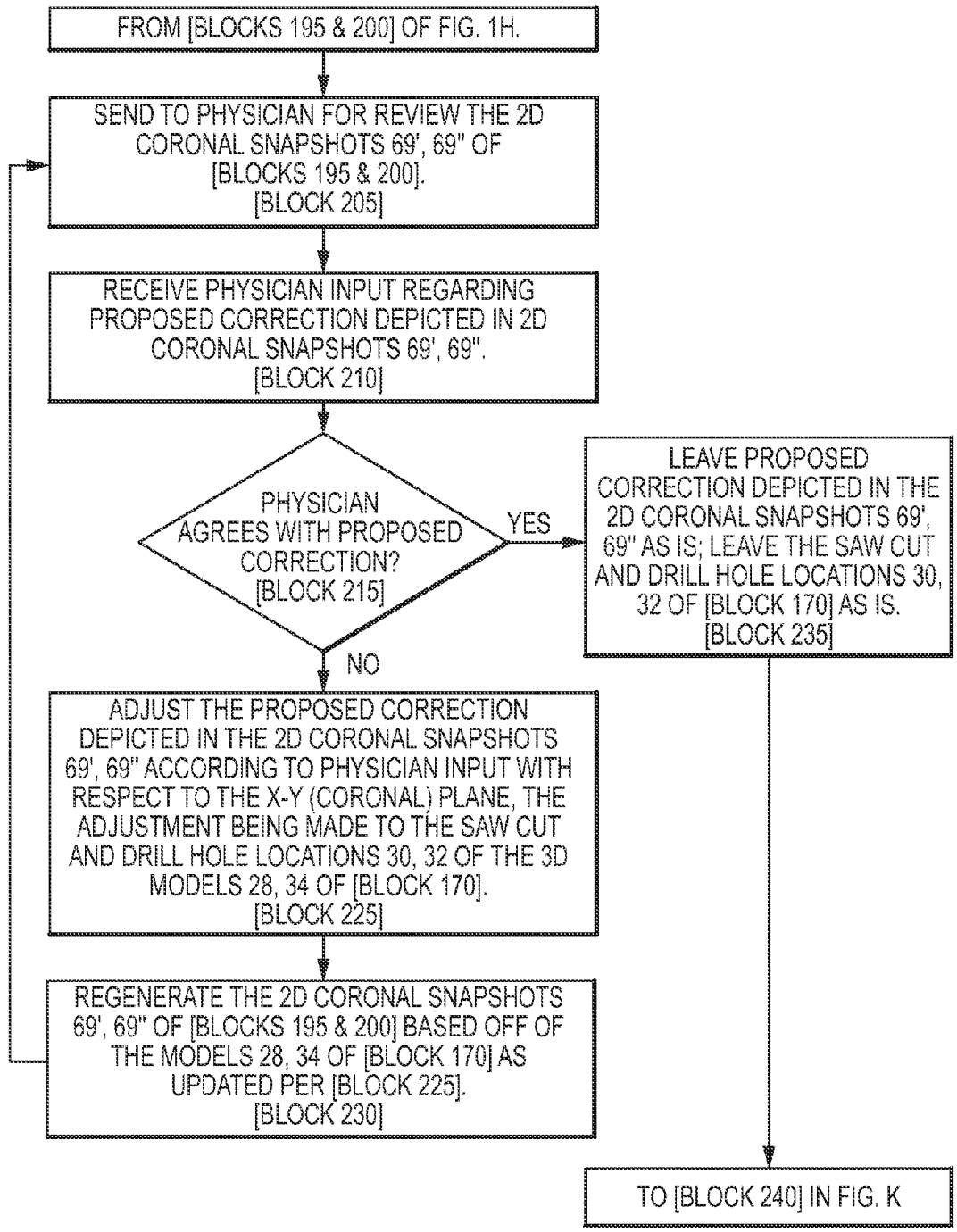

The third section, which is discussed with respect to [Blocks 190-235] of FIGS. 1H-1I, pertains to example methods of presenting information to the surgeon regarding the POP and, more specifically, the resections 30, joint line 64, femoral mechanical axis ("FMA") 68, tibial mechanical axis ("TMA") 70, and mechanical axis ("MA") 72. The surgeon provides approval of the present POP information or directions to modify the POP.

Figure 1J:
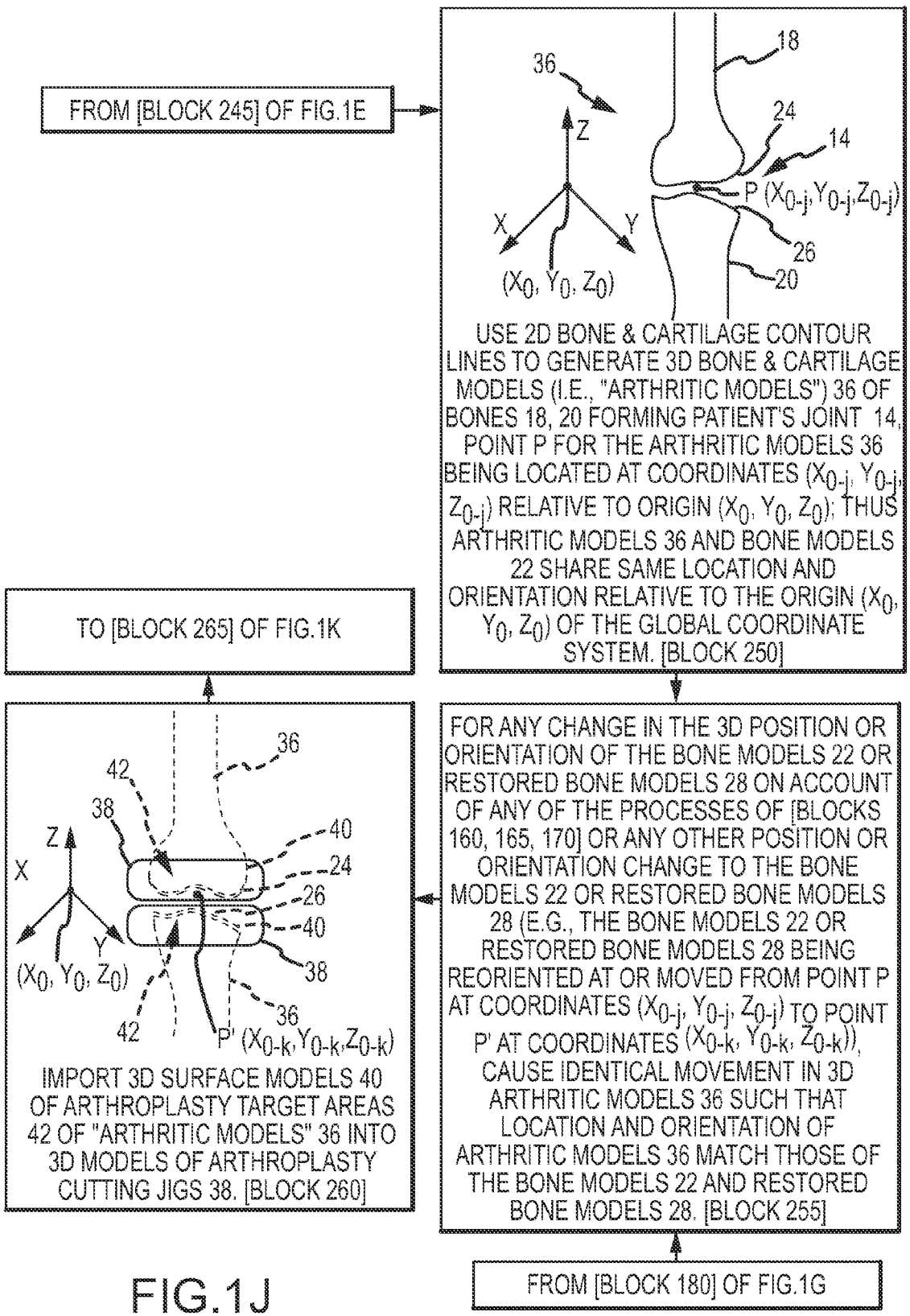

The fourth section, which is discussed with respect to [Blocks 120, 175, 180 and 255] of FIGS. 1C, 1G and 1J, pertains to examples of methods of maintaining location and orientation relationships between the various 3D models 22, 28, 36 and center points 54, 56, 57, 58 as the various 3D models 22, 28, 36 are modified or otherwise manipulated.

The fifth section, which is discussed with respect to FIG. 1A and [Blocks 180 and 245-260] of FIGS. 1E, 1G and 1J, pertains to example methods of generating 3D arthritic models 36 from the segmented images, importing into the 3D computer generated jig models 38 3D computer generated surface models 40 of arthroplasty target areas 42 of the 3D computer generated arthritic models 36 of the patient's joint bones, and updating the location and orientation of the these models 36, 38, 40 to maintain the location and position relationship with the bone models 22, 28 that are manipulated during POP. The resulting "jig data" 46 is used to produce a jig customized to matingly receive the arthroplasty target areas of the respective bones of the patient's joint.

Figure 1K:
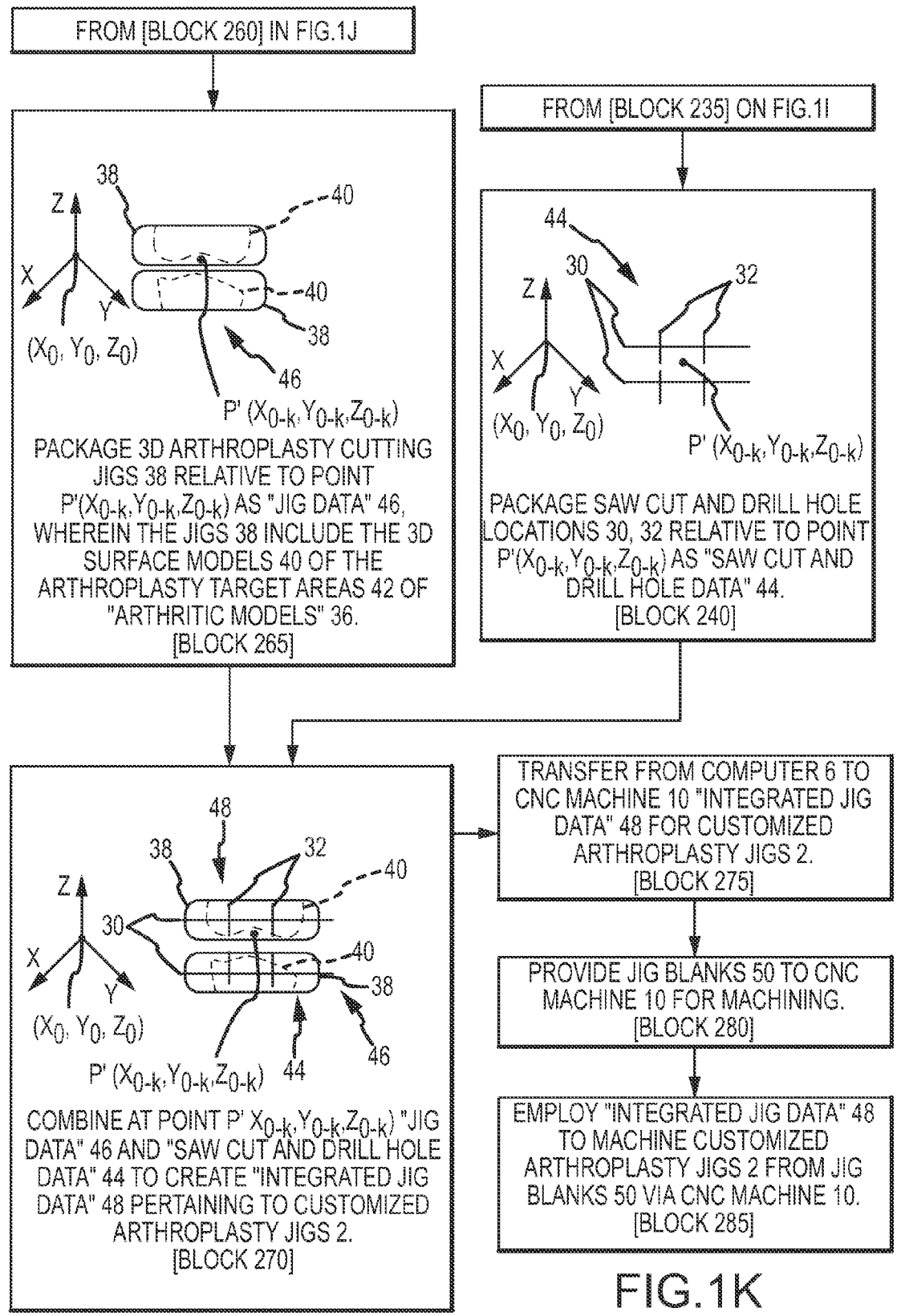

The sixth section, which is discussed with respect to FIG. 1A and [Blocks 240 and 265-285] of FIG. 1K, pertains to methods of combining or integrating the "saw cut and drill hole data" 44 with the "jig data" 46 to result in "integrated jig data" 48. The "integrated jig data" 48 is provided to the CNC machine 10 or another automated production machine, such as, for example, a rapid production machine (e.g., a stereolithography apparatus ("SLA") machine) for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to achieve a predetermined or desired joint alignment. Depending on the physician's review and input as outlined in [Blocks 190-235] of FIGS. 1H-1I, the predetermined or desired joint alignment will: generally restore the patient's joint line to its pre-degenerated state or natural alignment state; generally correspond to a zero degree mechanical axis alignment; or be somewhere between natural alignment and zero degree mechanical axis alignment.

As shown in FIG. 1A, the system 4 includes a computer 6 having a CPU 7, a monitor or screen 9 and operator interface controls 11. The computer 6 is linked to a medical imaging system 8, such as a CT or MRI machine 8, and a computer controlled manufacturing system 10, such as a CNC milling machine 10.

As indicated in FIG. 1A, a patient 12 has a hip joint 13, a knee joint 14, and an ankle joint 15, wherein the knee joint 14 is to be the subject of the arthroplasty procedure. In other embodiments, the joint 14 to be replaced may be another type of joint, for example, an elbow, ankle, wrist, hip, shoulder, skull/vertebrae or vertebrae/vertebrae interface, etc. As discussed in greater detail below, in one embodiment, the patient 12 has the hip, knee and ankle joints 13, 14, 15 scanned in the imaging machine 8. The imaging machine 8 makes a plurality of scans of the joints 13, 14, 15 wherein each scan pertains to a thin slice of a single joint or multiple joints.

Figure 6:
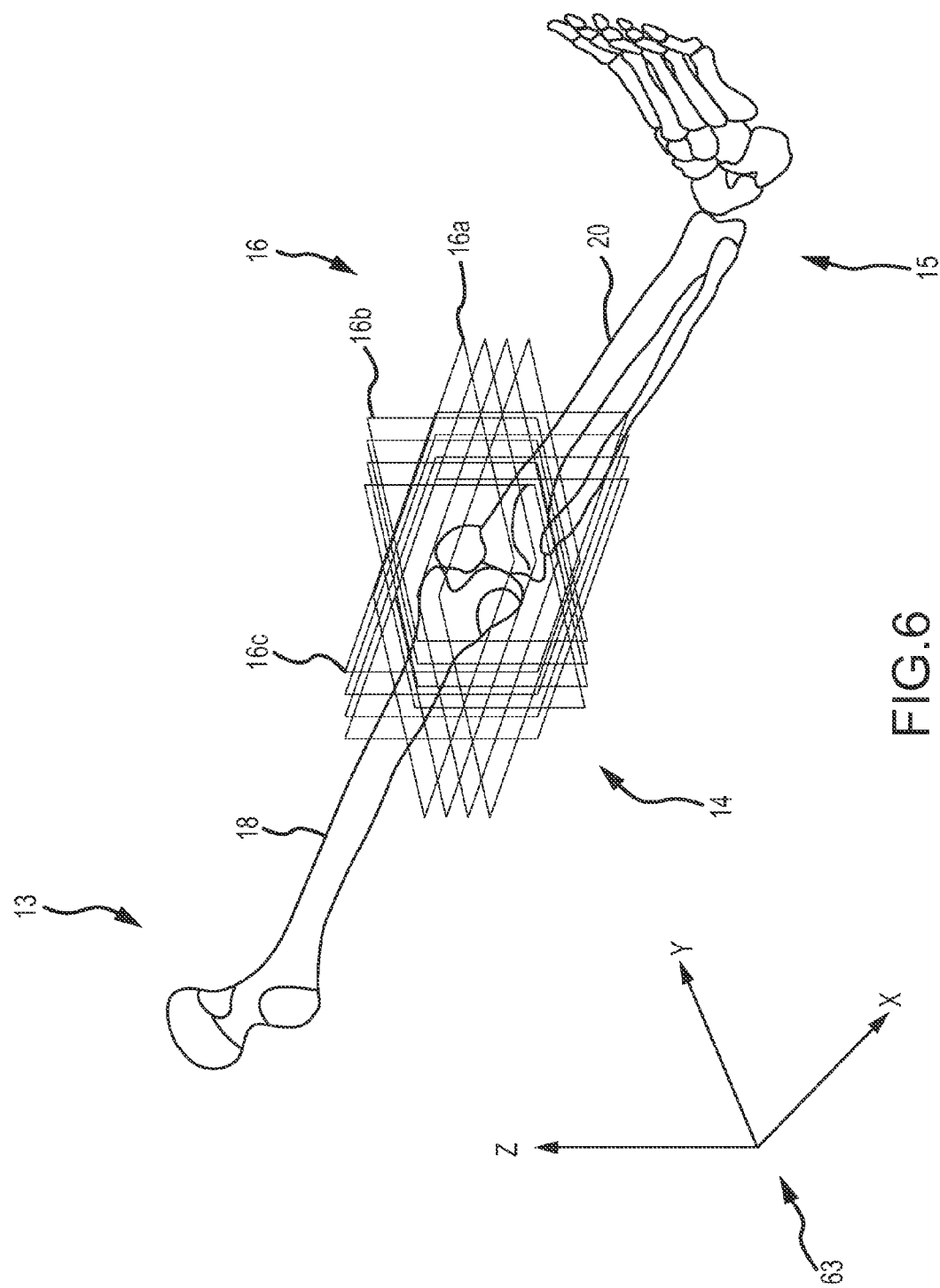
FIG. 6 is an isometric view of the patient's leg bone structure illustrating knee coil images.

As can be understood from FIG. 1B, in one embodiment, the patient's leg bone structure undergoes two types of scanning in the imaging machine 8. Specifically, as indicated in FIG. 6, which is an isometric view of the patient's leg bone structure, in one embodiment, the patient's knee 14, including portions of the femur 18 and tibia 20, is scanned in a MRI knee coil to generate a plurality of two dimensional ("2D") knee coil MRI images 16 of the patient's knee 14 [Block 100]. In one embodiment, the knee coil 2D images 16 include a plurality of coronal images 16a, a plurality of axial images 16b and a plurality of sagittal images 16c. In other embodiments, the knee coil 2D images 16 may be any combination of coronal, sagittal and/or axial views; for example, the views making up the images 16 may be coronal plus sagittal, coronal plus sagittal plus axial, coronal plus axial, etc. The knee coil 2D images 16 have a location and orientation in a global coordinate system 63 having an origin ($X_0$, $Y_0$, $Z_0$). In one embodiment, the MRI imaging spacing for the 2D knee coil images 16 may range from approximately 2 mm to approximately 6 mm.

Figure 7:
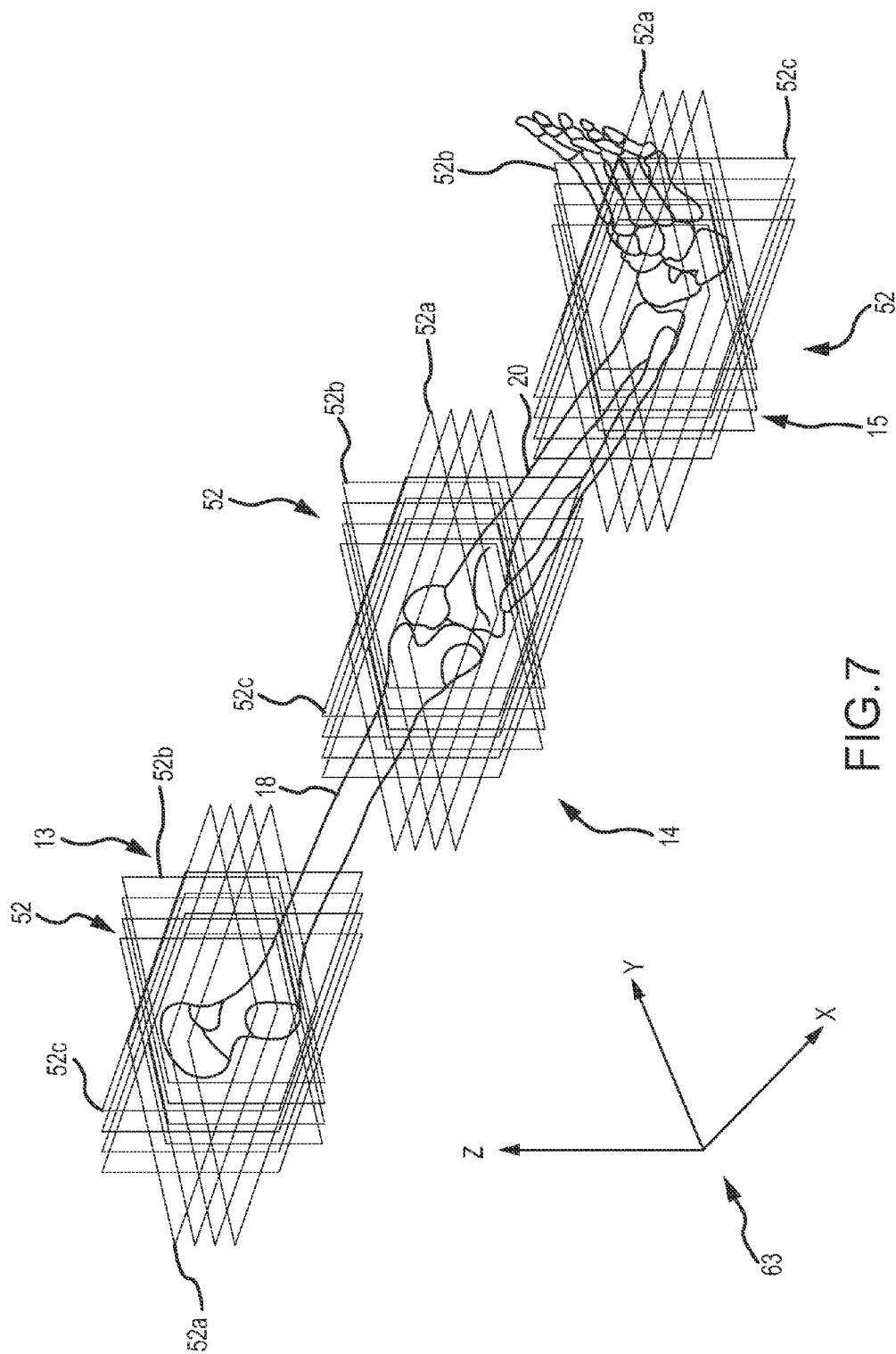
FIG. 7 is an isometric view of the patient's leg bone structure illustrating body coil images.

As illustrated in FIG. 7, which is an isometric view of the patient's leg bone structure, in one embodiment, the patient's entire leg length, or portions thereof that include the patient's hip 13, knee 14 and ankle 15, is scanned in a MRI body coil to generate a plurality of 2D body coil MRI images 52 of the patient's entire leg length or, at least, a plurality of body coil 2D MRI images 52 at each of the patient's the hip 13, knee 14 and ankle 15 [Block 105]. In other words, the body coil 2D images 52 include all of hip 13, knee 14 and ankle 15 or, at least, certain portions thereof. In one embodiment, the body coil 2D images 52 include a plurality of coronal images 52a, a plurality of axial images 52b and a plurality of sagittal images 52c at each of the hip 13, knee 14 and ankle 15. In other embodiments, the body coil 2D images 52 may be any combination of coronal, sagittal and/or axial views; for example, the views making up the images 52 may be coronal plus sagittal, coronal plus sagittal plus axial, coronal plus axial, etc. The body coil 2D images 52 have a location and orientation in the global coordinate system 63 having the origin ($X_0$, $Y_0$, $Z_0$). In one embodiment, the MRI imaging spacing for the 2D body coil images 52 may range from approximately 0.5 mm to approximately 5 mm. As a result, the number of generated MRI imaging slices for the knee coil approach is larger than the body coil approach. In other words, the numbers N for the knee coil and M for the body coil of MRI slices may be expressed as follows: N(coronal slices)>>M(coronal slices); N(sagittal slices)>>M(sagittal slices); and N(axial slices)>>M(axial slices).

As can be understood from FIG. 1B, in one embodiment, before performing the MRI scanning that will result in the body coil 2D images 52, the MRI localizer may be employed in the sagittal and axial views of the patient's leg bone structure to target the MRI scanning process at the centers of the patient's hip 13, knee 14 and ankle 15 [Block 103]. Thus, the MRI body coil scanning may be caused to focus at the centers of the hip, knee and ankle, increasing the likelihood of generating coronal body coil images that are adequate for identifying the centers of the hip, knee and ankle as discussed below.

While the embodiment is discussed in the context of the imaging being via MRI, in other embodiments the imaging is via CT or other medical imaging methods and systems. In one embodiment employing MRI, the imaging process may be as disclosed in U.S. patent application Ser. No. 11/946,002 to Park, which is titled "Generating MRI Images Usable For The Creation Of 3D Bone Models Employed To Make Customized Arthroplasty Jigs," was filed Nov. 27, 2007 and is incorporated by reference in its entirety into this Detailed Description.

Figure 14:
FIG. 14 is a coronal 2D body coil image of the hip with the center of the femoral head indicated.
Figure 15:
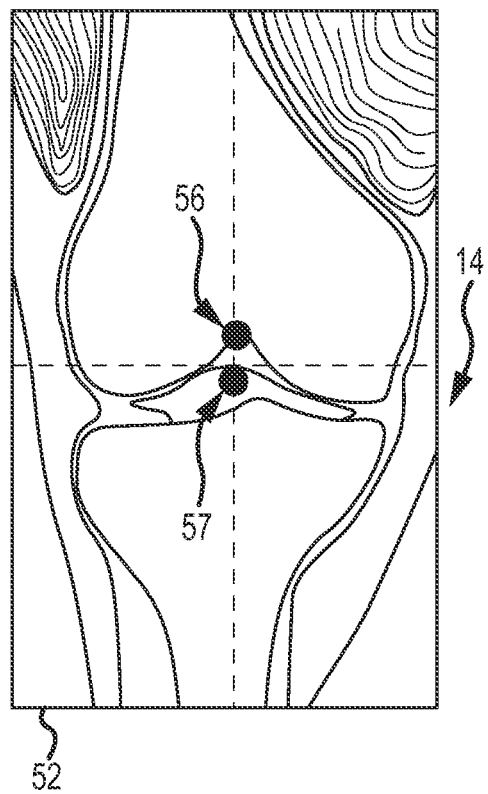
FIG. 15 is a coronal 2D knee coil image of the knee with the centers of the femur and tibia indicated.
Figure 16:
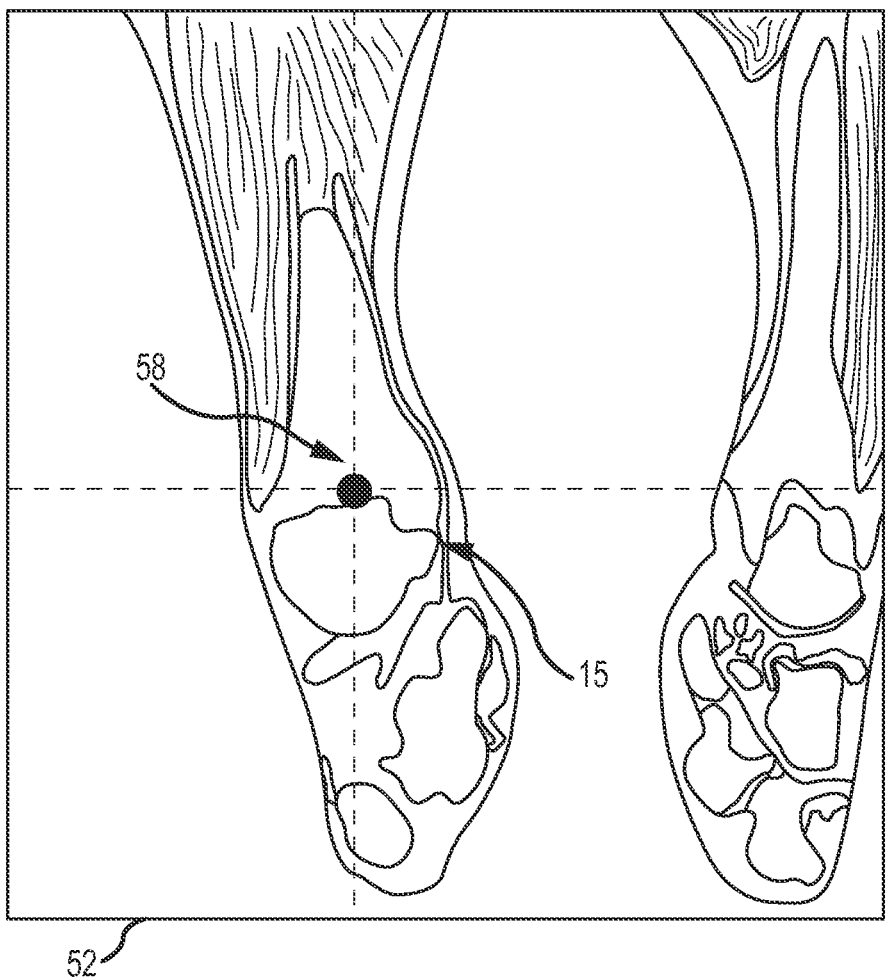
FIG. 16 is a coronal 2D body coil image of the ankle with the center of the ankle joint indicated.

As can be understood from FIG. 1A, the 2D images 16, 52 are sent to the computer 6 for analysis and modeling. As indicated in FIG. 1C, hip, knee and ankle centers 54, 56, 57, 58 are identified in the body coil 2D images 52 [Block 110]. For example, as indicated FIGS. 14-16, which are coronal 2D body coil images 52 of the hip 13, knee 15 and ankle 16, respectively, a person sitting in front of the monitor 9 of the work station 6 tabs through the various coronal 2D body coil images 52 at each of the hip, knee and ankle to determine visually an image 52 at each of the hip, knee and ankle that is near the center of each of these joints 13, 14, 15. When the operator visually identifies such an image for each of the joints 13, 14, 15, the operator electronically marks the centers 54, 56, 57, 58 for each of these joints 13, 14, 15, as indicated in FIGS. 14-16, causing the location of the centers 54, 56, 57, 58 to be electronically stored relative to the global coordinate system 63.

In one embodiment, the hip, knee and ankle centers 54, 56, 57, 58 are identified only in the coronal views of the body coil 2d images 52. In one embodiment, the X, Y and Z global coordinate locations for each of the femur hip center 54, femur knee center 56, tibia knee center 57 and tibia ankle center 58 are stored, for example, in a table or matrix in a computer file separate from the 3D bone models 22 or 3D restored bone models 28, discussed below [Block 115]. In other embodiments, the X, Y and Z global coordinate locations for each of the femur hip center 54, femur knee center 56, tibia knee center 57 and tibia ankle center 58 are stored with or as part of the 3D bone models 22 or 3D restored bone models 28, discussed below.

In one embodiment, the hip center can be the approximate center point of the femur head via visual examination. The ankle center can be the approximate center point of the cortical bone rim of the ankle plafond (i.e., the distal articular surface of tibia) via visual examination. The knee center can be the approximate center point close to the intercondylar groove of the distal femur and/or the approximate center point of the tibia spine in the 3D restored knee model. The centers of the hip and ankle in the 2D body coil images 52 may be identified. The approximate joint center coordinates of the hip, ankle and 3D knee model may be recorded as ($x'_{1-3}$, $y'_{1-3}$, $z'_{1-3}$). For example, the joint center coordinates for each of hip, knee, and ankle, may be, respectively, ($x'_1$, $y'1$, $z'_1$), ($x'_2$, $y'_2$, $z'_2$), and ($x'_3$, $y'_3$, $z'_3$).

Figure 8:
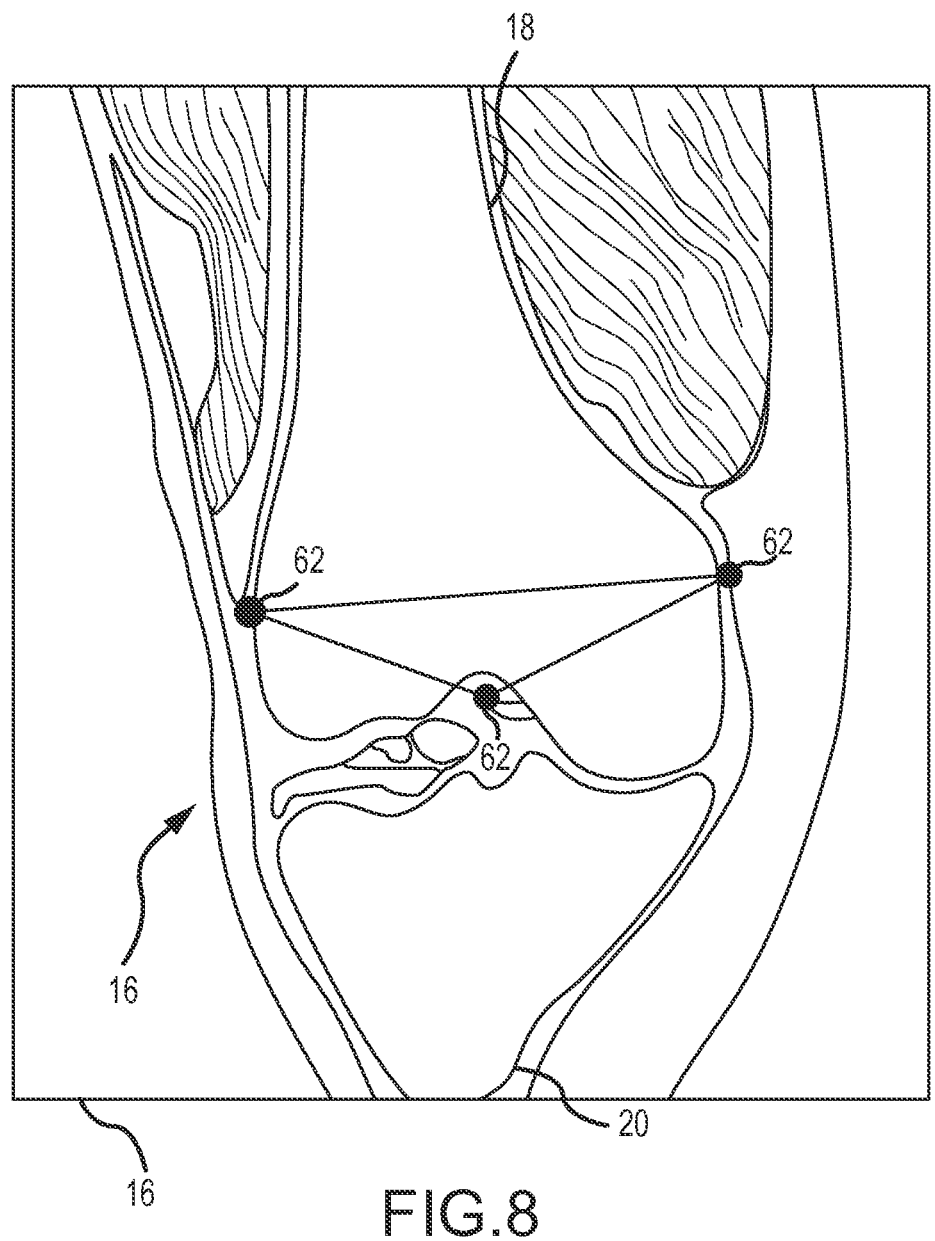
FIG. 8 is a coronal 2D knee coil image with points identified on landmarks of the knee region of the femur.

As shown in FIG. 1D, points 60 and 62 are identified respectively on corresponding landmarks in the 2D body coil images 52 and 2D knee coil images 16 [Block 125]. For example, as shown in FIG. 8, which is a coronal 2D knee coil image 16, points 62 are identified on landmarks of the knee region of the femur 18. In some embodiments, the 2D knee coil image 16 used to identify the landmarks of the knee region of the femur 18 is the 2D knee coil image 16 of the set of knee coil images 16 having the widest and most clear or definite depiction of the femur 18 in the knee region. For example, a person viewing the 2D knee coil images 16 via the monitor 9 of the work station 6 may tab through the various coronal 2D knee coil images 16 to determine the specific coronal 2D knee coil image 16 in which the femur 18 is depicted with the largest and most clear condyle contour. The person then marks or identifies the points 62 of the femur landmarks. As shown in FIG. 8, examples of such landmarks on the knee region of the femur may include the center of the femur condyle region near the trochlear groove, the most medial and lateral points of the epicondyles, or other identifiable landmarks.

Figure 9:
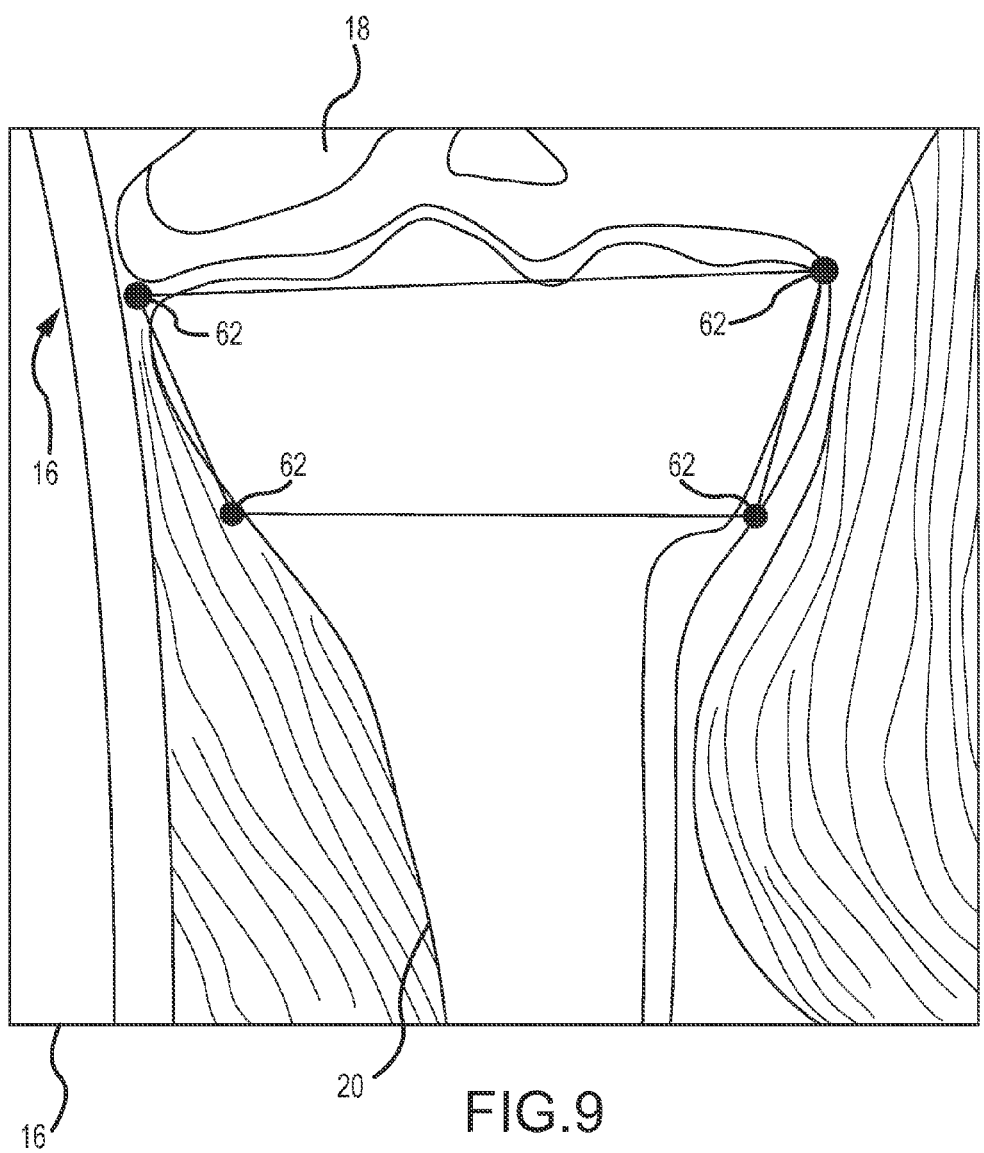
FIG. 9 is a coronal 2D knee coil image with points identified on landmarks of the knee region of the tibia.

As shown in FIG. 9, which is a coronal 2D knee coil image 16, points 62 may also be identified on landmarks of the knee region of the tibia 20. In some embodiments, the 2D knee coil image 16 used to identify the landmarks of the knee region of the tibia 20 is the 2D knee coil image 16 of the set of knee coil images 16 having the widest and most clear or definite depiction of the tibia 20 in the knee region. For example, a person viewing the 2D knee coil images 16 via the monitor 9 of the work station 6 may tab through the various coronal 2D knee coil images 16 to determine the specific coronal 2D knee coil image 16 in which the tibia 20 is depicted with the largest and most clear condyle contour. The person then marks or identifies the points 62 of the tibia landmarks. As shown in FIG. 9, examples of such landmarks on the knee region of the tibia may include the medial and lateral edges of the tibial condyles, the medial and lateral transitions from the tibial plateau to the tibial shaft, or other identifiable landmarks.

Figure 10:
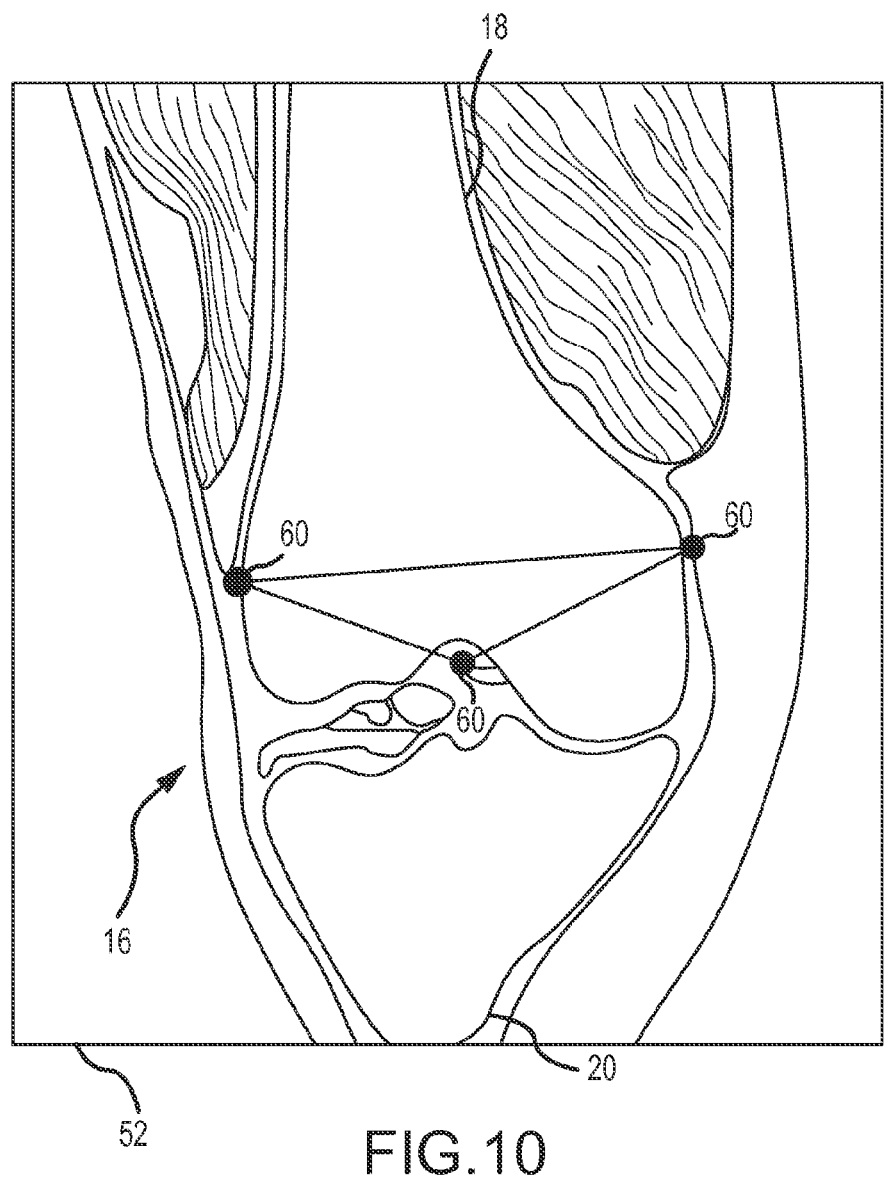
FIG. 10 is a coronal 2D body coil image with points identified on landmarks of the knee region of the femur.

As shown in FIG. 10, which is a coronal 2D body coil image 52, points 60 are identified on landmarks of the knee region of the femur 18. In some embodiments, the 2D body coil image 52 used to identify the landmarks of the knee region of the femur 18 is the 2D body coil image 52 of the set of body coil images 52 having the widest and most clear or definite depiction of the femur 18 in the knee region. For example, a person viewing the 2D body coil images 52 via the monitor 9 of the work station 6 may tab through the various coronal 2D body coil images 52 to determine the specific coronal 2D body coil image 52 in which the femur 18 is depicted with the largest and most clear condyle contour. The person then marks or identifies the points 60 of the femur landmarks, which, as can be understood from a comparison of FIGS. 10 and 8, will be selected to be at least generally the same as the points 62 of the femur landmarks identified in the coronal 2D knee coil image 16.

Figure 11:
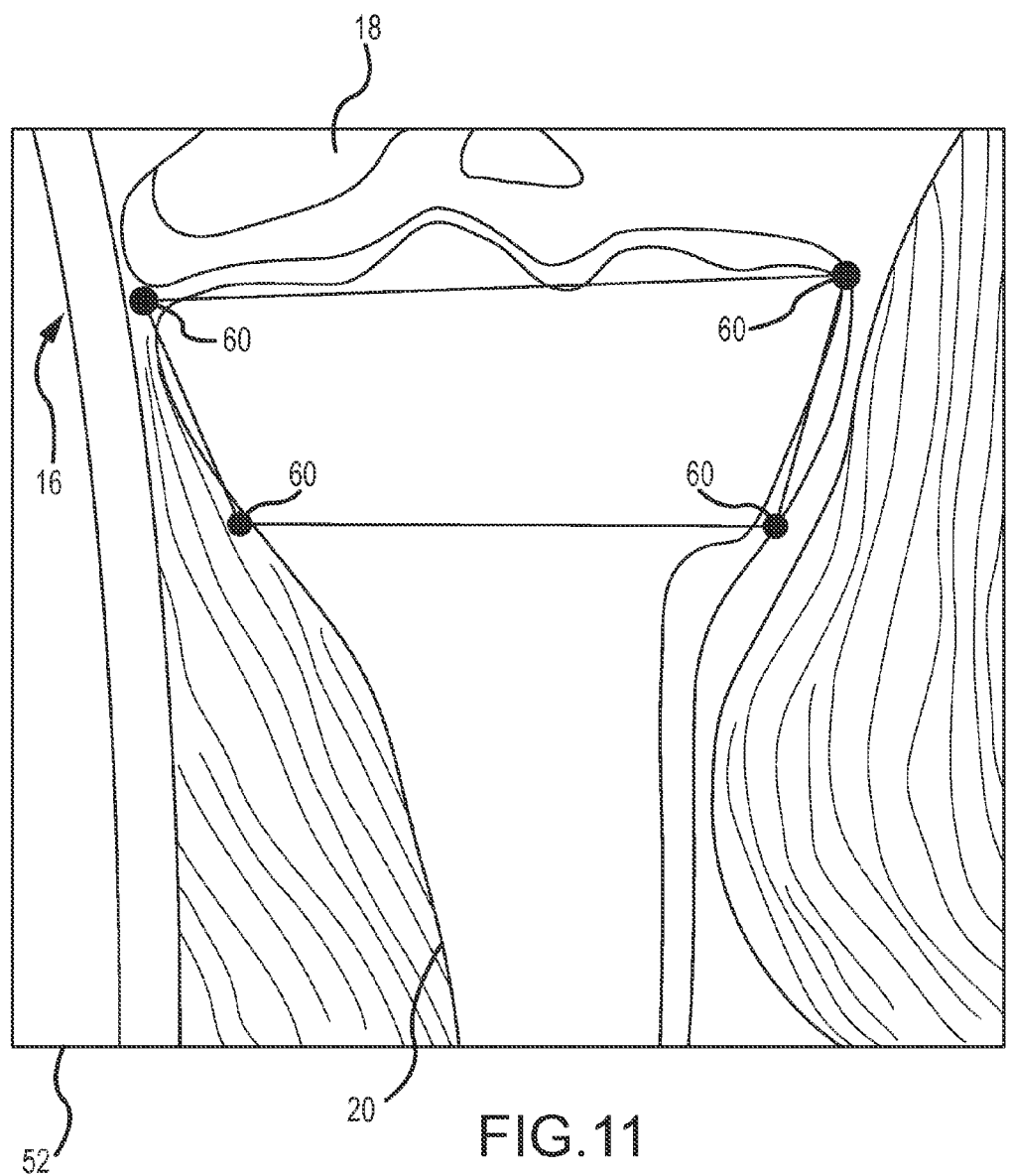
FIG. 11 is a coronal 2D body coil image with points identified on landmarks of the knee region of the tibia.

As shown in FIG. 11, which is a coronal 2D body coil image 52, points 60 are also identified on landmarks of the knee region of the tibia 20. In some embodiments, the 2D body coil image 52 used to identify the landmarks of the knee region of the tibia 20 is the 2D body coil image 52 of the set of body coil images 52 having the widest and most clear or definite depiction of the tibia 20 in the knee region. For example, a person viewing the 2D body coil images 52 via the monitor 9 of the work station 6 may tab through the various coronal 2D body coil images 52 to determine the specific coronal 2D body coil image 52 in which the tibia 20 is depicted with the largest and most clear condyle contour. The person then marks or identifies the points 60 of the tibia landmarks, which, as can be understood from a comparison of FIGS. 11 and 9, will be selected to be at least generally the same as the points 62 of the tibia landmarks identified in the coronal 2D knee coil image 16.

In one embodiment, three or more points 62 are identified in the respective 2D knee coil images 16 of FIGS. 8 and 9, and three or more points 60 are identified in the respective 2D body coil images 52 of FIGS. 10 and 11. The three or more femur points 62 may be in the same coronal 2D knee coil image 16, as illustrated in FIG. 8, and the three or more tibia points 62 may be in the same coronal 2D knee coil image 16, as depicted in FIG. 9. Similarly, the three or more femur points 60 may be in the same coronal 2D body coil image 52, as illustrated in FIG. 10, and the three or more tibia points 60 may be in the same coronal 2D body coil image 52, as depicted in FIG. 11.

In other embodiments, the three or more points 60, 62 may be distributed across multiple coronal images 16, 52. For example, the three or more femur points 62 may be distributed across two or more coronal 2D knee coil images 16, and the three or more tibia points 62 may be distributed across two or more coronal 2D knee coil images 16. Similarly, the three or more femur points 60 may be distributed across two or more coronal 2D body coil images 52, and the three or more tibia points 60 may be distributed across two or more coronal 2D body coil images 52.

In yet other embodiments, the three or more points 60, 62 may be distributed across different types of images 16, 52, such as, for example, a combination of coronal, axial and/or sagittal. For example, the three or more femur points 62 may be distributed across one or more coronal 2D knee coil image 16, one or more sagittal knee coil image, and/or one or more axial knee coil image, and the three or more tibia points 62 may be distributed across one or more coronal 2D knee coil image 16, one or more sagittal knee coil image, and/or one or more axial knee coil image. Similarly, the three or more femur points 60 may be distributed across one or more coronal 2D body coil image 52, one or more sagittal body coil image, and/or one or more axial body coil image, and the three or more tibia points 60 may be distributed across one or more coronal 2D body coil image 52, one or more sagittal body coil image, and/or one or more axial body coil image.

Regardless of how many points 60, 62 are located and in which type of image views and combinations of views, in one embodiment, the coordinate locations of the points 60, 62 in the global coordinate system 63 are stored for use with the transformation process discussed below.

As can be understood from FIG. 1D, the 2D knee coil images 16 are moved to the location of the 2D body coil images 52 in the global coordinate system 63, or vice versa [Block 130]. As can be understood from FIG. 1E, a transformation is run for the points 60, 62 to cause the 2D knee coil images 16 to generally positionally match the 2D body coil images 52 with respect to both location and orientation

Figure 12:
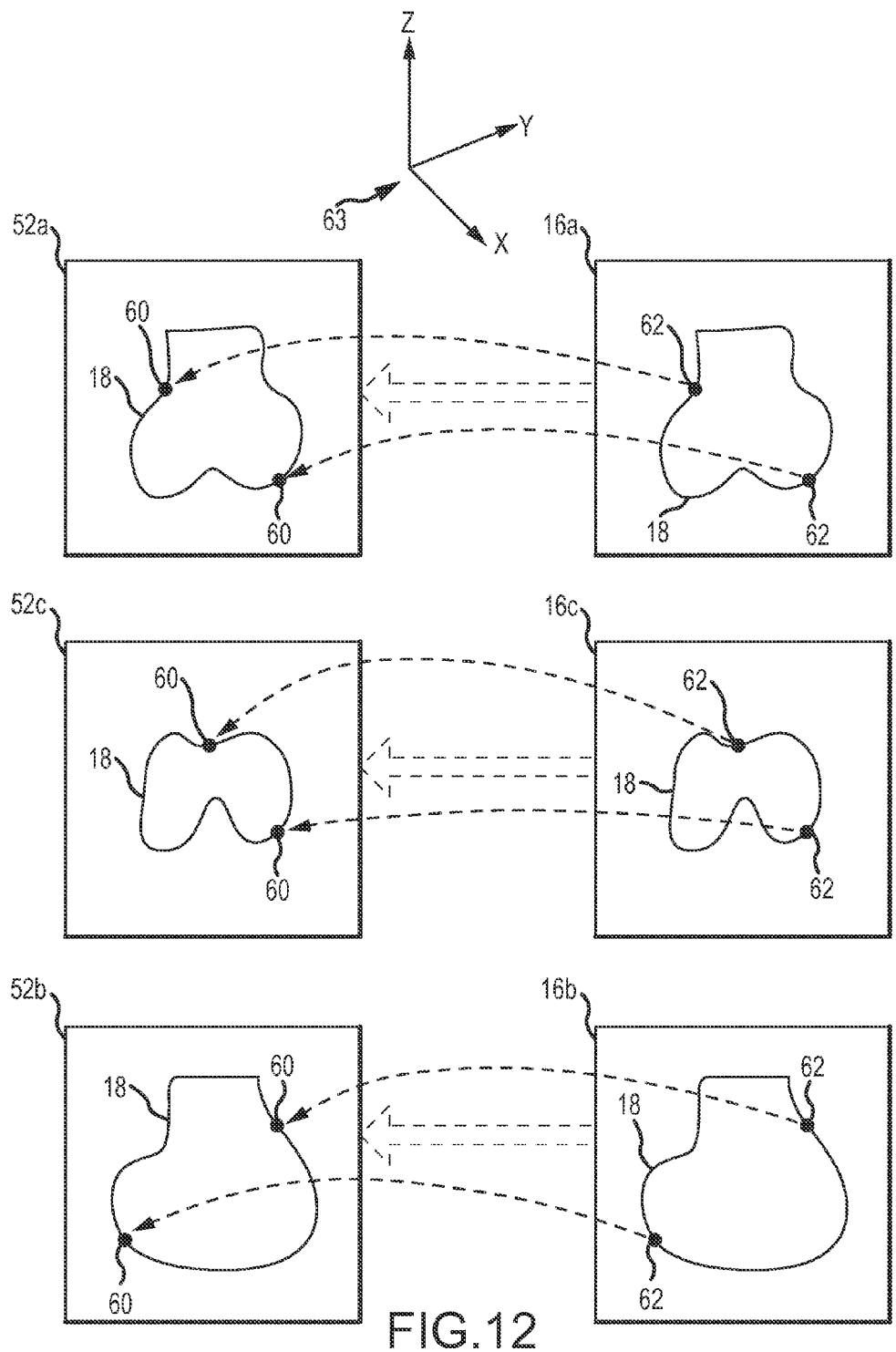
FIG. 12 is a diagrammatic depiction of the femur 2D knee coil images being transformed to the femur 2D body coil images.

[Block 135]. Specifically, as can be understood from FIG. 12, which is a diagrammatic depiction of the femur images 16, 52 being transformed, the transformation, in one embodiment, causes the coronal 2D knee coil images 16a to move to and positionally match the coronal 2D body coil images 52a by positioning the points 62 of the coronal 2D knee coil images 16a at the positions of the corresponding points 60 of the coronal 2D body coil images 52a in the global coordinate system 63. The embodiment of the transformation also causes the axial 2D knee coil images 16b to move to and positionally match the axial 2D body coil images 52b by positioning the points 62 of the axial 2D knee coil images 16b at the positions of the corresponding points 60 of the axial 2D body coil images 52b in the global coordinate system 63. The embodiment of the transformation also causes the sagittal 2D knee coil images 16c to move to and positionally match the sagittal 2D body coil images 52c by positioning the points 62 of the sagittal 2D knee coil images 16c at the positions of the corresponding points 60 of the sagittal 2D body coil images 52c in the global coordinate system 63.

Figure 13:
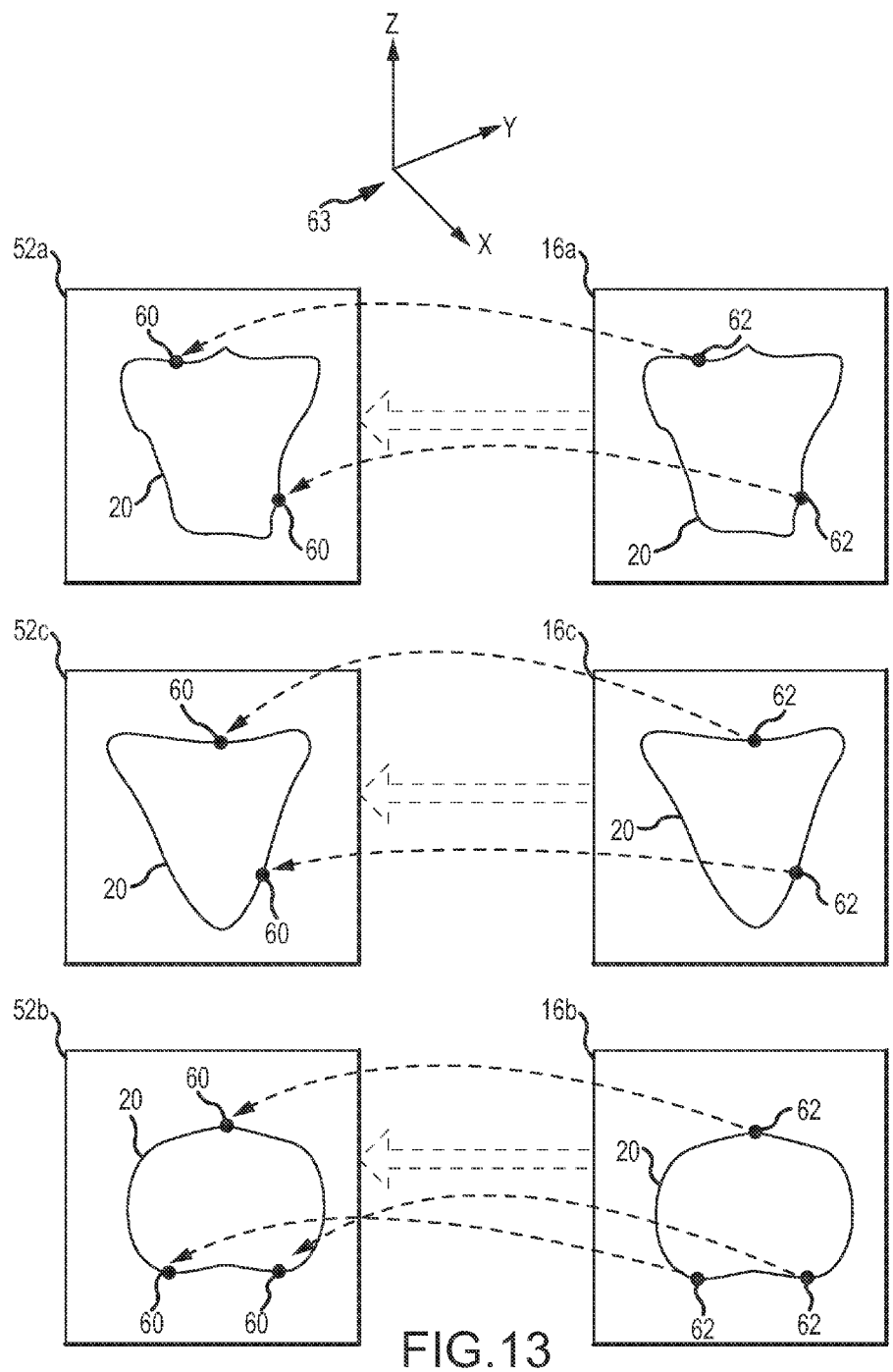
FIG. 13 is a diagrammatic depiction of the tibia 2D knee coil images being transformed to the tibia 2D body coil images.

As can be understood from FIG. 13, which is a diagrammatic depiction of the tibia images 16, 52 being transformed, the transformation, in one embodiment, causes the coronal 2D knee coil images 16a to move to and positionally match the coronal 2D body coil images 52a by positioning the points 62 of the coronal 2D knee coil images 16a at the positions of the corresponding points 60 of the coronal 2D body coil images 52a in the global coordinate system 63. The embodiment of the transformation also causes the axial 2D knee coil images 16b to move to and positionally match the axial 2D body coil images 52b by positioning the points 62 of the axial 2D knee coil images 16b at the positions of the corresponding points 60 of the axial 2D body coil images 52b in the global coordinate system 63. The embodiment of the transformation also causes the sagittal 2D knee coil images 16c to move to and positionally match the sagittal 2D body coil images 52c by positioning the points 62 of the sagittal 2D knee coil images 16c at the positions of the corresponding points 60 of the sagittal 2D body coil images 52c in the global coordinate system 63.

Whether the transformation operates on points in a particular view (e.g., coronal, axial and/or sagittal) or on a particular bone (e.g., femur and/or tibia) will depend on which landmarks the points 60, 62 are identified and in which views, as discussed above with respect to [Block 125] of FIG. 1D.

In one embodiment, the MRI coordinates of the points 60 on the bone landmarks of the region of the knee 14 in the 2D body coil images 52 may be illustrated as (x, y, z) and stored for further analysis. Similarly, the MRI coordinates of the points 62 on the bone landmarks of the region of the knee 14 in the 2D knee coil images 16 may be illustrated as (^x, ^y, ^z) and stored for further analysis. In one embodiment, the landmarks on which the points 60, 62 are located may be the epicondylar points of the distal femur, the approximate center of distal femur, the approximate center of proximal tibia, or other recognizable landmarks. In another embodiment, the points 60, 62 can be located anywhere on the area of distal femur and proximal tibia. The points for both the knee coil images 16 and body coil images 52 are in approximately similar locations via visual examination.

Once the points 60, 62 are similarly located in the images 16, 52, the transformation or optimization of the points 60, 62 and associated images 16, 52 takes place by brining as close as possible the points 62 of the 2D knee coil images 16, which are stored as (^x, ^y, ^z), to the points of the 2D body coil images 52, which are stored as (x, y, z). In other words, for example, the closeness of the two sets of points may be evaluated as the sum of squared distances from points in the first set to the whole second set. The manipulations of rotation and translation are applied to the points and associated images for the distal femur and proximal tibia.

In one embodiment, the transformation employs the Iterative Closest Point ("ICP") algorithm, gradient descent optimization or other optimization algorithms or transformations.

While [Blocks 125-135] of FIGS. 1D-1E and the preceding discussion illustrate a first positional matching embodiment wherein the 2D knee coil images 16 are positionally matched to the 2D body coil images 52 via the positional matching of landmark points 60, 62, other embodiments may employ other positional matching methods. For example, in a second positional matching embodiment and in a manner similar to that discussed below with respect to [Blocks 145-150] of FIGS. 1E-1F, the 2D knee coil images 16 are segmented and converted into a 3D bone model 22. Landmark points 60 are identified in the 2D body coil images 52 and these landmark points 60 are positionally matched to corresponding landmark points 62 in the 3D bone model 22 via the ICP.

A third positional matching embodiment employs a contour to contour positional matching approach. In one version of the third positional matching embodiment, splines are defined along the bone contours in the 2D body coil images 52 and along the bone contours in the 2D knee coil images 16. In another version of the third positional matching embodiment, the 2D knee coil images 16 are segmented and converted into a 3D bone model 22, and splines are defined along the bone contours in the 2D body coil images 52.

In some versions of the third positional matching embodiment, the splines are generally limited to the bone contours at specific landmarks. In other versions of the third positional matching embodiment, the splines extend along a substantial portion, if not the entirety, of the bone contours. Regardless of which version of the third positional matching embodiment is employed, the splines of the bone contours of the 2D body coil images 52 are positionally matched to bone contours of the 2D knee coil images 16 or the descendent 3D bone model 22 via the ICP algorithm or one of the other above-mentioned transformations. In one version of the third positional matching embodiment, the contours employed exist in both coronal and sagittal image slices.

In a fourth positional matching embodiment, image intensity variations in the 2D knee coil images 16 are identified and positionally matched to corresponding image intensity variations identified in the 2D body coil images 52. For example, image registration techniques are employed that are similar to those described in U.S. patent application Ser. No. 12/386, 105, which was filed Apr. 4, 2009, titled System and Method for Image Segmentation in Generating Computer Models of a Joint to Undergo Arthroplasty, and is hereby incorporated by reference into the present application in its entirety. Specifically, a bone 18, 20 in the 2D knee coil images 16 is segmented by a technician. Additionally, a technician may provide an initial approximate transform by specifying one or more landmarks in each of the knee coil and body coil images. The group of the rigid 3D transform with 6 parameters P (3 rotational angle+3 translation parameters) is parameterized. The function to be optimized is defined (see application Ser. No. 12/386,105—local image correlation function F). In one version of the fourth positional matching embodiment, a set of points S is defined in the knee coil images to be used in function F (e.g., the set of points S might be all the voxel points within 3-5 mm distance from the segmentation contours or some subset of such voxel points (e.g., a random subsample of such voxel points)). For every 6-dimensional parameter p in P, transform T(p) is applied to the set S to compute correlation F in the transformed set f(p)=F(T(p)(S)). Standard optimization techniques are applied in order to maximize f over parameters p. For example, when a technician provides an initial approximate transform, a gradient descent optimization method may be employed.

As can be understood from the preceding discussion, the various positional matching embodiments may employ a rigid 3D transform that best aligns the femur 18 in the 2D knee coil images 16 to the femur 18 in the 2D body coil images 52. A similar rigid 3D transform may also be employed in the various positional matching embodiments to best align the tibia 20 in the 2D knee coil images 16 to the tibia 20 in the 2D body coil images 52.

A given transform can be applied to the images 16, 52. In other words, a first image can be resampled over the transform. The transformed first image can be overlapped with the second image with the goal of the transform being that the two overlapped images match as close as possible in the region of femur bone. The transform process can be similarly run for the tibia.

While, in some embodiments, the transformed knee coil images and the body coil images may not match precisely because every MRI has a number of its own artifacts that degrade the image differently in different areas, the positional matching will be sufficient to allow the rest of the POP to continue as described herein.

As a general summary, in one embodiment, a few distinguished landmarks in the knee coil images are positional matched to similar or corresponding landmarks in the body coil images. In another embodiment, a larger number of points on the bone boundary in the body coil images are matched to the whole bone boundary (e.g., to the mesh surface in 3D) in the knee coil images. In yet another embodiment, the contours on the bone boundary in the body coil images are matched to the whole boundary of the knee coil images or, alternatively, the descendent 3D bone model. In the yet another embodiment, the image intensity variations around the bone boundary in the body coil images are matched to the image intensity variations in the knee coil images.

Each of embodiments one through three of the positional matching method may be done via a combination of manual and automated methodology or via an entirely automated methodology. The fourth embodiment of the positional matching method may be entirely automated.

As indicated in FIG. 1E, in one embodiment, point P is identified in the 2D knee coil images 16 once the 2D knee coil images 16 are positionally matched to the 2D body coil images 52 [Block 140]. In one embodiment, point P may be at the approximate medial-lateral and anterior-posterior center of the patient's knee joint 14. In other embodiments, point P may be at any other location in the 2D knee coil images 16, including anywhere on, near or away from the bones 18, 20 or the joint 14 formed by the bones 18, 20.

As described below with respect to [Blocks 180 and 255] of FIGS. 1G and 1J, respectively, point P may be used to locate the computer generated 3D models 22, 28, 36 created from the 2D knee coil images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D knee images 16.

As indicated in FIG. 1E, the 2D knee coil images 16 are segmented along the bone surface boundaries to generate 2D bone-only contour lines [Block 145]. The 2D knee coil images 16 are also segmented along cartilage and bone surface boundaries to generate 2D bone and cartilage contour lines [Block 245]. In one embodiment, the bone surface contour lines and cartilage-and-bone surface contour lines of the bones 18, 20 depicted in the 2D knee coil image slices 16 may be auto segmented via an image segmentation process as disclosed in U.S. patent application Ser. No. 12/386,105, which was filed Apr. 4, 2009, is titled System and Method for Image Segmentation in Generating Computer Models of a Joint to Undergo Arthroplasty, and is hereby incorporated by reference into the present application in its entirety.

As can be understood from FIG. 1F, the 2D bone-only contour lines segmented from the 2D knee coil images 16 are employed to create computer generated 3D bone-only (i.e., "bone models") 22 of the bones 18, 20 forming the patient's knee 14 [Block 150]. The bone models 22 are located such that point P is at coordinates $(X_{0-j}, Y_{0-j}, Z_{0-j})$ relative to an origin $(X_0, Y_0, Z_0)$ of the global coordinate system 63. In one embodiment, the bone models 22 incorporate the hip, knee and ankle centers 54, 56, 57, 58, and these centers 54, 56, 58 are positioned so as to reflect their correct respective locations with respect to the orientation and location of the bone models 22. In another embodiment, the hip, knee and ankle centers 54, 56, 57, 58 are not incorporated into the bone models 22, but are linked to the bone models 22 such that the hip, knee and ankle centers 54, 56, 57, 58 may be toggled on or off to display with the bone models 22 or be hidden. In such an embodiment, the hip, knee and ankle centers 54, 56, 57, 58 are positioned so as to reflect their correct respective locations with respect to the orientation and location of the bone models 22 when the centers 54, 56, 57, 58 are toggled on to be visible with the bone models 22.

Regardless of whether the centers 54, 56, 57, 58 are part of the bone models 22 or separate from the bone models 22 but capable of being shown with the bone models 22, the bone models 22 depict the bones 18, 20 in the present deteriorated condition with their respective degenerated joint surfaces 24, 26, which may be a result of osteoarthritis, injury, a combination thereof, etc. Also, the hip, knee and ankle centers 54, 56, 57, 58 and bone surfaces 24, 26 are positioned relative to each other as would generally be the case with the patient's long leg anatomy in the present deteriorated state. That the centers 54, 56, 57, 58 are correctly oriented with respect to the bone models 22 to represent the patient's long leg anatomy in the present deteriorated state is made possible, at least in part, via the transformation process described above with respect to [Blocks 125-135] of FIGS. 1D-1E and FIGS. 8-13.

In one embodiment, the systems and methods disclosed herein create the 3D computer generated bone models 22 from the bone-only contour lines segmented from the 2D knee coil images 16 via the systems and methods described in U.S. patent application Ser. No. 12/386,105, which was filed Apr. 4, 2009, is entitled System and Method for Image Segmentation in Generating Computer Models of a Joint to Undergo Arthroplasty, and is hereby incorporated by reference into the present application in its entirety. In other embodiments the systems and methods disclosed herein employ any one or more of the following computer programs to create the 3D computer generated bone models 22 from the bone-only contour lines segmented from the 2D knee coil images 16: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

As indicated in FIG. 1F, the 3D computer generated bone models 22, or associated bone-only contour lines, are utilized to create 3D computer generated "restored bone models" or "planning bone models" 28 wherein the degenerated surfaces 24, 26 are modified or restored to approximately their respective conditions prior to degeneration [Block 155]. Thus, the bones 18, of the restored bone models 28 and their respective restored bone surfaces 24', 26' are reflected in approximately their condition prior to degeneration. The restored bone models 28 are located such that point P is at coordinates $(X_{0-j}, Y_{0-j}, Z_{0-j})$ relative to the origin $(X_0, Y_0, Z_0)$ of the global coordinate system 63. Thus, the restored bone models 28 share the same orientation and positioning relative to the origin $(X_0, Y_0, Z_0)$ of the global coordinate system 63 as the bone models 22.

As with the bone models 22 discussed above, the hip, knee and ankle centers 54, 56, 57, 58 may be incorporated into the restored bone models 28 or stored separately from the restored bone models 28, but capable of being toggled on or off to be displayed relative to the restored bone models 28 or hidden.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the above-described bone restoration process is generally or completely automated, as disclosed in U.S. patent application Ser. No. 12/111,924 to Park, which is titled Generation of a Computerized Bone Model Representative of a Pre-Degenerated State and Usable in the Design and Manufacture of Arthroplasty Devices, was filed Apr. 29, 2008 and is incorporated by reference in its entirety into this Detailed Description. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state.

As depicted in FIG. 1F, once the restored bone models 28 have been generated as discussed above with respect to [Block 155], the restored bone models 28 are employed in a pre-operative planning ("POP") procedure to determine saw cut (bone resection) locations 30 and drill hole locations 32 in the patient's bones that will allow the arthroplasty joint implants to generally restore the patient's joint line to its pre-degenerative alignment. Specifically, the POP process begins by moving the restored bone models 28 to the location of 3D models 34 of arthroplasty implant models proposed for use in the actual arthroplasty procedure [Block 160]. In moving the restored bone models 28 to the implant models 34, point p on the restored bone models 28 moves from coordinates $(X_{0-j}, Y_{0-j}, Z_{0-j})$ to coordinates $(X_{0-k}, Y_{0-k}, Z_{0-k})$ and becoming point P'. The implant models 34 include planar surfaces representative of the planar surfaces of the actual implants that intersect resected bone surfaces. These planar surfaces of the implant models 34 are used to determine resection or saw cut locations 30 during the POP. Also, the implant models 34 include screw holes representative of the screw holes of the actual implants that hold bone screws for retaining the actual implant in place on the resected bone. These holes of the implant models 34 are used to determine drill hole locations 32 during POP.

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. As can be understood from FIG. 1G, by superimposing the implant models 34 over the restored bone models 28, or vice versa, the joint surfaces of the implant models 34 can be aligned, shape fit, or otherwise caused to correspond with the joint surfaces of the restored bone models 28 [Block 165]. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. In one embodiment, the above-described POP process is generally or completely automated, as disclosed in U.S. patent application Ser. No. 12/563,809 to Park, which is titled Arthroplasty System and Related Methods, was filed Sep. 21, 2009 and is incorporated by reference in its entirety into this Detailed Description. In other words, a computer program may manipulate computer generated 3D implant models 34 (e.g., femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' $(X_{0-k}, Y_{0-k}, Z_{0-k})$ relative to the origin $(X_0, Y_0, Z_0)$ of the global coordinate system 63, and the restored bone models 28 are located at point P $(X_{0-j}, Y_{0-j}, Z_{0-j})$. To cause the joint surfaces of the models 28, 34 to correspond, the computer program may move the restored bone models 28 from point P $(X_{0-j}, Y_{0-j}, Z_{0-j})$ to point P' $(X_{0-k}, Y_{0-k}, Z_{0-k})$, or vice versa [Block 160]. Once the joint surfaces of the models 28, 34 are in close proximity, the joint surfaces of the implant models 34 may be shape-matched to align or correspond with the joint surfaces of the restored bone models 28 [Block 165]. By causing the joint surfaces of the models 28, 34 to so align, the implant models 34 are positioned relative to the restored bone models 28 such that the saw cut locations 30 and drill hole locations 32 can be determined relative to the restored bone models 28. As a result of this POP process, the resection locations 30 will be such that the actual implants will generally restore the patient's knee geometry to what it was prior to degeneration.

As depicted in FIG. 1G, in one embodiment, a joint gap analysis is conducted to adjust orientation of the restored bone models 28 and arthroplasty implant models 34 so the joint gap on each side of joint is generally equal, causing the joint line 64 to be generally parallel to floor and generally representative of the patient's pre-degenerative joint line 64 [Block 170]. Further detail regarding the joint gap analysis is provided in U.S. patent application Ser. No. 12/563,809 to Park, which is titled Arthroplasty System and Related Methods, was filed Sep. 21, 2009 and is incorporated by reference in its entirety into this Detailed Description.

As indicated in FIG. 1G, once the POP process is completed, a determination is made regarding the 3D location and/or orientation impact on the hip, knee and ankle center points 54, 56, 57, 58 on account of any of the processes of [Blocks 160, 165 & 170] or any other position and/or orientation change to the bone models 22 or restored bone models 28 [Block 175]. As discussed above with respect to [Block 135] of FIG. 1E, the location and orientation relationships between the hip, knee and ankle centers 54, 56, 57, 58 and the knee coil 2D images 16 are established. These location and orientation relationships between the hip, knee and ankle centers 54, 56, 57, 58 and the knee coil 2D images 16 and the descendant 3D bone models 22, 28 of the knee coil 2D images 16 are maintained throughout the various processes described herein. Thus, as indicated in FIG. 1C, the X, Y and Z global coordinate locations and/or orientations of each of the center points 54, 56, 57, 58 in "Table A" of [Block 115] are updated for any 3D location and/or orientation impact on the center points 54, 56, 57, 58 on account of any of the processes of [Blocks 160, 165 & 170] or any other location and/or orientation change to the 3D bone models 22 or restored bone models 28 [Block 120].

For example, after the joint gap analysis and manipulation is complete as recited in [Block 170], the coordinates for the joint centers of the restored 3D knee model are changed from $(x'_2, y'_2, z'_2)$ because of the manipulation of the models 28, 34 in bringing the joint line parallel to the ground. After completion of the joint gap analysis and manipulation, the joint line 64 is set up and is perpendicular to the center of distal femur and perpendicular to the center of proximal tibia. Such manipulation can be done for both the distal femur and proximal tibia. As a result, the coordinates of the joint centers of this newly aligned 3D knee model (with joint line references and joint center points) may be further identified and recorded as $(x''_2, y''_2, z''_2)$.

As indicated in FIG. 1G, once the POP process is completed, a determination is made regarding the change in the 3D location and/or orientation of the bone models 22 or restored bone models 28 on account of any of the processes of [blocks 160, 165, 170] or any other location and/or orientation change to the bone models 22 or restored bone models 28 [Block 180]. Such a determination is employed to update the location and orientation of the arthritic models 36, as discussed below in [Block 255] of FIG. 1J.

As illustrated in FIG. 1H, the hip, knee and ankle center points 54, 56, 57, 58 and femoral mechanical axis 68, tibial mechanical axis 70, and mechanical axis 72 are depicted in 3D with the 3D restored bone models 28 and 3D implant models 34 [Block 190]. This may be achieved where the center points 54, 56, 57, 58 are part of the 3D restored bone models 28 or the center points are separate from the restored bone models 28, but capable of being toggled on to be viewable in 3D with the restored bone models 28. The points 54, 56, 57, 58, axes 68, 70, 72, and models 28, 34 are presented in a coronal view [Block 190]. By employing the restored bone models 28 in the POP process and maintaining the proper location and orientation of the hip, knee and ankle centers 54, 56, 57, 58 during the POP process, the models 28, 34 and centers 54, 56, 57, 58 illustrate a general approximation of the patient's knee geometry prior to deterioration, both respect to the joint line 64 and the various axes 68m, 70, 72.

Figure 17:
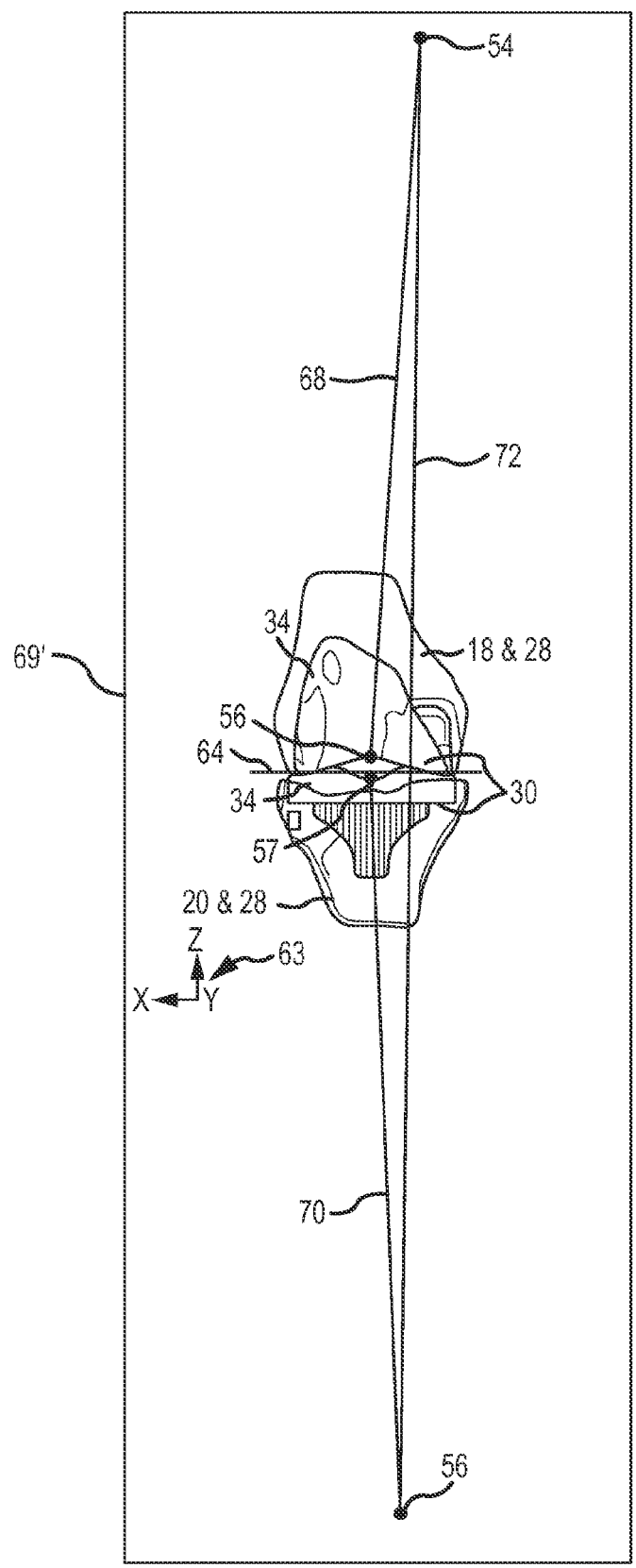
FIG. 17 is a coronal snapshot of the restored bone models, the implant models, the joint center points, and the femur mechanical axis, the tibia mechanical axis and the mechanical axis.

In one embodiment, a 2D coronal snapshot 69' of the models 28, 34, points 54, 56, 57, 58, and axes 68, 70, 72 is created [Block 195]. An example of such a coronal snapshot 69' is depicted in FIG. 17. Also, in one embodiment, a 2D coronal snapshot 69" of the models 28, points 54, 56, 57, 58, and axes 68, 70, 72, less the implant models 34, is created [Block 200]. Each of these snapshots 69', 69" depict the patient's joint geometry in natural alignment or, in other words, as the patient's joint geometry is believed to have generally existed prior to degeneration.

Figure 19:
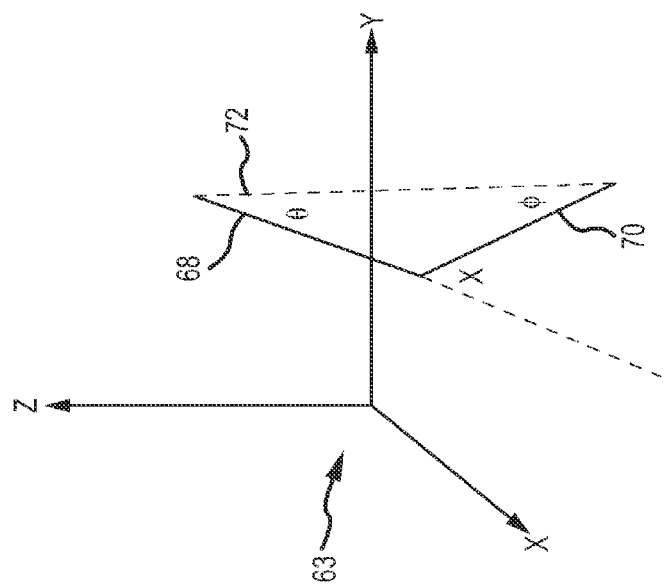
FIG. 19 is a diagrammatic depiction of the axes and their relationship to each other in the global coordinate system.
Figure 18:
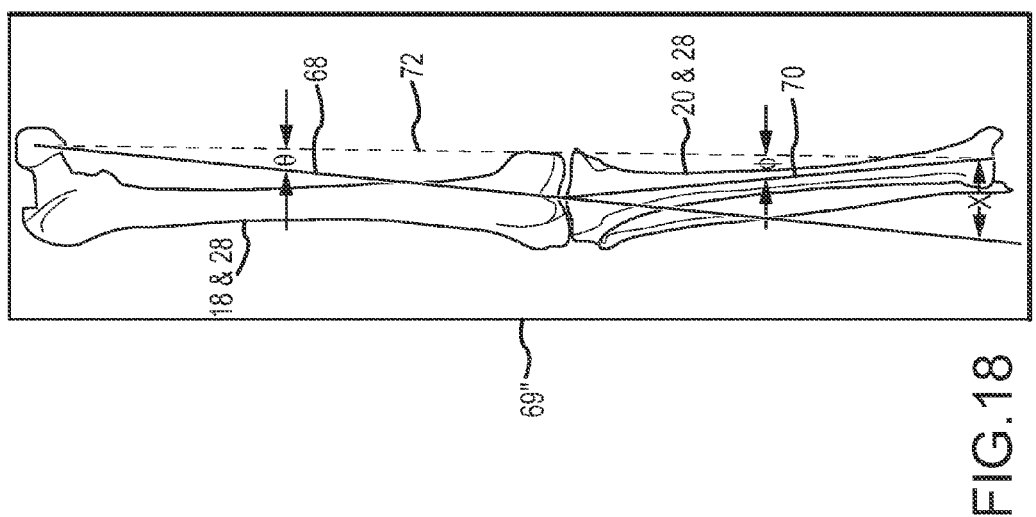
FIG. 18 is another version of the 2D coronal snapshot that may be provided to the physician.

FIG. 18 is another version of the 2D coronal snapshot 69''' that may be provided to the physician, and FIG. 19 is a diagrammatic depiction of the axes 68, 70, 72 and their relationship to each other in the global coordinate system 63. The snapshot 69''', which illustrates the natural alignment knee geometry and depicts the varus/valgus ("v/v") measurement, may be employed by the physician to determine the amount of correction needed to bring the knee geometry to a neutral geometry or a geometry between natural and neutral the physician considers desirable.

As shown in FIGS. 18 and 19, the v/v angle θ for the femur 18 is measured between the FMA 68 and MA 72. The FMA 68 is a line extending between the center of the femoral head to the center of the knee region of the femur 18. The v/v angle φ for the tibia 20 is measured between the TMA 70 and the MA 72. The TMA 70 is a line extending between the center of the ankle to the center of the knee region of the tibia 20. The MA 72 is a line extending between the center of the femoral head to the center of the ankle. When the knee geometry is in a zero degree mechanical axis or neutral geometry, the FMA 68, TMA 70 and MA 72 will be generally coextensively aligned with each other.

In one embodiment, if the v/v angles fall into an acceptable range wherein θ, φ<±3°, then the snapshot 69''' has an acceptable natural geometry and can be forwarded to the physician. If the v/v angles do not fall into an acceptable range wherein θ, φ<±3°, then the POP process is run again to arrive at a natural geometry that is acceptable.

As shown in FIGS. 18 and 19, the angle X approximately equal to the sum of angles θ and φ.

As indicated in FIG. 1I, in one embodiment, one more of the 2D coronal snapshots 69', 69", 69''' are provided to the physician for review [Block 205]. The physician reviews the proposed correction and associated natural alignment depicted in the received snapshot(s) 69', 69", 69''' and provides feedback regarding the proposed correction [Block 210]. If the physician approves of the proposed correction and associated natural alignment depicted in the received snapshot(s) 69', 69", 69''' [Block 215], then the proposed correction is left as is [Block 235].

However, as can be understood from FIG. 1I, if the physician disapproves of the proposed correction and associated natural alignment depicted in the received snapshot(s) 69', 69" [Block 215], then the proposed correction and associated natural alignment is adjusted in the X-Y (coronal) plane according to physician input [Block 225], the adjustment being made to the saw cut and drill hole locations 30, 32 of the 3D models 28, 34 of [Block 170]. In other words, the proposed correction and associated natural alignment is adjusted to a new proposed correction, wherein the new proposed correction is associated with a zero degree mechanical axis (neutral) alignment or an alignment somewhere between the originally proposed natural alignment and a neutral alignment.

Figure 20:
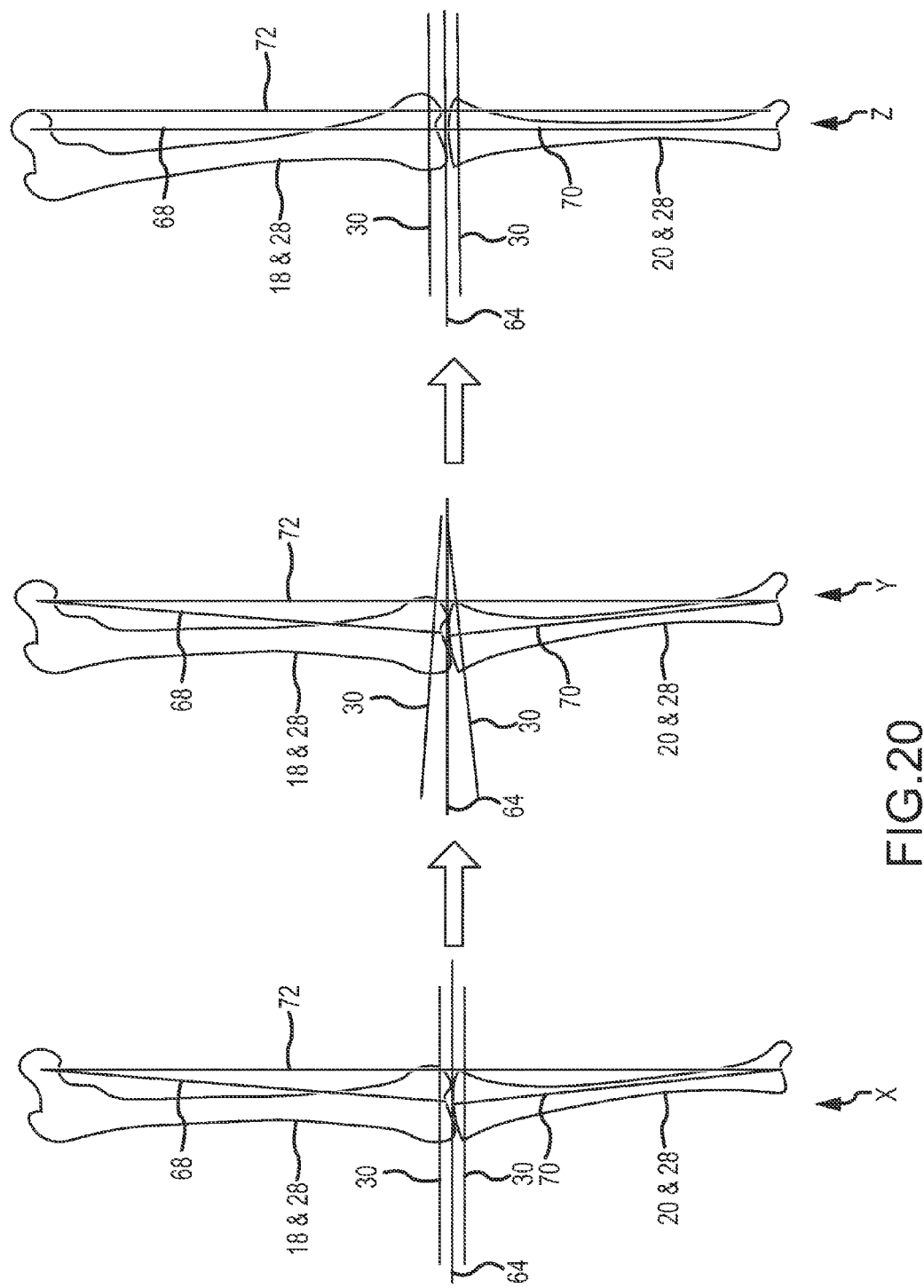
FIG. 20 is a diagrammatic depiction of a process of adjusting resection lines based on joint geometry information conveyed via the 2D coronal snapshots.

As can be understood from FIG. 20, which is a diagrammatic depiction of a process of adjusting resection lines based on joint geometry information conveyed via the 2D coronal snapshots 69', 69'', 69''', the knee joint geometry is depicted in natural alignment at X, the joint line 64 being generally parallel to the ground and the FMA 68 and TMA 70 being angled relative to the MA 72. Upon review, the physician may determine the resection lines 30 in image X should be adjusted to be as indicated in images Y to cause the knee joint geometry to assume an alignment that is closer to neutral. As shown in image Z, where the resection lines 30 have been adjusted per the physician's direction and the bones 18, 20 realigned, the joint line 64 is generally parallel to the floor and the FMA 68 and TMA 70 are generally parallel to the MA 72, which is shown off of the bones 18, 20 for clarity purposes.

Thus, in summary of the events at [Block 215] of FIG. 1I, the physician may determine that the natural alignment is desirable and, as a result, the alignment of the restored bone model 28 is not changed [Block 235], or the physician may determine that the restored bone model 28 should be realigned from natural alignment to an alignment that is closer to zero degree mechanical axis [Block 225].

If the alignment is updated as in [Block 225], then per [Block 230], the 2D coronal snapshots 69', 69'' of [Blocks 195 and 200] are regenerated off of the models 28, 34 of [Block 170] as updated per [Block 225]. The updated coronal snapshots 69', 69'' are again sent to the physician [Block 205] and the process repeats itself as recited above with respect to [Blocks 210-230], until the physician agrees with the proposed correction [Block 215] and the proposed correction is found to be desirable, no further correction being deemed necessary by the physician [Block 235].

As indicated in FIG. 1K, in one embodiment, the data 44 regarding the saw cut and drill hole locations 30, 32 relative to point P' ($X_{0-k}$, $Y_{0-k}$, $Z_{0-k}$) is packaged or consolidated as the "saw cut and drill hole data" 44 [Block 240]. The "saw cut and drill hole data" 44 is then used as discussed below with respect to [Block 270] in FIG. 1K.

As mentioned above with respect to FIG. 1E, the 2D knee coil images 16 are segmented along cartilage and bone boundaries to generate 2D bone and cartilage contour lines [Block 245]. As can be understood from FIG. 1J, the bone and cartilage contour lines are used to create computer generated 3D bone and cartilage models (i.e., "arthritic models") 36 of the bones 18, 20 forming the patient's joint 14 [Block 250]. Like the above-discussed bone models 22, the arthritic models 36 are located such that point P is at coordinates ($X_{0-j}$, $Y_{0-j}$, $Z_{0-j}$) relative to the origin ($X_0$, $Y_0$, $Z_0$) of the global coordinate system 63 [Block 190]. Thus, the bone and arthritic models 22, 36 share the same location and orientation relative to the origin ($X_0$, $Y_0$, $Z_0$) of the global coordinate system 63. This position/orientation relationship is generally maintained throughout the process discussed with respect to FIGS. 1E-1K. Accordingly, reorientations or movements relative to the origin ($X_0$, $Y_0$, $Z_0$) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1J and already mentioned above, to coordinate the positions/orientations of the bone and arthritic models 22, 36 and their respective descendants, any reorientation or movement of the restored bone models 28 from point P to point P' is tracked to cause a generally identical displacement for the "arthritic models" 36 [Block 255]. Thus, for any change in the 3D position or orientation of the bone models 22 or restored bone models 28 on account of any of the processes of [Blocks 160, 165, 170] or any other position or orientation change to the bone models 22 or restored bone models 28 (e.g., the bone models 22 or restored bone models 28 being reoriented at or moved from point P at coordinates ($X_{0-j}$, $Y_{0-j}$, $Z_{0-j}$) to point P' at coordinates ($X_{0-k}$, $Y_{0-k}$, $Z_{0-k}$)), an identical movement is caused in the 3D arthritic models 36 such that the location and orientation of arthritic models 36 match those of the bone models 22 and restored bone models 28.

As depicted in FIG. 1J, computer generated 3D surface models 40 of the arthroplasty target areas 42 of the arthritic models 36 are imported into computer generated 3D arthroplasty jig models 38 [Block 260]. Thus, the jig models 38 are configured or indexed to matingly (matchingly) receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly (matchingly) receive the arthroplasty target areas 42 of the arthritic models 36. Point P' ($X_{0-k}$, $Y_{0-k}$, $Z_{0-k}$) can also be imported into the jig models 38, resulting in jig models 38 positioned and oriented relative to point P' ($X_{0-k}$, $Y_{0-k}$, $Z_{0-k}$) to allow their integration with the bone cut and drill hole data 44 of [Block 240].

In one embodiment, the procedure for indexing the jig models 38 to the arthroplasty target areas 42 is generally or completely automated, as disclosed in U.S. patent application Ser. No. 11/959,344 to Park, which is titled System and Method for Manufacturing Arthroplasty Jigs, was filed Dec.

18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the jig models 38, resulting in the jig models 38 being indexed to matingly receive the arthroplasty target areas 42 of the arthritic models 36. The resulting jig models 38 are also positioned and oriented relative to point P' ($X_{0-k}$, $Y_{0-k}$, $Z_{0-k}$) to allow their integration with the bone cut and drill hole data 44 of [Block 240].

In one embodiment, the arthritic models 36 may be 3D volumetric models as generated from the closed-loop process discussed in U.S. patent application Ser. No. 11/959,344 filed by Park. In other embodiments, the arthritic models 36 may be 3D surface models as generated from the open-loop process discussed in U.S. patent application Ser. No. 11/959,344 filed by Park.

In one embodiment, the models 40 of the arthroplasty target areas 42 of the arthritic models 36 may be generated via an overestimation process as disclosed in U.S. Provisional Patent Application 61/083,053, which is titled System and Method for Manufacturing Arthroplasty Jigs Having Improved Mating Accuracy, was filed by Park Jul. 23, 2008, and is hereby incorporated by reference in its entirety into this Detailed Description.

As indicated in FIG. 1K, in one embodiment, the data regarding the jig models 38 and surface models 40 relative to point P' ($X_{0-k}$, $Y_{0-k}$, $Z_{0-k}$) is packaged or consolidated as the "jig data" 46 [Block 265]. The "jig data" 46 is then used as discussed below with respect to [Block 270] in FIG. 1K.

As can be understood from FIG. 1K, the "saw cut and drill hole data" 44 is integrated with the "jig data" 46 to result in the "integrated jig data" 48 [Block 270]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to achieve a joint alignment that is: (1) generally representative of the patient's pre-degenerative joint line (i.e., natural alignment); generally corresponding to a zero mechanical axis alignment; or (3) somewhere between (1) and (2), depending the input the physician provided in the process discussed above with respect in FIG. 1I.

As can be understood from FIGS. 1A and 1K, the "integrated jig data" 48 is transferred from the computer 6 to the CNC machine 10 [Block 275]. Jig blanks 50 are provided to the CNC machine 10 [Block 280], and the CNC machine 10 employs the "integrated jig data" to machine the arthroplasty jigs 2 from the jig blanks 50 [Block 285].

Figure 2A:
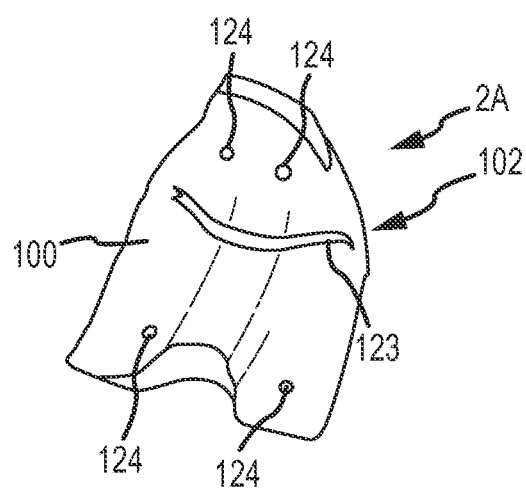
FIGS. 2A and 2B are, respectively, bottom and top perspective views of an example customized arthroplasty femur jig.
Figure 3A:
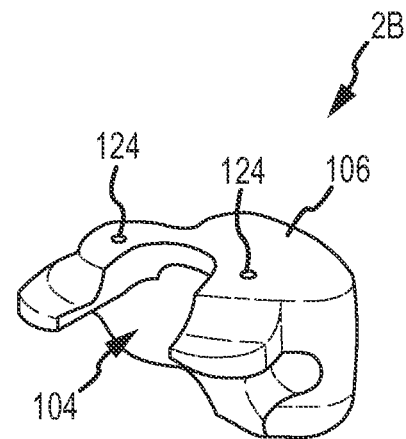
FIGS. 3A and 3B are, respectively, bottom and top perspective views of an example customized arthroplasty tibia jig.
Figure 2B:
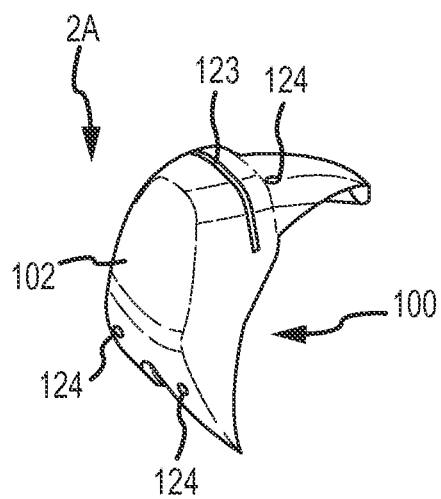
Figure 3B:
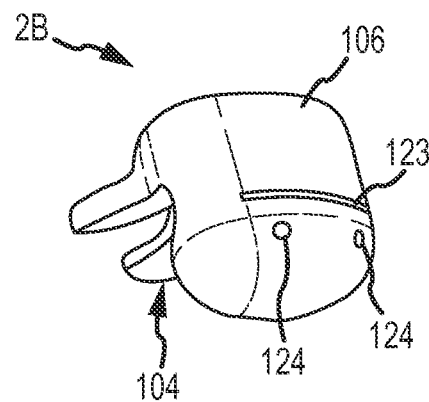

For a discussion of example customized arthroplasty cutting jigs 2 capable of being manufactured via the above-discussed process, reference is made to FIGS. 2A-3B. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 2A-3B are for total knee replacement ("TKR") or partial knee ("uni-knee") replacement procedures. Thus, FIGS. 2A and 2B are, respectively, bottom and top perspective views of an example customized arthroplasty femur jig 2A, and FIGS. 3A and 3B are, respectively, bottom and top perspective views of an example customized arthroplasty tibia jig 2B.

As indicated in FIGS. 2A and 2B, a femur arthroplasty jig 2A may include an interior side or portion 100 and an exterior side or portion 102. When the femur cutting jig 2A is used in a TKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR surgery, the surfaces of the target area 42 and the interior portion 100 match. In other words, the surface of the interior portion 100 of the femur jig 2A is generally a negative of the target area 42 of the patient's femur 18 and will matingly or matchingly receive the target area 42.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 3A and 3B, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match. In other words, the surface of the interior portion 104 of the tibia jig 2B is generally a negative of the target area 42 of the patient's tibia 20 and will matingly or matchingly receive the target area 42.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

Another embodiment of the methods and systems for manufacturing the jigs 2A, 2B will now be described, the another embodiment having a shorthand designation of "MA alignment", wherein the embodiment described above with respect to FIGS. 1A-20 can have a shorthand designation of "natural alignment". The MA alignment embodiment is configured to provide a post surgical joint alignment that is generally a zero mechanical axis alignment. For the MA alignment embodiment, the methods and systems for manufacturing the jigs 2A, 2B are generally the same as described above with respect to the natural alignment embodiment, except the POP for the MA alignment embodiment does not first calculate a post surgical joint alignment that is (1) generally representative of the patient's pre-degenerative joint line and then allowing the surgeon to keep such an alignment or modify the alignment to correspond (2) generally to a zero mechanical axis alignment or (3) an alignment that is somewhere between (1) and (2). Instead, the MA alignment embodiment has POP that first achieves a post surgical joint alignment that is generally representative of a zero mechanical axis alignment and then allows the surgeon to keep such an alignment or modify the alignment as desired.

The MA alignment embodiment begins by following generally the same process as described above with respect to FIGS. 1A-1E, arriving at Block 145 and Block 245 of FIG. 1E, wherein the knee coil 2D images 16 are segmented along bone boundaries to generate 2D bone-only contour lines [Block 145] and segmented along cartilage and bone boundaries to generate 2D bone and cartilage contour lines [Block 245]. As can be understood from FIGS. 1F and 1J, the 2D bone-only contour lines are then used to generate the 3D bone models (i.e., planning models) 22 [Block 150], and the 2D bone and cartilage contour lines are used to generate the 3D bone and cartilage models (i.e., arthritic models) 36 [Block 250]. Before being used to generate the 3D arthritic models 36, the 2D bone and cartilage contour lines generated during Block 245 are subjected to an overestimation process as disclosed in U.S. Non-Provisional patent application Ser. No. 12/505,056, which is titled System and Method for Manufacturing Arthroplasty Jigs Having Improved Mating Accuracy, was filed by Park Jul. 17, 2009, and is hereby incorporated by reference in its entirety into this Detailed Description.

Figure 21:
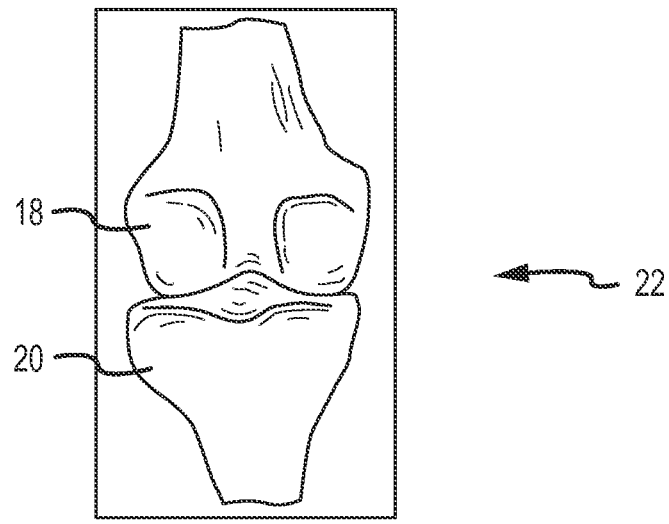
FIG. 21 is coronal view of 3D planning or bone models.
Figure 22:
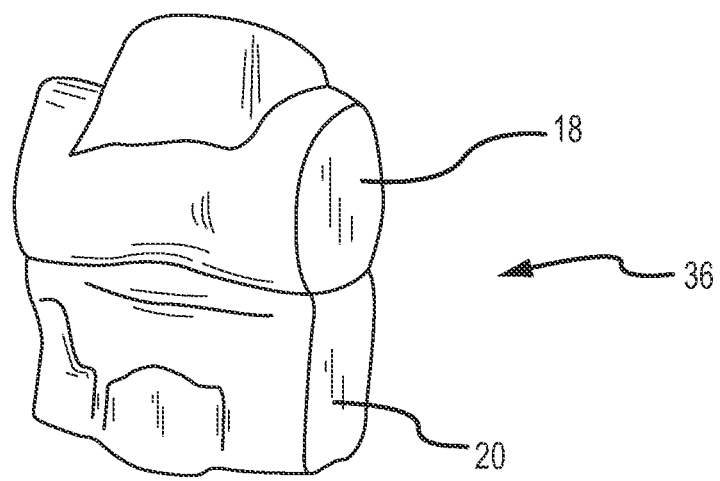
FIG. 22 is a coronal-sagittal isometric view of 3D overestimated arthritic models.

FIG. 21 shows an example of 3D bone models 22 resulting from the 2D bone-only contour lines. FIG. 22 shows an example of the 3D arthritic models 36 resulting from the overestimated 2D bone and cartilage contour lines. Due to the overestimation process applied to the bone and cartilage contour lines, surfaces of the arthritic models 36 are overestimated (i.e., pushed outwardly from the interior of the model 36) in regions of the model 36 that correspond to (1) regions of the images that are associated with low accuracy due to limitations in the imaging processes or (2) regions of the model that are unlikely to be manufactured accurately into a jig blank due to limitations of, for example, the milling process.

Figure 23:
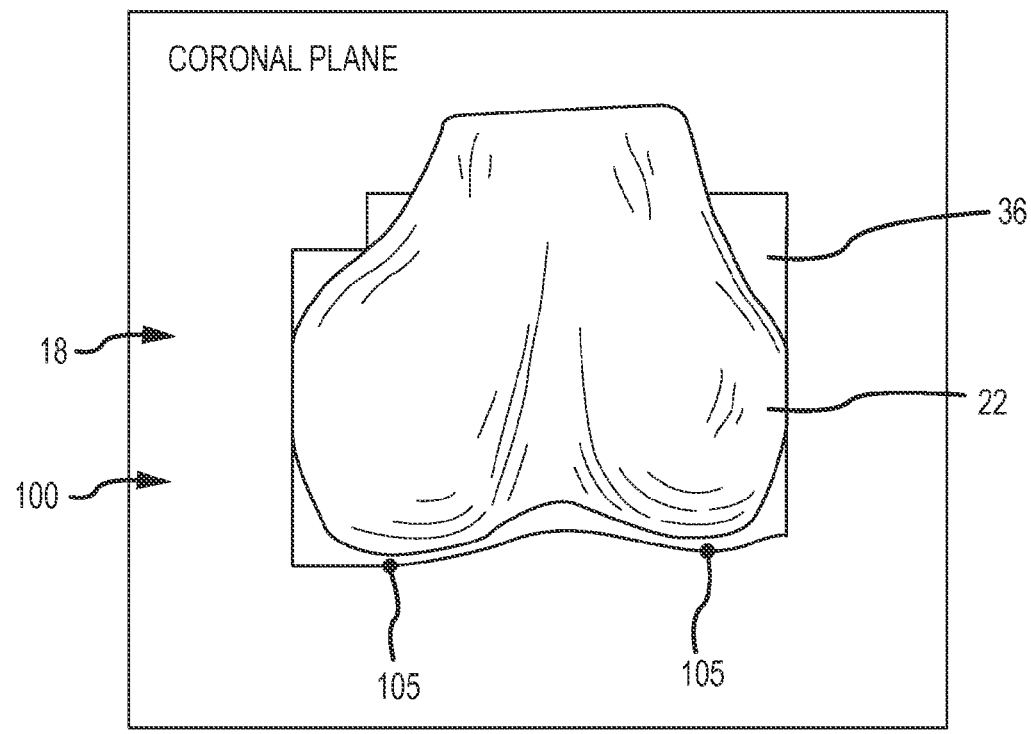
FIG. 23 is a coronal view of a 3D femoral superimposed model formed of the 3D femoral bone and overestimated arthritic models superimposed.
Figure 24:
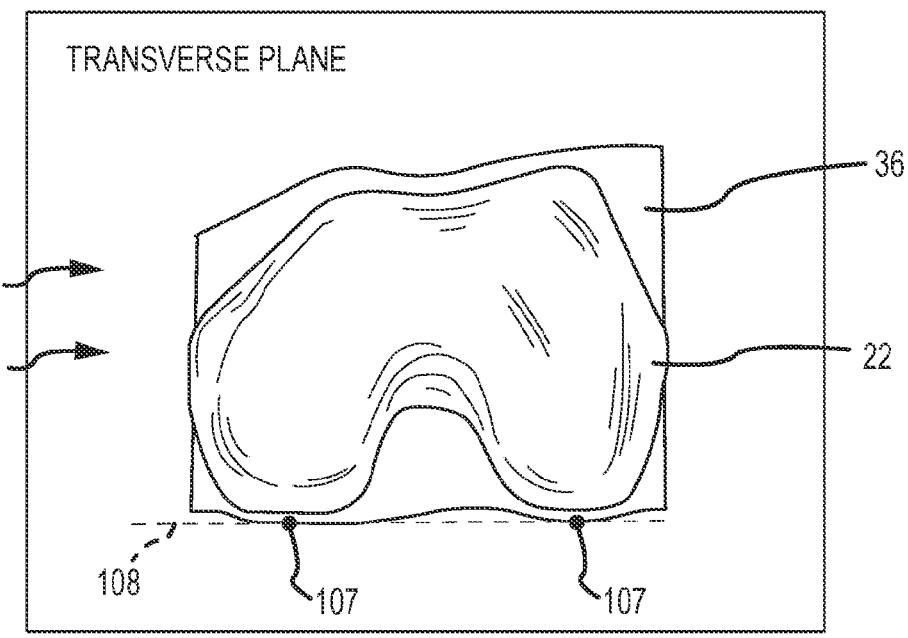
FIG. 24 is an axial view of the 3D femoral superimposed model of FIG. 23.

As can be understood from FIGS. 23 and 24, which are, respectively, coronal and axial views of the models 22, 36 of the femur 18, the femoral models 22, 36 are superimposed to begin the POP process of the MA alignment embodiment. Similarly, as can be understood from FIGS. 25 and 26, which are, respectively, coronal and axial views of the models 22, 36 of the tibia 20, the tibial models 22, 36 are superimposed to begin the POP process of the MA alignment embodiment. In other words, POP for the MA alignment embodiment employs both the bone models 22 and the arthritic models 36. The bone models 22 identify the cortical and subchondral bone boundaries, and the arthritic models 36 identify the cartilage boundaries. By employing both types of models 22, 36, the full definition of the knee anatomy is achieved with distinct cartilage and bony anatomical landmarks for the femur 18 and tibia 20. From here on in this discussion regarding the MA alignment embodiment, the models 22, 26 when superimposed together for purposes of POP will be referred to as superimposed models 100.

As indicated in FIG. 23, a most distal femoral condylar point 105 is identified on each of the condyles of the femoral arthritic model 36 of the femoral superimposed model 100. Similarly, as indicated in FIG. 24, a most posterior point 107 is identified on each of the condyles of the femoral arthritic model 36 of the femoral superimposed model 100. A posterior condylar line 108 connects the most posterior condylar points 107.

Figure 25:
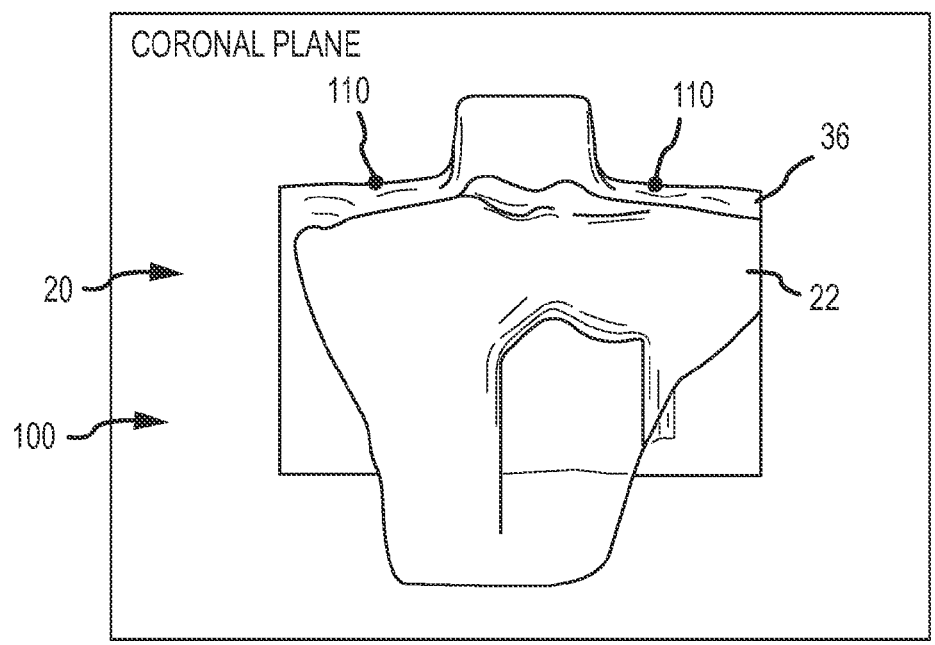
FIG. 25 is a coronal view of a 3D tibial superimposed model formed of the 3D tibial bone and overestimated arthritic models superimposed.
Figure 26:
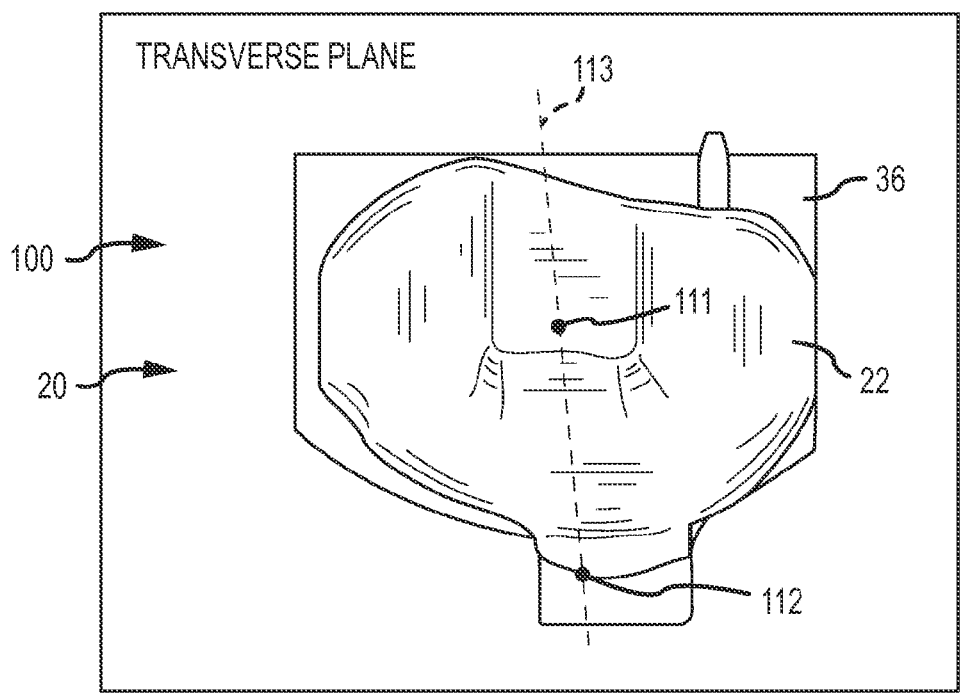
FIG. 26 is an axial view of the 3D tibial superimposed model of FIG. 25.

As indicated in FIG. 25, a most proximal tibial condylar point 110 is identified on each of the condyles of the tibial arthritic model 36 of the tibial superimposed model 100. As indicated in FIG. 26, a center point 111 of the tibial plateau and a point 112 at the medial third of the tibial tuberosity are identified on the bone model 22 of the femoral tibial superimposed model 100. A rotational tibial reference line 113 connects the points 111 and 112.

Figure 1L:
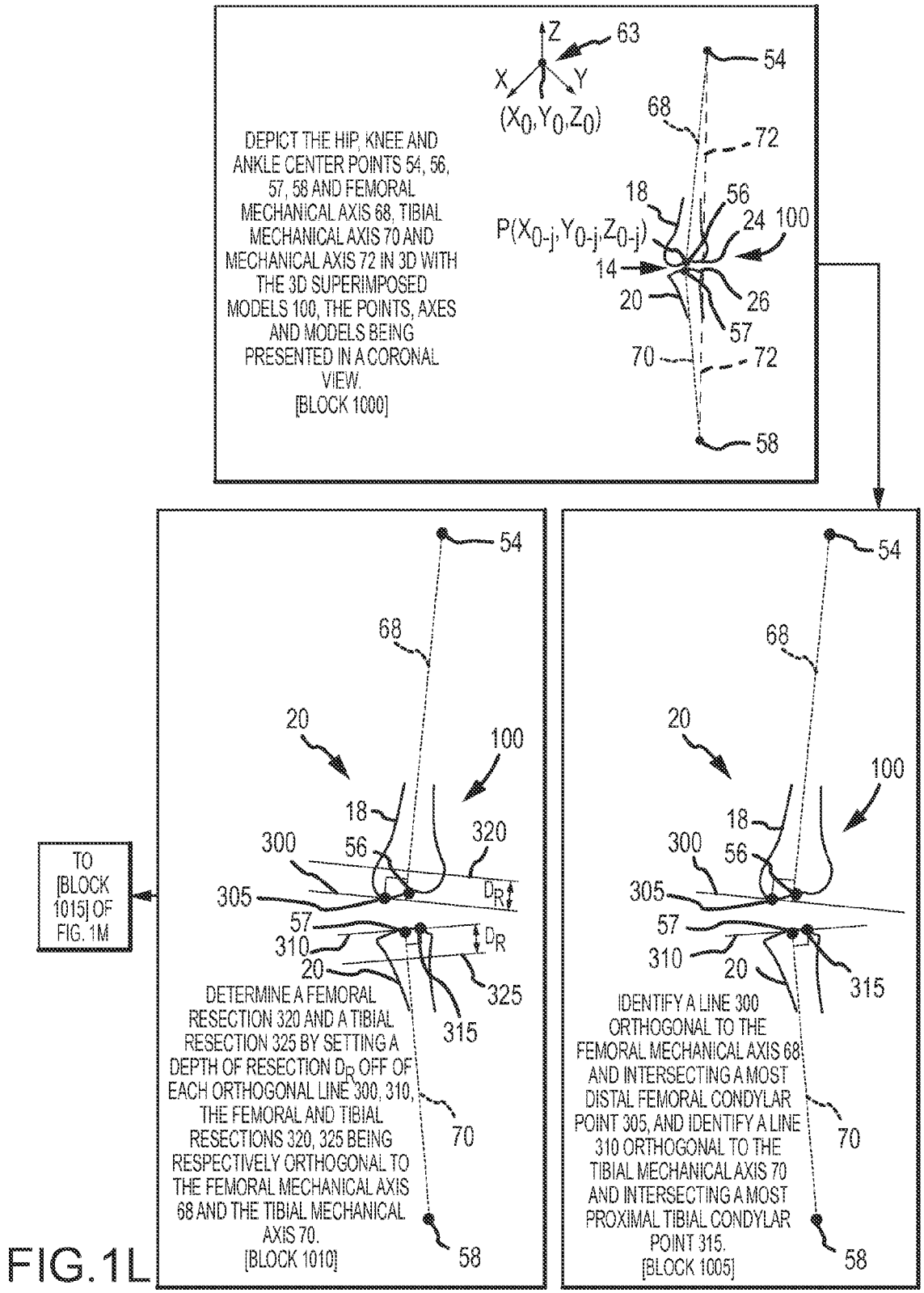
FIGS. 1L-1M are flow chart diagrams outlining an alternative embodiment of a portion of the jig production method disclosed herein.

As can be understood from FIG. 1L, the hip, knee and ankle center points 54, 56, 57, 58 and the femoral mechanical axis 68, tibial mechanical axis 70 and mechanical axis 72 are depicted in 3D with the 3D superimposed models 100 presented in a coronal view [Block 1000]. The center points 54, 56, 57 and 58 are obtained and positionally referenced to the models 100 as discussed above with respect to FIGS. 1A-1E.

As can be understood from FIG. 1L, a most distal point 305 of the two distal femoral condylar points 105 identified in FIG. 23 is identified, and a line 300 orthogonal to the femoral mechanical axis 68 and intersecting the most distal femoral condylar point 305 is provided [Block 1005]. Similarly, a most proximal point 315 of the two proximal tibial condylar points 110 identified in FIG. 25 is identified, and a line 310 orthogonal to the tibial mechanical axis 70 and intersecting the most proximal tibial condylar point 305 is provided [Block 1005].

As indicated in FIG. 1L, a femoral resection plane 320 and a tibial resection plane 325 are determined by setting a depth of resection $D_R$ off of each orthogonal line 300, 310, the femoral and tibial resection planes 320, 325 being respectively orthogonal to the femoral mechanical axis 68 and the tibial mechanical axis 70 in the coronal view [Block 1010]. The superior/inferior translation is now established for the POP.

In one embodiment, the depth of resection $D_R$ for the femur may be approximately 8 mm, plus or minus 1-3 mm depending on the depth of the implant intended to be implanted. For example, the depth of resection $D_R$ for the femur may be based on the thickness of the femoral implant form the most distal point of the medial or lateral condyle to the other side of the flange.

In one embodiment, the depth of resection $D_R$ for the tibia may be approximately 11 mm, plus or minus 1-3 mm depending on the depth of the implant intended to be implanted. For example, the depth of resection $D_R$ for the tibia may be based on the thickness of the tibia implant form the most proximal point of the medial or lateral condyle to the other side of the base plate and its liner.

Figure 27:
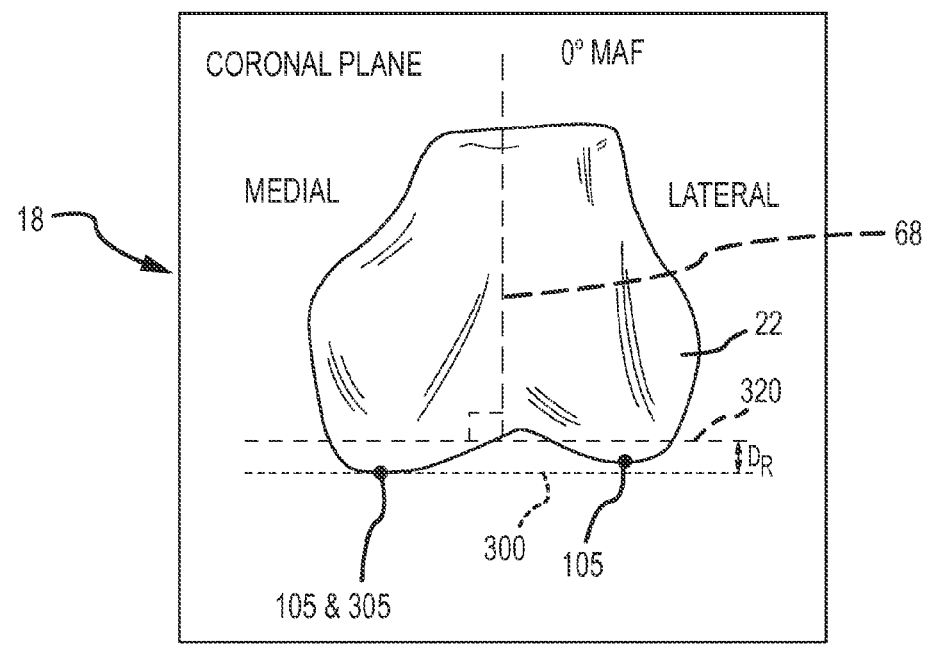
FIG. 27 is a coronal view of the 3D femoral bone model with the superior/inferior depth of resection depicted to achieve the desired varus/valgus resection orientation.
Figure 28:
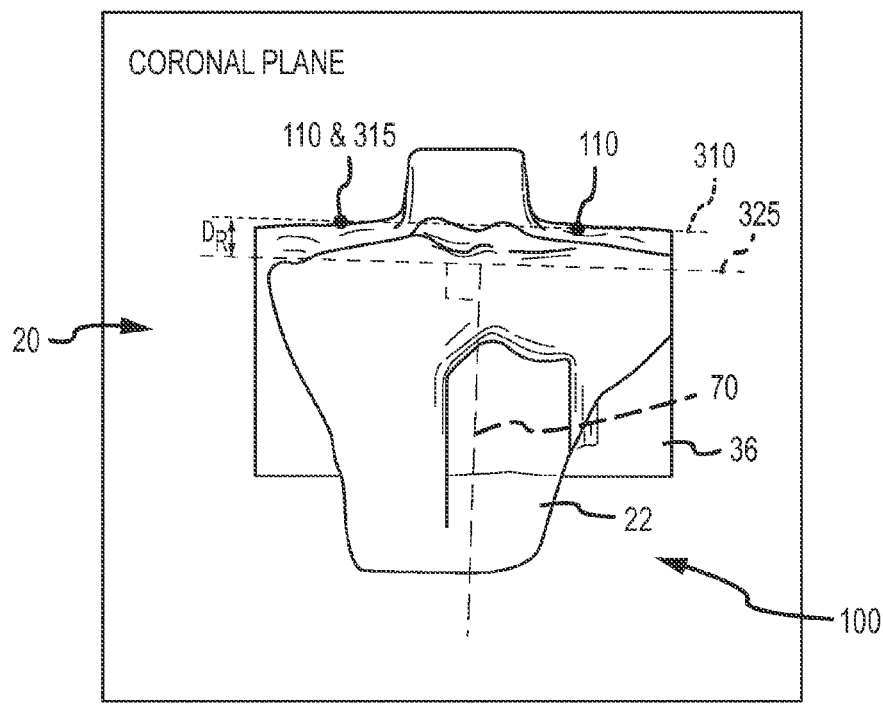
FIG. 28 is a coronal view of the 3D tibial superimposed model (i.e., 3D tibial bone model superimposed with the 3D tibial arthritic model) with the superior/inferior depth of resection depicted to achieve the desired varus/valgus resection orientation.

FIG. 27 is an enlarged coronal view of the femoral bone model 22 illustrating the results of the operations of Blocks 1000-1010 in FIG. 1L with respect to the femur 18. FIG. 28 is an enlarged coronal view of the tibial superimposed model 100 illustrating the results of the operations of Blocks 1000-1010 in FIG. 1L with respect to the tibia 18.

Figure 29:
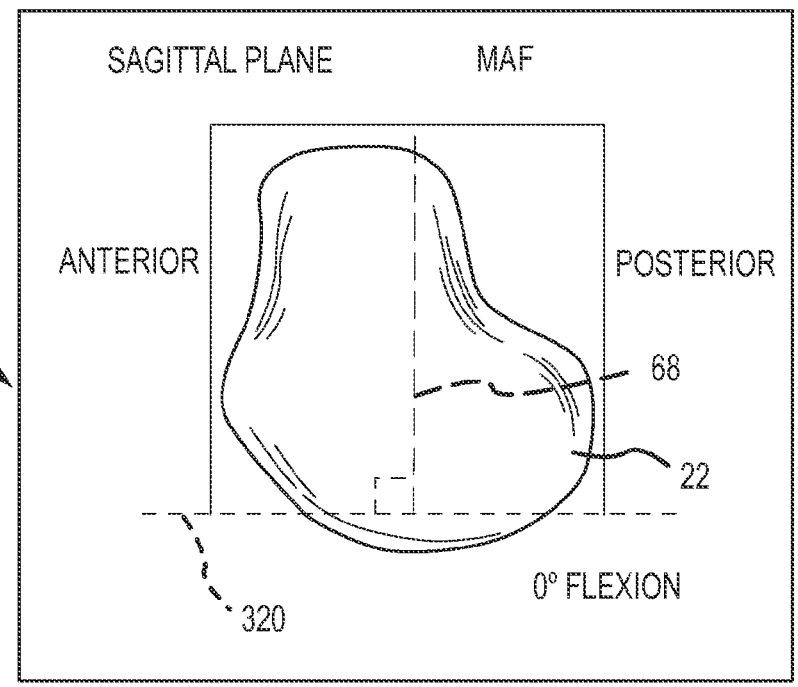
FIG. 29 is a sagittal view of the 3D femoral bone model with the flexion/extension orientation depicted.
Figure 30:
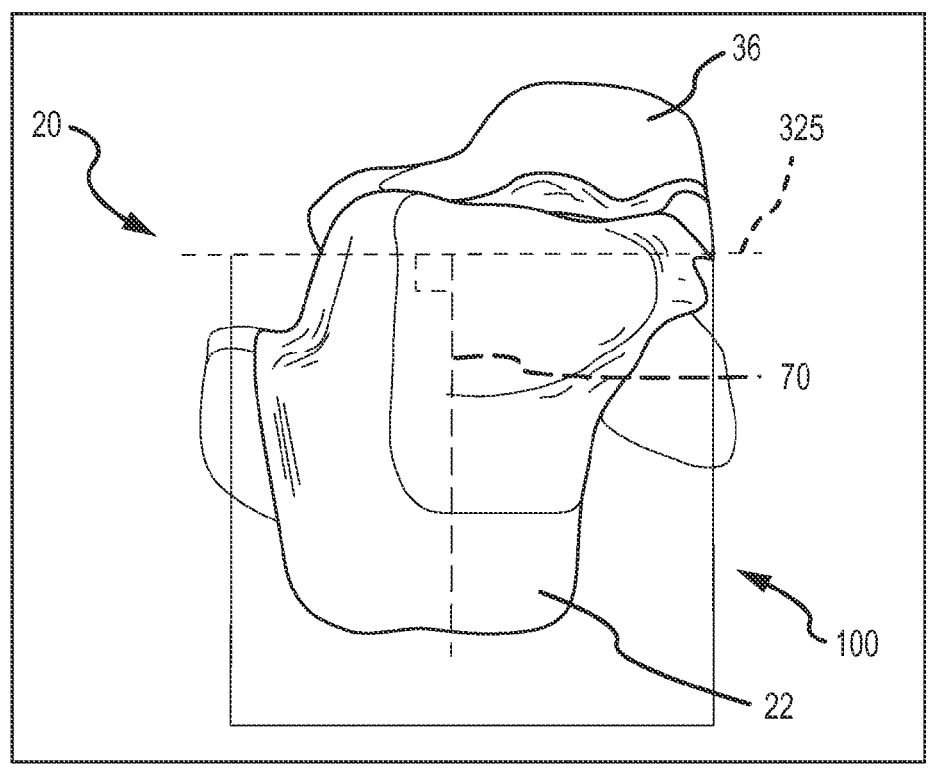
FIG. 30 is a sagittal view of the 3D tibial superimposed model with the flexion/extension orientation depicted.

As can be understood from FIG. 29, which is a sagittal view of the femoral bone model 22, the femoral resection plane 320 is caused to be orthogonal to the femoral mechanical axis 68 in the sagittal view. Similarly, as can be understood from FIG. 30, which is a sagittal view of the tibial superimposed model 100, the tibial resection plane 325 is caused to be orthogonal to the tibial mechanical axis 70 in the sagittal view. The flexion/extension orientations for both the femur 18 and tibia 20 have now been established for the POP. Variations to flexion/extension orientation can be made via the implant sizing operations as described below.

Figure 31:
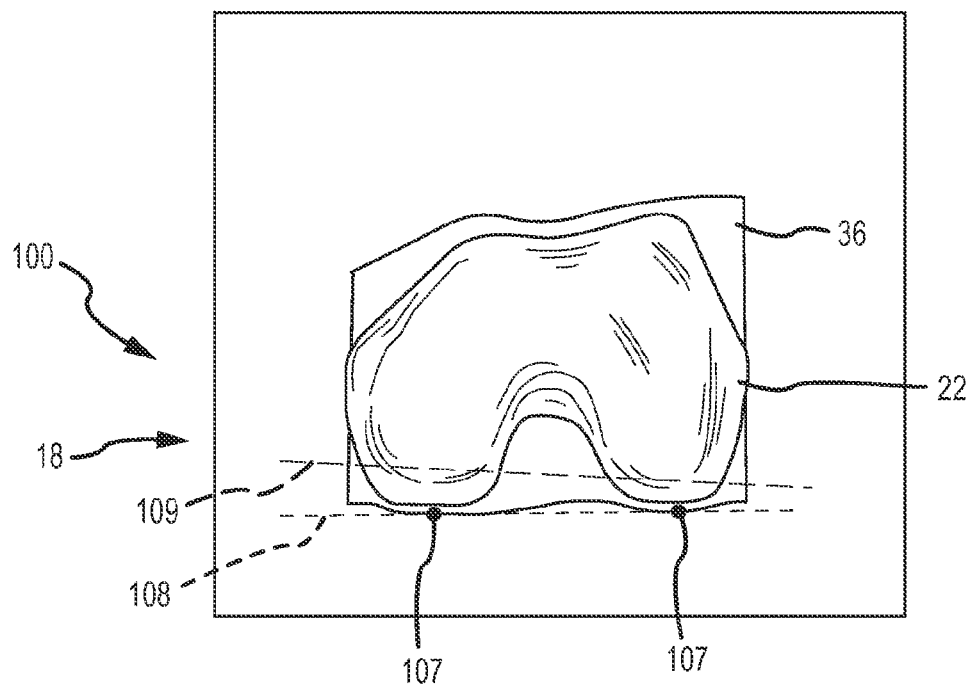
FIG. 31 is an axial or transverse view of the 3D femoral bone model with the external/internal orientation depicted.

As indicated in FIG. 31, which is the same axial view of the femur superimposed model 100 as shown in FIG. 24, an external rotation of approximately three degrees (plus or minus a degree or so, depending on the implant intended to be implanted) is provided, as can be understood from the angular difference between lines 108 and 109. Specifically, the implant is rotated externally the desired amount from the previously identified posterior condylar line 108 about the center of the implant. The internal/external rotational orientation for the femur 18 has now been established for the POP.

As can be understood from FIG. 26, external rotation can be visualized off of the medial one third of the tibial tubercle identified by point 112. Specifically, from the previously identified tibial rotational reference (i.e., the medial one third of the tibial tubercle indicated by point 112), the tibial implant is aligned with the rotational reference. The internal/external rotational orientation for the tibia 20 has now been established for the POP.

Figure 1M:
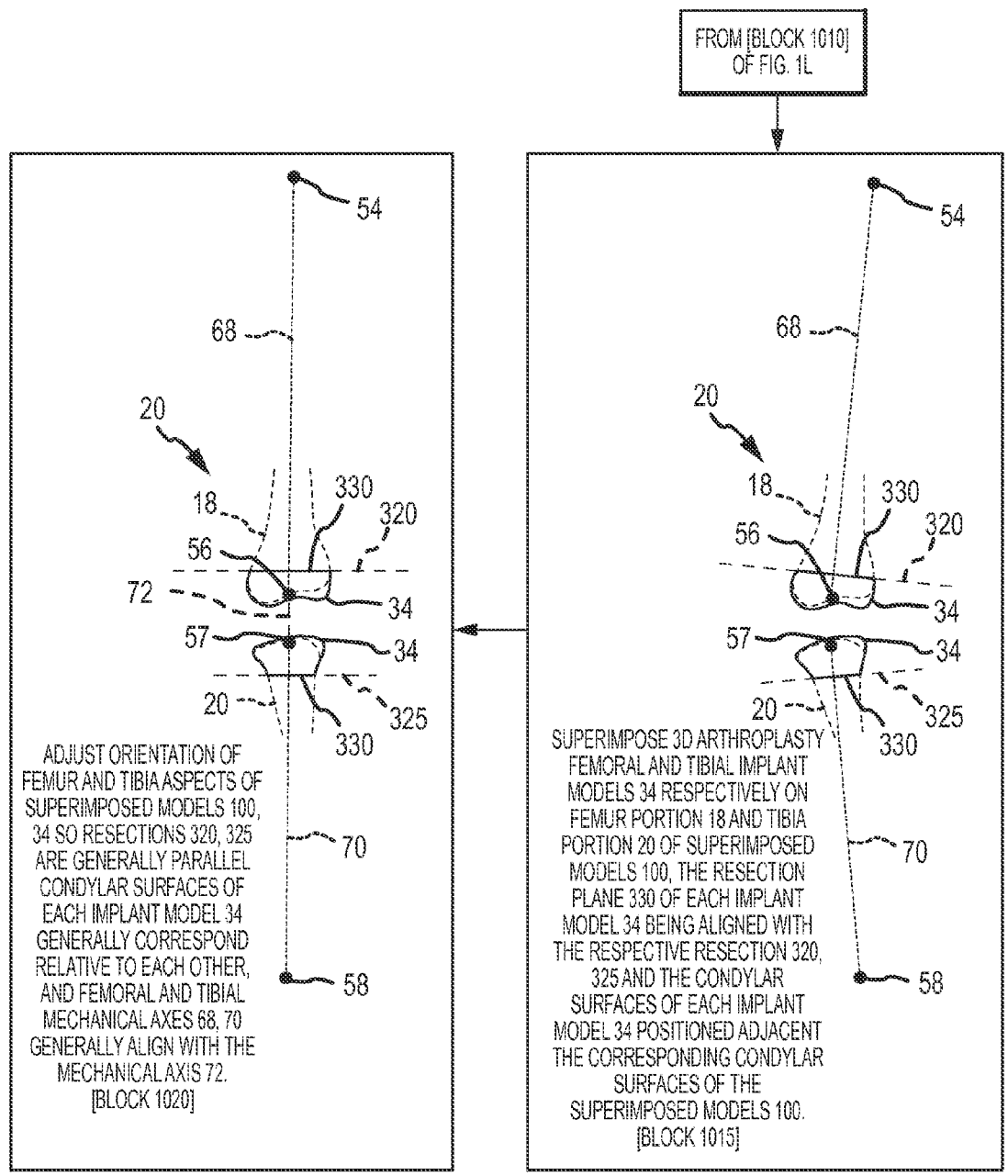

As shown in FIG. 1M, 3D arthroplasty femoral and tibial implant models 34 are respectively superimposed on the femur portion 18 and tibia portion 20 of the superimposed models 100 [Block 1015]. In doing so, the resection plane 330 of each implant model 34 is aligned with the respective resection line 320, 325 and orthogonal to the respective mechanical axis 68, 70. Since the depth of resection $D_R$ is based off of the dimension of the candidate implant, the condylar surfaces of each implant model 34 end up being positioned adjacent the corresponding condylar surfaces of the superimposed models 100 [Block 1015].

Figure 32:
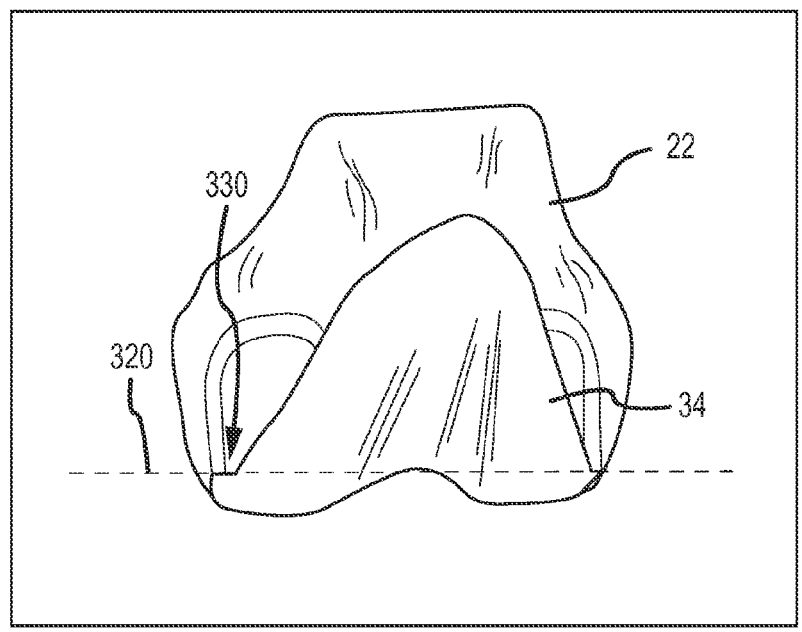
FIG. 32 is a coronal view of the 3D femoral bone model superimposed with a 3D femoral implant model with the superior/inferior translation depicted.
Figure 33:
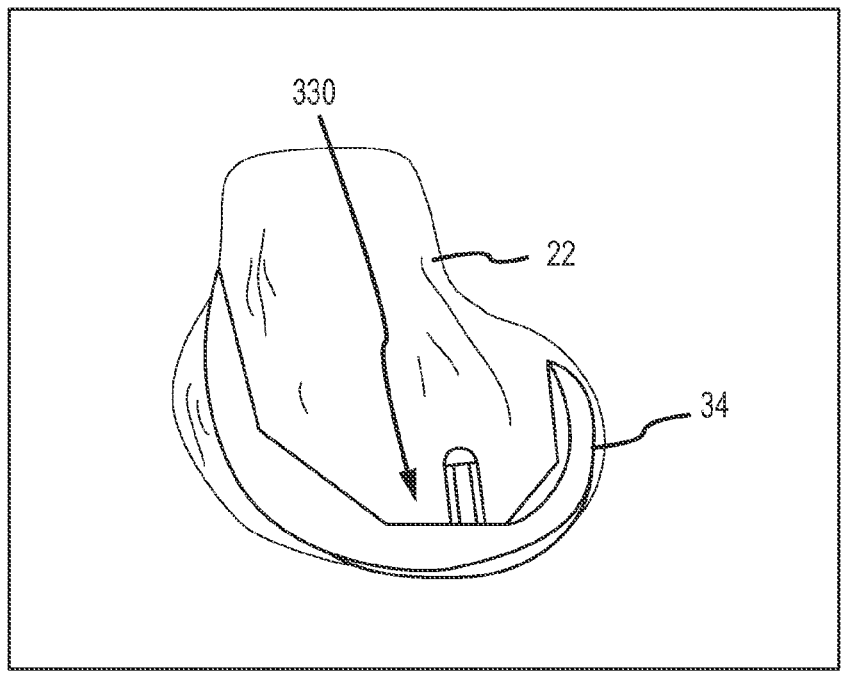
FIG. 33 is a sagittal view of the 3D femoral bone model superimposed with a 3D femoral implant model with the anterior/posterior translation depicted and flexion/extension depicted.

For example, as shown in FIGS. 32 and 33, which are, respectively, coronal and sagittal views of the femoral bone model 22 of the superimposed model 100, in one embodiment, the resection plane 330 of the femoral implant model 34 includes the resection line 320, the femoral implant resection plane 330 being orthogonal to the femoral mechanical axis 68. Also, the resection line 320 via the above-described operation of Block 1010 of FIG. 1L is located such that the condylar surfaces of the femoral implant model 34 are adjacent the condylar surfaces of the femoral bone model 22 and, in some cases, essentially coextensive with each other over portions of the condylar surfaces.

Figure 34:
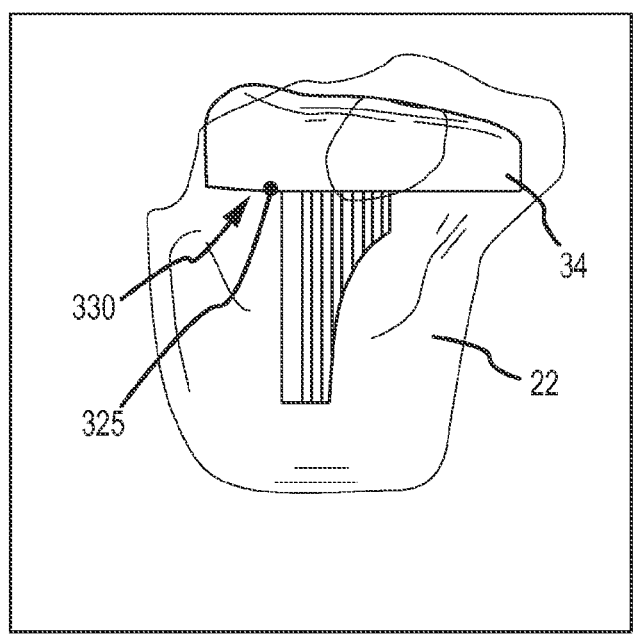
FIG. 34 is a sagittal view of the 3D tibial bone model superimposed with a 3D tibial implant model with the superior/inferior translation depicted and flexion/extension (i.e., tibial slope depicted).

Similarly, as can be understood from FIGS. 34, which is a sagittal view of the tibial bone model 22 of the superimposed model 100, in one embodiment, the resection plane 330 of the tibial implant model 34 includes the resection line 325 (shown as a point), the tibial implant resection plane 330 being orthogonal to the tibial mechanical axis 70. Also, the resection line 325 via the above-described operation of Block 1010 of FIG. 1L is located such that the condylar surfaces of the tibial implant model 34 are adjacent the condylar surfaces of the tibial bone model 22 and, in some cases, essentially coextensive with each other over portions of the condylar surfaces.

Figure 35:
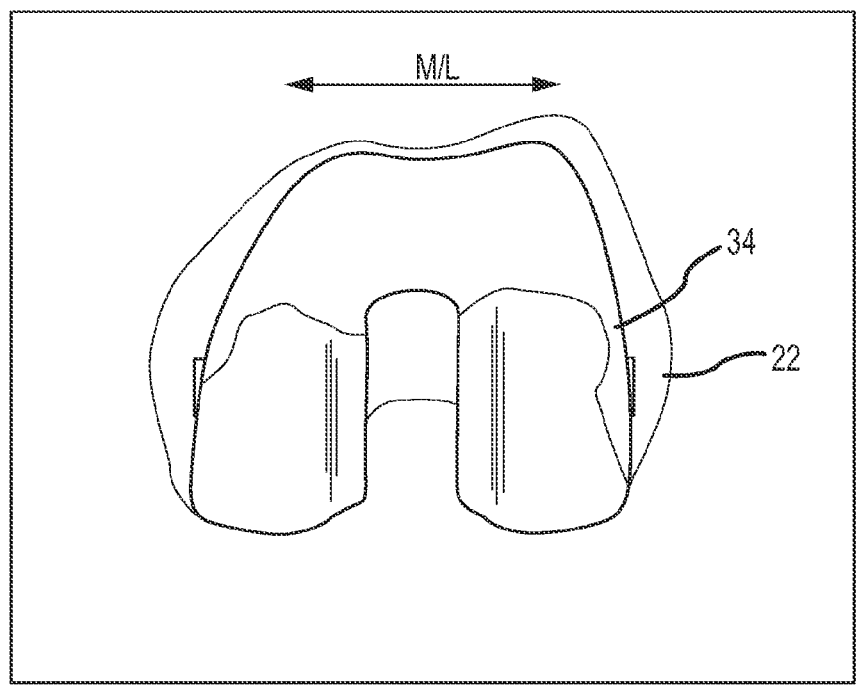
FIG. 35 is an axial or transverse view of the 3D femoral bone model superimposed with a 3D femoral implant model with the medial/lateral translation depicted.
Figure 36:
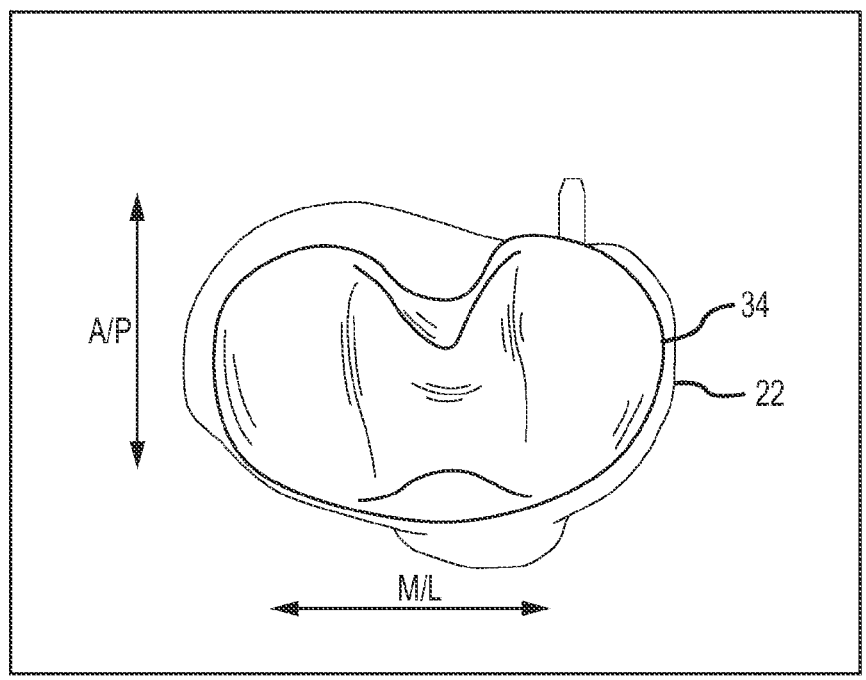
FIG. 36 is an axial or transverse view of the 3D tibial bone model superimposed with a 3D tibial implant model with the medial/lateral and anterior/posterior translations depicted.

As can be understood from FIG. 35, which is an axial view of the femoral implant model 34 superimposed on the femoral bone model 22, the femoral implant model 34 is centered medial-lateral relative to the femoral bone model 22 to have symmetric medial-lateral overhang, thereby completing the medial-lateral translation of the implant model. Similarly, as can be understood from FIG. 36, which is an axial view of the tibial implant model 34 superimposed on the tibial bone model 22, the tibial implant model 34 is centered medial-lateral and anterior-posterior relative to the tibial bone model 22 to have equal bone exposed circumferentially, the size of the tibial implant model 34 being adjusted as necessary, thereby completing the medial-lateral translation and the anterior-posterior translation of the implant model.

Femoral implant model sizing may be completed by first sizing the femoral implant model 34 in the sagittal view so as to fit the distal condyles and anterior cortex of the femoral bone model 22. Inspections for fit are made in the coronal and axial views. The best implant size is determined based on the distance form the posterior condylar line to the anterior cortex. If notching of the femoral shaft is present, the femoral implant model 34 flexed up to a maximum of approximately five degrees and reassessed for notching. If notching is still present, then the femoral implant model 34 is upsized and returned to a neutral alignment. If notching is again present, then the femoral implant model 34 is flexed up to a maximum of approximately five degrees and the medial-lateral overhang is assessed and a size for the femoral implant model is selected.

As can be understood from FIG. 33, the posterior position of the femoral implant model 34 is maintained relative to the femoral bone model 22 while the anterior-posterior position is modified by increasing or decreasing the size of the femoral implant model 34. This completes the anterior-posterior translation of the femoral implant model.

As can be understood from FIG. 1M, in one embodiment, the orientation of femur and tibia aspects of superimposed models 100, 34 are adjusted so resections 320, 325 are generally parallel, the condylar surfaces of each implant model 34 generally correspond relative to each other, and the femoral and tibial mechanical axes 68, 70 generally align with the mechanical axis 72 [Block 1020]. Similar to described above with respect to Block 195 of FIG. 1H, the various models and axes depicted as described in Block 1020 may be sent to the physician as a coronal view snapshot for review. In a manner similar to that described above with respect to FIG. 1I, the physician may review the provided coronal view snapshot and accept the POP as depicted therein or propose modifications to the POP. Once the POP is approved by the physician, the POP is employed as saw cut and drill hole data 44 [Block 240 of FIG. 1K] and then combined with the jig data 46 to form integrated jig data 48 [Block 270 of FIG. 1K], the manufacture of the jigs 2A, 2B then preceding as described in Blocks 275-285 of FIG. 1K.

The discussion provided herein is given in the context of TKR and TKR jigs and the generation thereof. However, the disclosure provided herein is readily applicable to uni-compartmental or partial arthroplasty procedures in the knee or other joint contexts. Thus, the disclosure provided herein should be considered as encompassing jigs and the generation thereof for both total and uni-compartmental arthroplasty procedures.

Although the present invention has been described with reference to preferred embodiments, persons skilled in the art will recognize that changes may be made in form and detail without departing from the spirit and scope of the invention.

What is claimed is:

1. A method of manufacturing a custom arthroplasty resection guide, the method comprising:
    generate a three dimensional femur bone computer model from MRI knee coil two dimensional images, wherein the MRI knee coil two dimensional images include a knee region of a patient;
    locate positions of an approximate hip center and an approximate femur knee center in coronal view MRI body coil two dimensional images, wherein the positions are relative to at least two axes in a global coordinate system of a computer environment and wherein the MRI body coil two dimensional images include a hip region of the patient and the knee region of the patient;
    cause the three dimensional femur bone computer model and approximate hip center and approximate femur knee center to generally correspond with each other with respect to location and orientation in the global coordinate system of the computer environment by aligning first locations of knee landmarks in the MRI knee coil two dimensional images and second locations of the knee landmarks in the MRI body coil two dimensional images;
define across the three dimensional femur bone computer model a femoral mechanical axis between the approximate femur knee center and the approximate hip center;
locate a most distal condylar point of the three dimensional femur bone computer model;
define a distal plane that is orthogonal to the femoral mechanical axis in a coronal view of the three dimensional femur bone computer model, wherein the distal plane also passes through the most distal condylar point;
define a resection plane that is parallel to the distal plane and proximally offset a distance along the femoral mechanical axis from the distal plane; and
manufacture the custom arthroplasty resection guide by using data associated with the resection plane to define a resection guide in the custom arthroplasty resection guide.

2. The method of claim 1, wherein the three dimensional femur bone computer model includes at least one of a femur bone only computer model or a femur arthritic computer model representing bone and cartilage.

3. The method of claim 1, wherein the distance of proximal offset between the distal plane and the resection plane is based on a dimension of a candidate femoral implant.

4. The method of claim 1, wherein in causing the three dimensional femur bone computer model and approximate hip center and approximate femur knee center to generally correspond with each other with respect to location and orientation in the global coordinate system of the computer environment, the method further includes:
identifying the first locations of the knee landmarks in the MRI knee coil two dimensional images;
identifying the second locations of the knee landmarks in the MRI body coil two dimensional images; and
causing a computer processor to run a transformation with the first and second locations, causing the MRI knee coil two dimensional images and MRI body coil two dimensional images to generally correspond with each other with respect to location and orientation in the global coordinate system.

5. The method of claim 4, wherein the transformation employs an Iterative Closest Point algorithm or gradient descent optimization.

6. The method of claim 4, wherein the transformation causes the MRI knee coil two dimensional images to reposition in the global coordinate system to the location and orientation of the MRI body coil two dimensional images.

7. The method of claim 1, wherein the approximate femur knee center is close to a medial-lateral center of a distal femur intercondylar groove, and the approximate hip center is at a center of a femur head.

8. A method of manufacturing a custom arthroplasty resection guide, the method comprising:
generate a three dimensional tibia bone computer model from MRI knee coil two dimensional images, wherein the MRI knee coil two dimensional images include a knee region of a patient;
locate positions of an approximate ankle center and an approximate tibia knee center in coronal view MRI body coil two dimensional images, wherein the positions are relative to at least two axes in a global coordinate system of a computer environment and wherein the MRI body coil two dimensional images include an ankle region of the patient and the knee region of the patient;
cause the three dimensional tibia bone computer model and approximate ankle center and approximate tibia knee center to generally correspond with each other with respect to location and orientation in the global coordinate system of the computer environment by aligning first locations of knee landmarks in the MRI knee coil two dimensional images and second locations of the knee landmarks in the MRI body coil two dimensional images;
define across the three dimensional tibia bone computer model a tibial mechanical axis between the approximate tibia knee center and the approximate ankle center;
locate a condylar point of the three dimensional tibia bone computer model;
define a proximal plane that is orthogonal to the tibial mechanical axis in a coronal view of the three dimensional tibia bone computer model, wherein the proximal plane also passes through a condylar point;
define a resection plane that is parallel to the proximal plane and distally offset a distance along the tibial mechanical axis from the proximal plane; and
manufacture the custom arthroplasty resection guide by using data associated with the resection plane to define a resection guide in the custom arthroplasty resection guide.

9. The method of claim 8, wherein the three dimensional tibia bone computer model includes at least one of a tibia bone only computer model or a tibia arthritic computer model representing bone and cartilage.

10. The method of claim 8, wherein the distance of distal offset between the proximal plane and the resection plane is based on a dimension of a candidate tibial implant.

11. The method of claim 8, wherein in causing the three dimensional tibia bone computer model and approximate ankle center and approximate tibia knee center to generally correspond with each other with respect to location and orientation in the global coordinate system of the computer environment, the method further includes:
identifying the first locations of the knee landmarks in the MRI knee coil two dimensional images;
identifying the second locations of the knee landmarks in the MRI body coil two dimensional images; and
causing a computer processor to run a transformation with the first and second locations, causing the MRI knee coil two dimensional images and MRI body coil two dimensional images to generally correspond with each other with respect to location and orientation in the global coordinate system.

12. The method of claim 11, wherein the transformation employs an Iterative Closest Point algorithm or gradient descent optimization.

13. The method of claim 11, wherein the transformation causes the MRI knee coil two dimensional images to reposition in the global coordinate system to the location and orientation of the MRI body coil two dimensional images.

14. The method as in any of claim 1 or 8, in which computer processing is employed in aligning the first locations of the knee landmarks in the MRI knee coil two dimensional images and the second locations of the knee landmarks in the MRI body coil two dimensional images.

15. The method as in any of claim 1 or 8, in which an image spacing of the MRI body coil two dimensional images is different from an image spacing of the MRI knee coil two dimensional images.

16. The method of claim 8, wherein the approximate tibia knee center is close to a medial-lateral center of a proximal tibia spine, and the approximate ankle center is close to a cortical bone rim of an ankle plafond.

17. A method of manufacturing a custom arthroplasty resection guide, the method comprising:
   a) locate coordinate system points in a computer environment, the coordinate system points approximating hip, knee and ankle centers in coronal two dimensional images of a first set of two dimensional images;
   b) generate in a computer environment a three dimensional knee computer model from a second set of two dimensional images;
   c) employ computer processing to cause the three dimensional knee computer model and the coordinate system points to be positioned relative to each other as a combined computer model in a global coordinate system generally as if the three dimensional knee computer model were generated from the first set of two dimensional images;
   d) preoperatively plan an arthroplasty procedure with the combined computer model of step c) via a method including:
      define a mechanical axis across the three dimensional knee computer model between a pair of the coordinate system points including the coordinate system point approximating the knee center and at least one of the coordinate system points approximating the hip center or approximating the ankle center; and
      define a resection plane parallel to, and offset a distance along the mechanical axis from, a reference plane that:
         1) is orthogonal to the mechanical axis in a coronal view and
         2) extends through a condylar point on the three dimensional knee computer model, wherein the condylar point is either a most distal femoral condyle point or a tibial condyle point; and
   e) manufacture the custom arthroplasty resection guide by using data associated with the resection plane to define a resection guide in the custom arthroplasty resection guide.

18. The method of claim 17, further comprising generating the first set of two dimensional images via MRI body coil imaging.

19. The method of claim 18, further comprising generating the second set of two dimensional images via MRI knee coil imaging.

20. The method of claim 17, wherein step c) includes:
   determining a first set of locations in the first set of two dimensional images for a set of knee landmarks;
   determining a second set of locations in the second set of two dimensional images for the set of knee landmarks; and
   employing computer processing in running a transformation process for the first and second sets of locations to generally positionally match the first and second sets of locations in the global coordinate system.

21. The method of claim 20, wherein the transformation employs an Iterative Closest Point algorithm or gradient descent optimization.

22. The method of claim 20, wherein the transformation causes the second set of two dimensional images to reposition in the global coordinate system to the location and orientation of the first set of two dimensional images.

23. The method of claim 17, wherein the three dimensional knee computer model includes a three dimensional femur bone computer model and the mechanical axis is a femoral mechanical axis.

24. The method of claim 23, wherein the condylar point is the most distal femoral condylar point.

25. The method of claim 17, wherein the three dimensional knee computer model includes a three dimensional tibia bone computer model and the mechanical axis is a tibial mechanical axis.

26. The method of claim 25, wherein the condylar point is the tibial condylar point.

27. The method of claim 17, wherein the three dimensional knee computer model includes at least one of a bone-only model or an arthritic model including bone and cartilage.

28. The method of claim 27, wherein the arthritic model is an overestimated model with surface boundaries pushed outwardly from an interior of the overestimated model in areas of the overestimated model corresponding to areas resulting from poor accuracy due to limitations in at least one of imaging limitations or manufacturing limitations.

29. The method of claim 17, in which an image spacing of the first set of two dimensional images is different from an image spacing of the second set of two dimensional images.

30. The method of claim 17, wherein the three dimensional knee computer model includes a three dimensional femur computer model, and the coordinate system point approximating the knee center includes an approximate femur knee center, and the coordinate system point approximating the hip center includes an approximate hip center.

31. The method of claim 30, wherein the approximate femur knee center is close to a medial-lateral center of a distal femur intercondylar groove.

32. The method of claim 31, wherein the approximate hip center is at a center of a femur head.

33. The method of claim 17, wherein the three dimensional knee computer model includes a three dimensional tibia computer model, and the coordinate system point approximating the knee center includes an approximate tibia knee center, and the coordinate system point approximating the ankle center includes an approximate ankle center.

34. The method of claim 33, wherein the approximate tibia knee center is close to a medial-lateral center of a proximal tibia spine.

35. The method of claim 34, wherein the approximate ankle center is close to a cortical bone rim of an ankle plafond.

* * * * *